US011459612B2

(12) United States Patent
Martín Fernández et al.

(10) Patent No.: US 11,459,612 B2
(45) Date of Patent: Oct. 4, 2022

(54) METHOD FOR DIAGNOSING CARDIOMYOPATHIES

(71) Applicant: CENTRO NACIONAL DE INVESTIGACIONES CARDIOVASCULARES CARLOS III (F.S.P.), Madrid (ES)

(72) Inventors: María Pilar Martín Fernández, Madrid (ES); Raquel Sánchez Díaz, Madrid (ES); Adela Matesanz Marín, Madrid (ES); Luis Jesús Jiménez Borreguero, Madrid (ES); Francisco Sánchez Madrid, Madrid (ES)

(73) Assignee: CENTRO NACIONAL DE INVESTIGACIONES CARDIOVASCULARES CARLOS III (F.S.P.), Madrid (ES)

( * ) Notice: Subject to any disclaimer, the term of this patent is extended or adjusted under 35 U.S.C. 154(b) by 0 days.

(21) Appl. No.: 15/780,888

(22) PCT Filed: Nov. 30, 2016

(86) PCT No.: PCT/EP2016/079335
§ 371 (c)(1),
(2) Date: Jun. 1, 2018

(87) PCT Pub. No.: WO2017/093353
PCT Pub. Date: Jun. 8, 2017

(65) Prior Publication Data
US 2018/0355427 A1    Dec. 13, 2018

(30) Foreign Application Priority Data

Dec. 1, 2015  (EP) .................... 15197221
Dec. 1, 2015  (EP) .................... 15382596

(51) Int. Cl.
*C12Q 1/6876* (2018.01)
*C12Q 1/6883* (2018.01)

(52) U.S. Cl.
CPC ........ *C12Q 1/6876* (2013.01); *C12Q 1/6883* (2013.01); *C12Q 2525/207* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 10,907,135 | B2 | 2/2021 | Redondo Moya et al. | |
| 2001/0053519 | A1* | 12/2001 | Fodor ................... | B82Y 30/00 435/6.11 |
| 2007/0298425 | A1* | 12/2007 | Hogan ................ | C12Q 1/6881 435/6.11 |
| 2009/0306181 | A1 | 12/2009 | Ikeda et al. | |
| 2012/0289420 | A1* | 11/2012 | Mohapatra ........... | C12Q 1/6883 506/9 |
| 2014/0004520 | A1* | 1/2014 | Mohapatra ........... | C12Q 1/6851 435/6.11 |
| 2015/0057165 | A1* | 2/2015 | Dave .................... | C12Q 1/6886 506/7 |
| 2015/0064704 | A1 | 3/2015 | Keller et al. | |
| 2015/0337332 | A1* | 11/2015 | Ruohoa-Baker ..... | C12N 15/113 514/44 R |
| 2021/0186989 | A1 | 6/2021 | Sancho Madrid et al. | |

FOREIGN PATENT DOCUMENTS

| RU | 2 569 459 C1 | 11/2015 |
| WO | 2007/095614 A2 | 8/2007 |
| WO | 2008/147974 A1 | 12/2008 |
| WO | 2009/012468 A2 | 1/2009 |
| WO | 2015/018771 A1 | 2/2015 |

OTHER PUBLICATIONS

Humphreys (PLOS One Feb. 2012 vol. 7 Issue 2 e30933 pp. 1-18).*
Ahern, H. (The Scientist. Jul. 1995. 9(15): 20-25) (Year: 1995).*
NCBI Database. Gen Bank Accession No. AC024995.8, Dec. 12, 2001, pp. 1-60, available via URL: <ncbi.nlm.nih.gov/nuccore/ac024995.8> (Year: 2001).*
NCBI Database Gen Bank Accession No. NC_000008.11, Feb. 3, 2014, pp. 1-3, available via URL: <ncbi.nlm.nih.gov/nuccore/568815590?sat=21&satkey=4512911> (Year: 2014).*
Invitrogen. "BAG (Bacterial Artificial Chromosome) Clone Collections" available via URL: < tools.thermofisher.com/content/sfs/manuals/bac_clones_man.pdf >, Version D, Oct. 14, 2008, p. 1-16 (Year: 2008).*
Kwan etal Folia Histochem Cytobiol. 2009. 47(2): 135-142 (Year: 2009).*
Ammirati et al., "Circulating $CD4^+CD25^{hi}CD127^{lo}$ regulatory T-Cell Levels Do Not Reflect the extent or Severity of Carotid and Coronary Atherosclerosis," *Arterioscler Thromb Vase Biol.* 30:1832-1841, 2010.
Andréoletti et al., "Viral causes of human myocarditis," *Archives of Cardiovascular Disease* 102:559-568, 2009.

(Continued)

*Primary Examiner* — Carla J Myers
(74) *Attorney, Agent, or Firm* — Seed IP Law Group LLP

(57) ABSTRACT

The present invention provides an in vitro method for obtaining data useful for diagnosing a cardiomyopathy in a human subject, wherein the method comprises using, as an indicator, the expression levels, obtained from a biological sample isolated from the human subject, preferably a plasma sample, of one or more of the following miRNAs miR-721 and/or miR-155); and obtaining a result of the method by comparing the expression levels of said one or more miR-NAs with a reference value or with the expression levels of a control, indicator of the absence of cardiomyopathy.

11 Claims, 35 Drawing Sheets

Specification includes a Sequence Listing.

(56) References Cited

OTHER PUBLICATIONS

Baldeviano et al., "Interleukin-17A is Dispensable for Myocarditis but Essential for the Progression to Dilated Cardiomyopathy," *Circulation Research* 106:1646-1655, 2010.

Carvalheiro et al., "Phenotypic and Functional Alterations on Inflammatory Peripheral Blood Cells After Acute Myocardial Infarction," *J. of Cardiovasc. Trans. Res.* 5:309-320, 2012 (12 pages).

Cruz-Adalia et al., "CD69 Limits the Severity of Cardiomyopathy After Autoimmune Myocarditis," *Circulation* 122:1396-1404, 2010.

Felker et al., "Underlying Causes and Long-Term Survival in Patients with Initially Unexplained Cardiomyopathy," *The New England Journal of Medicine* 342(15): 1077-1084, 2000.

Fousteri et al., "Nasal cardiac myosin peptide treatment and OX40 blockade protect mice from acute and chronic virally-induced myocarditis," *J. Autoimmun.*36(3-4):2W-22Q, May 2011, NIH Public Access Author Manuscript, available in PMC May 1, 2012 (21 Pages).

Frustaci et al., "Randomized study on the efficacy of immunosuppressive therapy in patients with virus-negative inflammatory cardiomyopathy: the TIMIC study," *European Heart Journal* 30:1995-2002, 2009.

Fung et al., "Myocarditis," *Circ Res.* 118:496-514, 2016.

Hata et al., "Critical role of Th17 cells in inflammation and neovascularization after ischaemia," *Cardiovascular Research* 90:364-372, 2011.

Humphreys et al., "Complexity of Murine Cardiomyocyte miRNA Biogenesis, Sequence Variant Expression and Function," *PLOS ONE* 7(2):e30933, 2012 (18 Pages).

Jaguszewski et al., "A signature of circulating microRNAs differentiates takotsubo cardiomyopathy from acute myocardial infarction," *European Heart Journal* 35:999-1006, 2014.

Kaya et al., "Cutting Edge: A Critical Role for IL-10 in Induction of nasal Tolerance in Experimental Autoimmune Myocarditis," *The Journal of Immunology* 168:1552-1556, 2002.

Mariano et al., "The involvement of CD4+ CD25+T cells in the acute phase of *Trypanosoma cruzi* infection," *Microbes and Infection* 10:825-833, 2008.

Nakahama et al., "Aryl hydrocarbon receptor-mediated induction of the microRNA-132/212 cluster promotes interleukin-17-producing T-helper cell differentiation," *PNAS* 110(29):11964-11969, Jul. 16, 2013.

Noutsias et al., "Expression of functional T-cell markers and T-cell receptor Vbeta repertoire in endomyocardial biopsies from patients presenting with acute myocarditis and dilated cardiomyopathy," *European Journal of Heart Failure* 73:611-618, 2011.

Ono et al., "Control of Autoimmune Myocarditis and Multiorgan Inflammation by Glucocorticoid-Induced TNF receptor Family-related Protein$^{high}$, Foxp3-Expressing CD25+ and CD25− regulatory T Cells[1]," *The Journal of immunology* 176:4748-4756, 2006.

Pfaff et al., "miRNA screening reveals a new miRNA family stimulating iPS cell generation via regulation of Meox2," *EMBO Reports* 72(11):1153-1159, 2011.

Rangachari et al., "T-bet negatively regulates autoimmune myocarditis by suppressing local production of interleukin 17," *The Journal of Experimental Medicine* 203(8):2009-2019, Aug. 7, 2006.

Sardella et al., " Frequency of naturally-occurring regulatory T cells is reduced in patients with ST-segment elevation myocardial infarction," *Thrombosis Research* 720:631-634, 2007.

Shi et al., "Regulatory T Cells protect Mice Against Coxsackievirus-Induced Myocarditis Through the Transforming Growth Factor P-Coxsackie-Adenovirus Receptor Pathway," *Circulation* 121:2624-2634, 2010.

Smith et al., "Myosin-Induced Acute Myocarditis is a T Cell-Mediated Disease," *The Journal of Immunology* 147(7):2141-2147, Oct. 1, 1991.

Smith et al., "The Role of T Cells in Myosin-Induced Autoimmune Myocarditis," *Clinical Immunology and Immunopathology* 68(2):100-106, 1993.

Sonderegger et al., "GM-CSF mediates autoimmunity by enhancing IL-6-dependent Th17 cell development and survival," *The Journal of Experimental Medicine* 205(10):2281-2294, 2008.

Sonderegger et al., "Neutralization of IL-17 by active vaccination inhibits IL-23-dependent autoimmune myocarditis," *Eur. J. Immunol.* 36:2849-2856, 2006.

van den Hoogen et al., "Heart Failure in Chronic Myocarditis: A Role for microRNAs?" *Current Genomics* 76:88-94, 2015.

Wheeler et al., "Identification of new central nervous system specific mouse microRNAs," *FEBS Letters* 580:2195-2200, 2006.

Wu et al., "Role of the MEOX2 homeobox gene in neurovascular dysfunction in Alzheimer disease," *Nature Medicine* 11(9):959-965, Sep. 2005.

Yamashita et al., "IL-6-mediated Th17 differentiation through RORγt is essential for the initiation of experimental autoimmune myocarditis," *Cardiovascular Research* 91:640-648, 2011.

Yi et al., "The prevalence of Th17 cells in patients with dilated cardiomyopathy," *Clin Invest Med* 32(2):E144-E150, 2009.

Yuan et al., "Th17 Cells Facilitate the Humoral Immune Response in Patients with Acute Viral Myocarditis," *J. Clin. Immunol.* 30:226-234, 2010.

Zhang et al., "Downregulation of miR-1 45-5p correlates with poor prognosis in gastric cancer," *European Review for Medical and Pharmacological Sciences* 20:3026-3030, 2016.

Zouggari et al., "Regulatory T Cells modulate Postischemic Neovascularization," *Circulation* 120:1415-1425, 2009.

U.S. Appl. No. 17/122,962, filed Dec. 15, 2020.
U.S. Appl. No. 17/284,195, filed Apr. 9, 2021.

\* cited by examiner

Stem-loop sequence mmu-mir-721

| | |
|---|---|
| Accession | MI0004708 |
| Symbol | MGI:Mir721 |
| Description | Mus musculus miR-721 stem-loop |

(SEQ ID NO:8)

```
         ggaaga       uaaa    ac       aa     ac   g   a
5'                                              aagu  cu  gg  u
                                                              g
Stem-loop 3'         c cguaa   uuc   uuu    uuua   ga uc  u
         aagguucguccuca         uuq   uu   ac     a   g   u
```

Fig. 2

[100 bp insert]

Mir 721 clon100 (SEQ ID NO:9)
GCAGCTCCTAGACTGTTCTGCGAGCATAGCTCCTTCTCCTCCTTATCCCTGA
CCTGGATCAAGCTCAGATTGTCCTTCTGTATAAAGGATGTTGTGGGCATAGT
GCTCATTTCTCTCAATCCACTAGCCTGAAGACATGGAGGGCAGAGAGAGATT
CAGGTTTCTGGGAAGACAGTGCAATTAAAAGGGGGAAAAAGTACCTGGGA
TGTTCTGAGAATTCATTTTTCTTGTTATTGCCACTCCTGCTTGGAAGAACT
ATGTTCCAAAATAGCTCTAGCAATCTAGCATAACATAAATATTTTAATGCT
GATTAAAATAATAATGAAAAGTCATGAATGAGAAAGGGACTGTGTATAGAGG
CCGCATAAGTGCCCACCAAGCCTGAGAGTCACATGATGGACAGTGTTGGTGT
TAAGC

```
                   XhoI
Mi721 fw  .5' ATAT-CTCGAG-ATTGTCCTTCTGTATA    (SEQ ID NO:10)
3'TM:36+30=66
                   EcoRI
Mi721 rev 3' ATAT-CTTAAG-TTTCTCATTCATGACT      (SEQ ID NO: 11)
5'TM:28+30=66
``` miR-721 immature sequence
100 bp up and down miR-721

Fig. 3

Sponge design for cloning into cap gfp

721spacer fw
EcoRI
aattctcccccttaattgcactgcgattctcccccttaatgacctgactgactgactgcgttctcccctttaa
ttgactgtcacttcccccttaatgcactgg 721spacer rev
BamHI
gatccagtgcaattaaggggggaagtgacagtgcaattaaggggggaacgtcaagtgcaagtgcaattaa
aggggggaatcgcagtgcaattaaggggggag INSERT
EcoRI
aattctcccccttaattgcactgcgattctcccccttaatgacctgactgactgactgcgttctcccctttaa
ttgactgtcacttcccccttaatgcactggatcgcagtgcaattaaggggggaatcgcagtgcaagtgcaa
ttaaggggggaatcgcagtgcaattaaggggggaatcgcagtgcaattaaggggggag
BamHI

FIG. 4

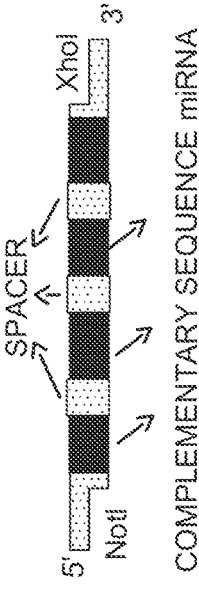
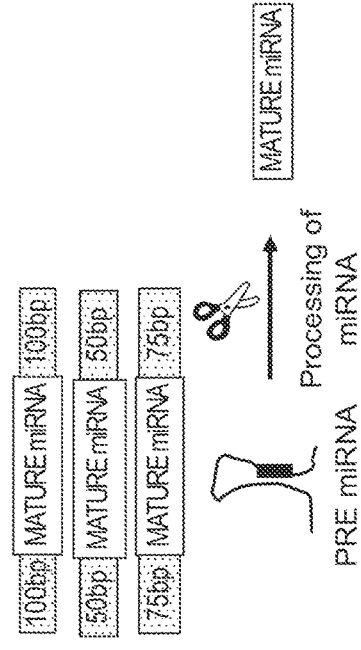
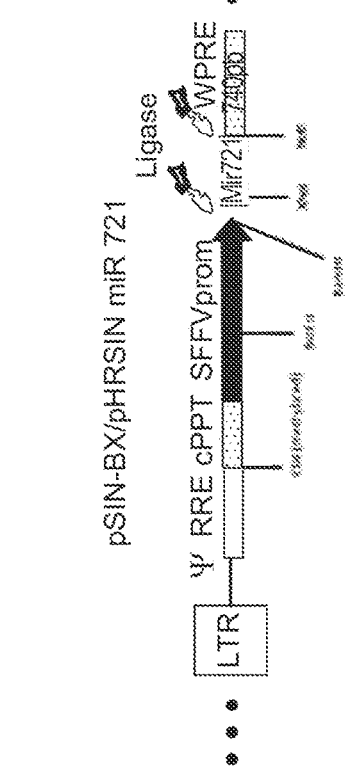
FIG. 5 mmu-130b -5P    CUCUUCCCUGUUGCACU (SEQ ID NO:22)
mmu-301b -5P    GCUCUGACUAGGUUGCACU (SEQ ID NO:23)
mmu-721         UUUUUCUUGUUAUUGCCACU (SEQ ID NO: 24)

3´UTR MEOX2 sequence        UUGCAC

...agagagggagatggatgtttgctttggcTTGCACtgaaaattaaattttgctaccaagag...
(SEQ ID NO: 25)

Fig. 8

(SEQ ID NO: 26)
mmu-130b 5´-CAGUGCAAUGAUGAAAGGGCAU-3´
3´UTR CD69  mmu-301b 5´-CAGUGCAAUGGUAUUGUCAAAGC-3´
sequence                                        (SEQ ID NO: 27)
mmu-721  5´-CAGUGCAAUUAAAAGGGGGAA-3´
(SEQ ID NO: 28)
... tttcaaagtgctggaaagaaaAGTGCAatacgtgtagtggcaga .....
(SEQ ID NO: 29)

mmu-130b 5´-CAGUGCAAUGAUGAAAGGGCAU-3´
3´UTR AHR  mmu-301b 5´-CAGUGCAAUGGUAUUGUCAAAGC-3´
sequence   mmu-721  5´-CAGUGCAAUUAAAAGGGGGAA-3´

...agaatagttcttacctcatatgcattttcAGTGTAtcttgtaaagaaatcaagtagtaaattgaagctt...
(SEQ ID NO: 30)

Fig. 9

MLEC s KO Control COP-GFP
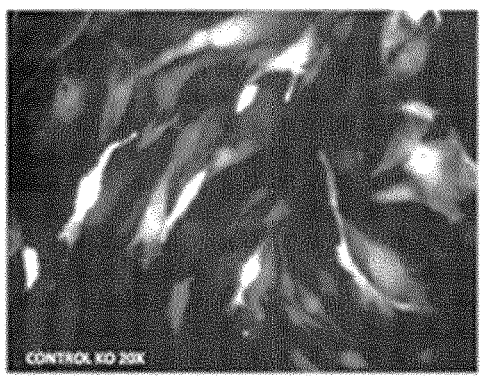
MLEC s WT Control COP-GFP
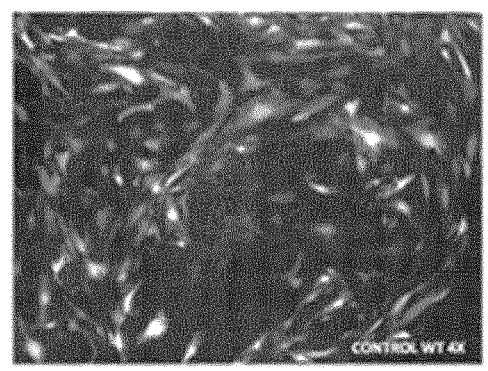
MLEC s KO COP-GFP Sponge2
MLEC s WT COP-GFP Sponge2
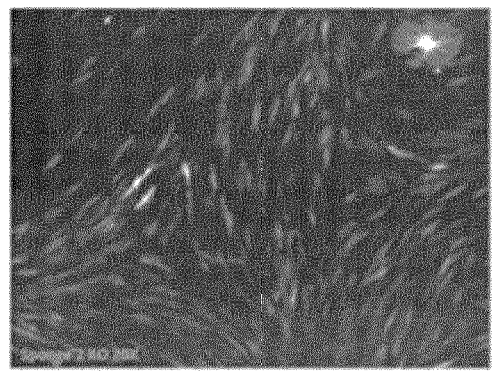
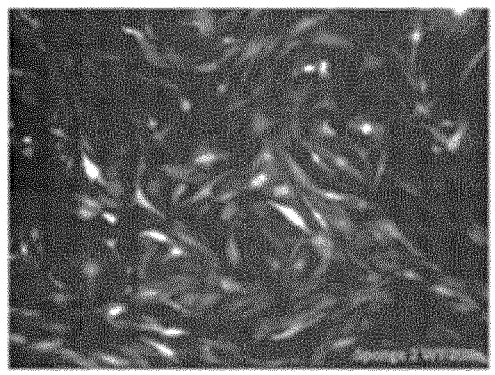
Fig. 11 A MLEC s KO Control COP-GFP 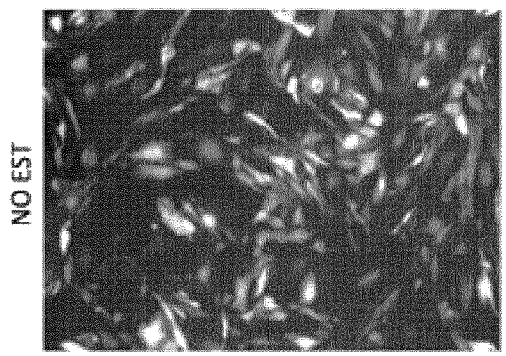 MLEC s WT Control COP-GFP 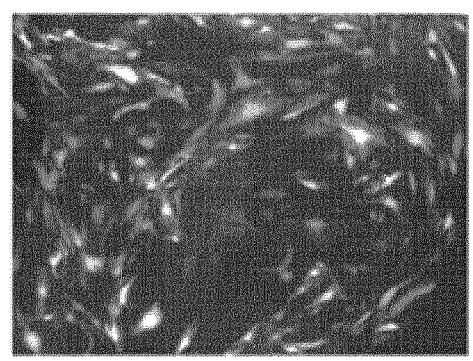
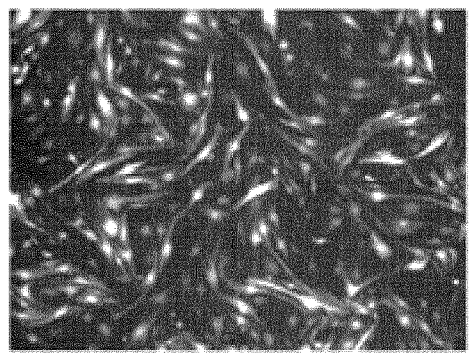 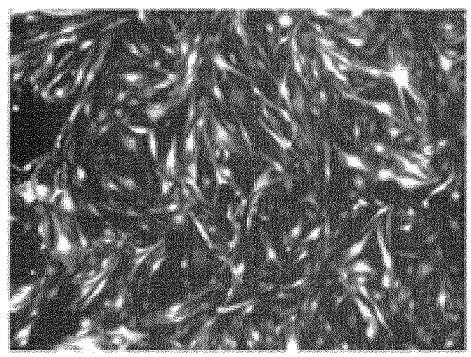
MLEC s KO COP-GFP Sponge2 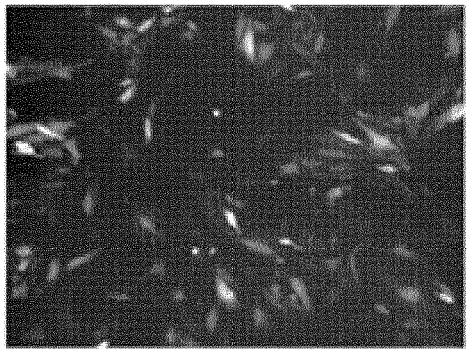 MLEC s WT COP-GFP Sponge2 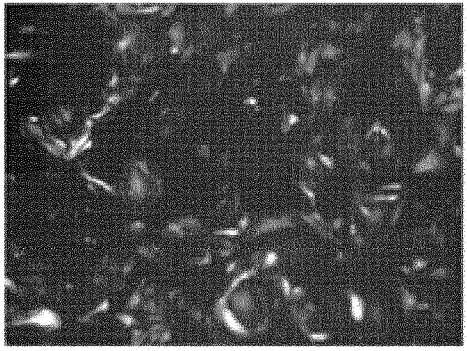
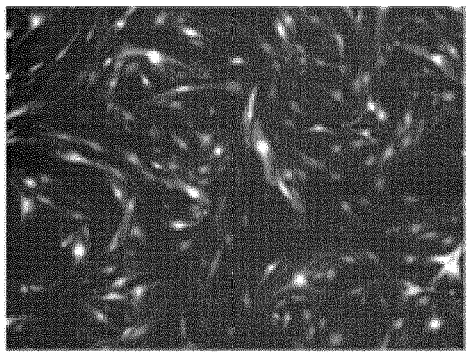 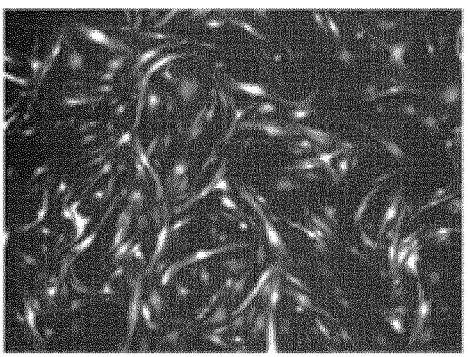
Fig. 11 B

FIG. 13

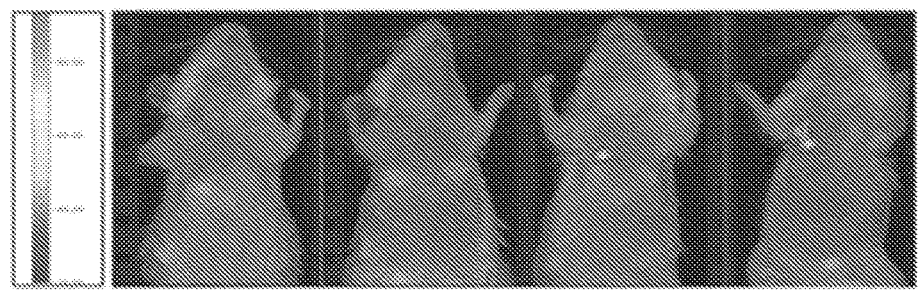
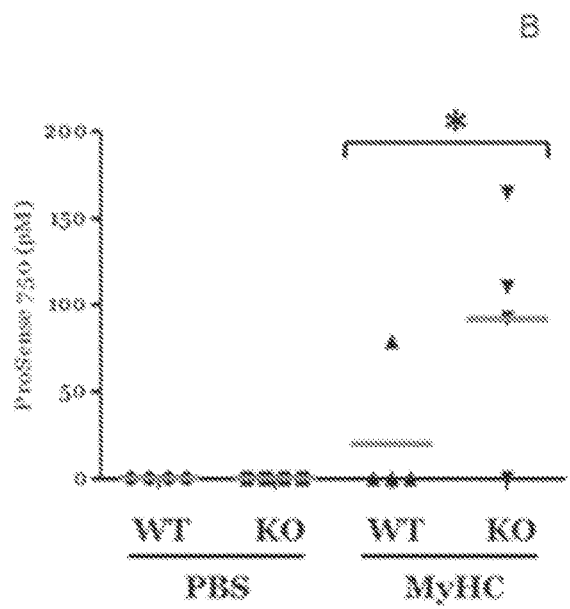
*FIG. 25*
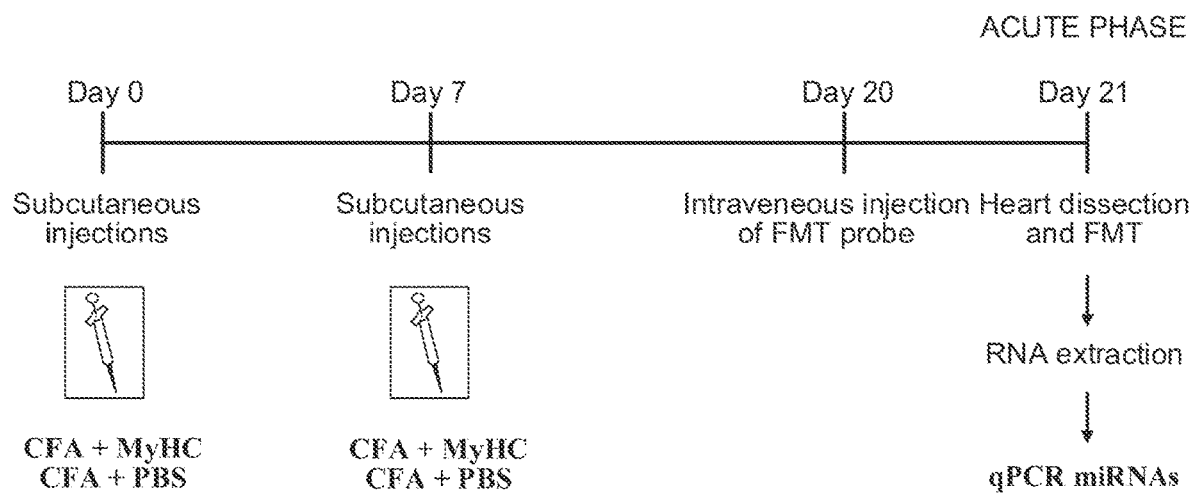
*FIG. 26*

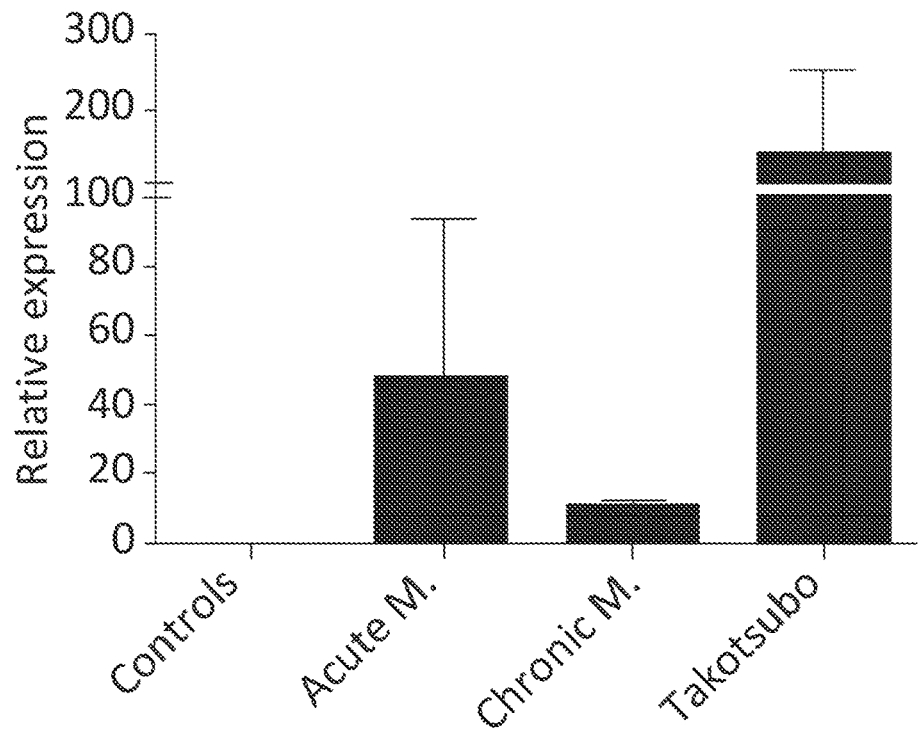
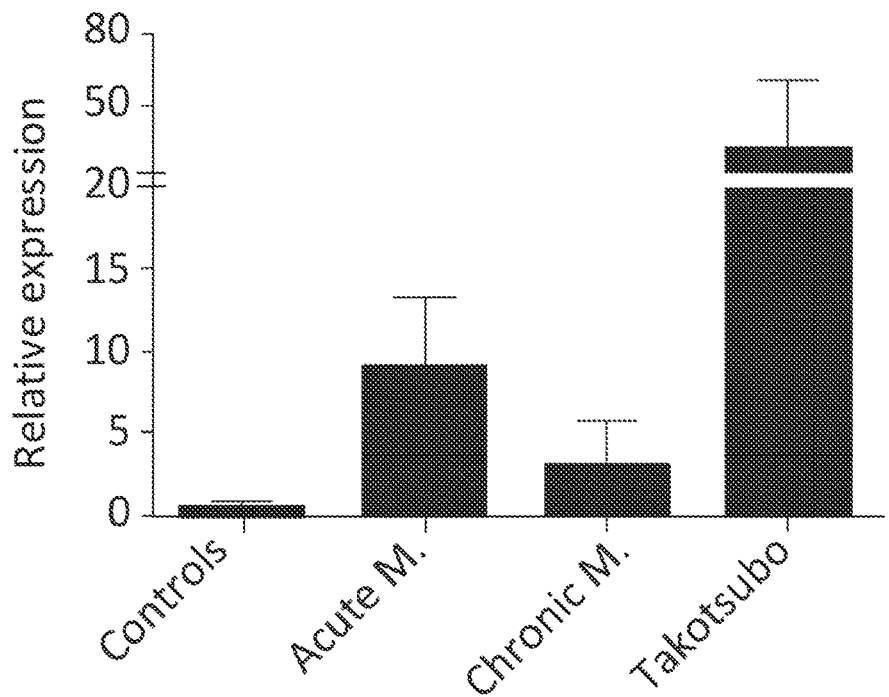
*FIG. 32*

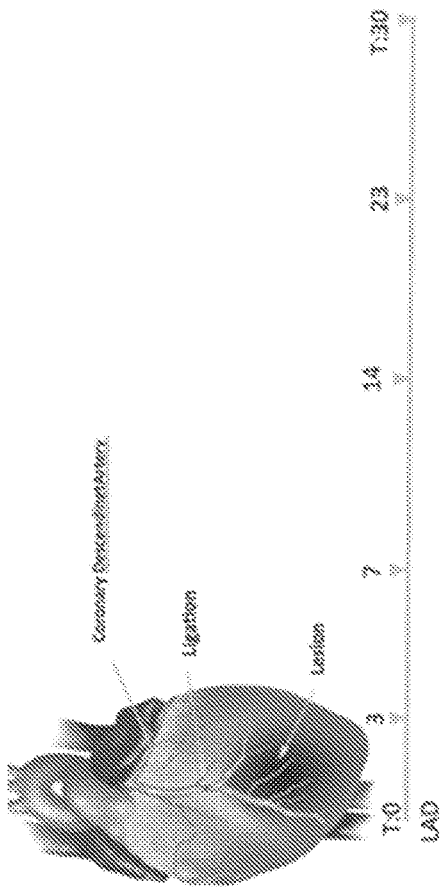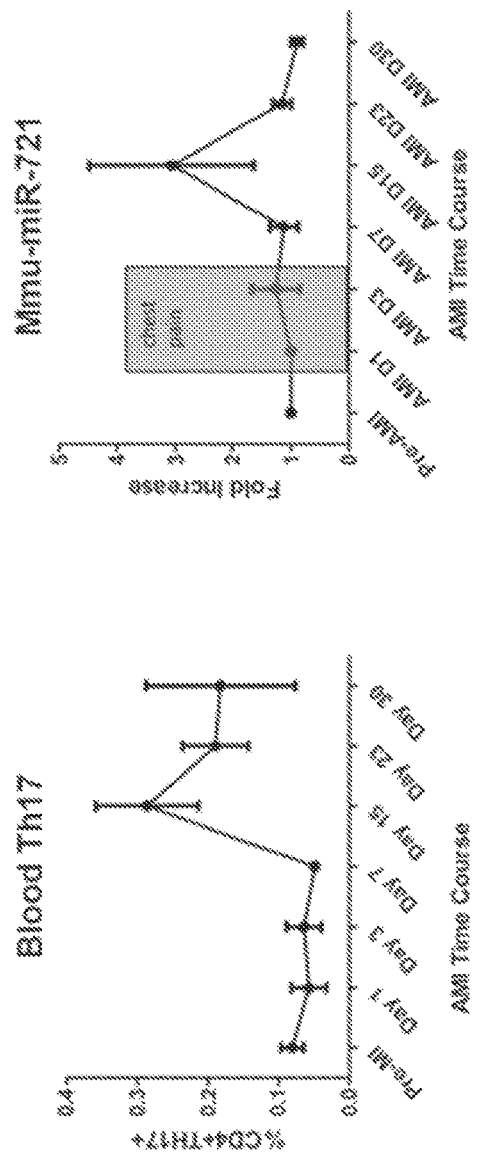
FIG. 33B

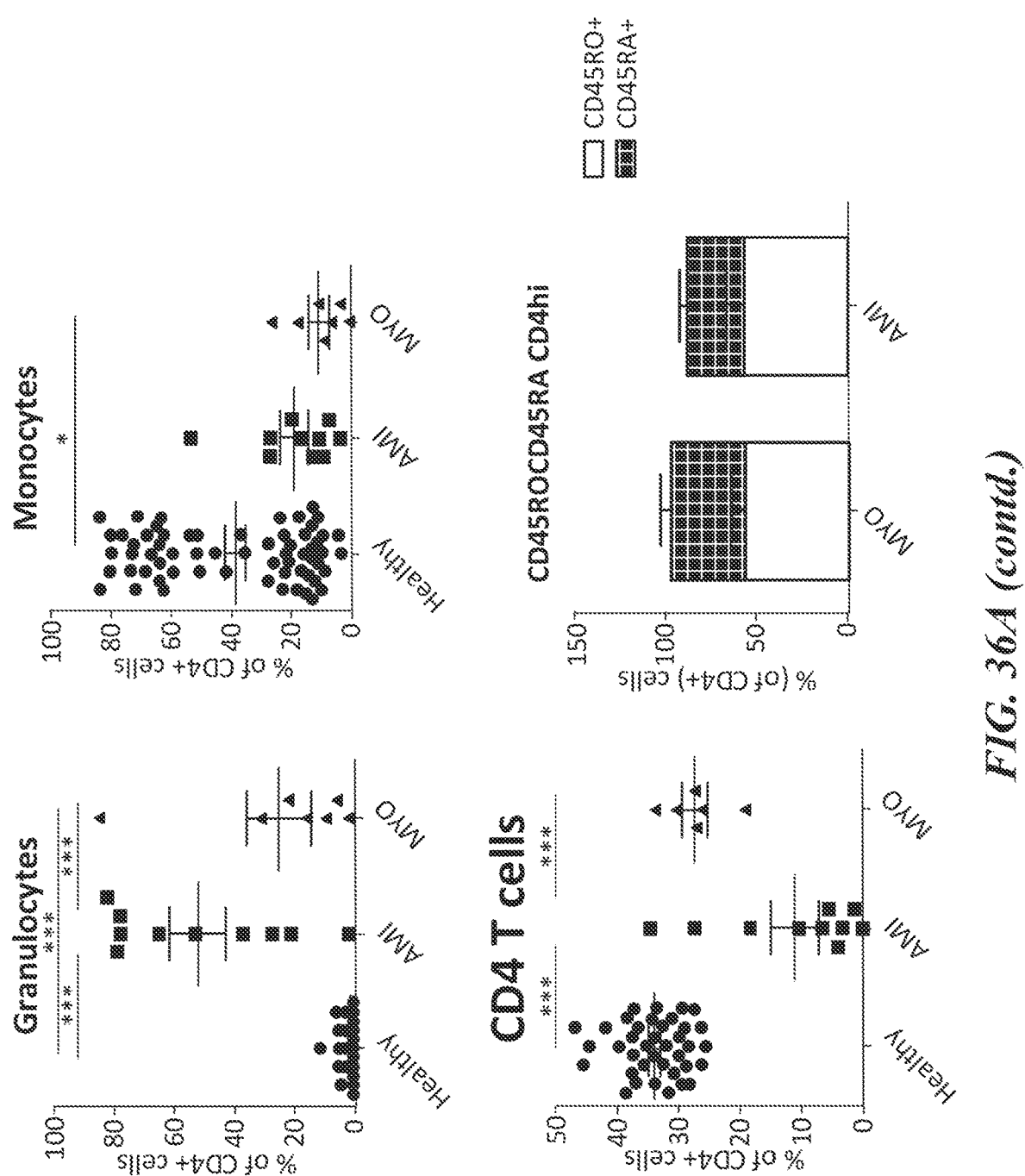
FIG. 36A (contd.)

SEQUENCE LISTING

```
<160> NUMBER OF SEQ ID NOS: 40

<210> SEQ ID NO 1
<211> LENGTH: 21
<212> TYPE: RNA
<213> ORGANISM: Artificial Sequence
<220> FEATURE:
<223> OTHER INFORMATION: murine miR-721 sequence

<400> SEQUENCE: 1
cagugcaauu aaaaggggga a                                                  21

<210> SEQ ID NO 2
<211> LENGTH: 23
<212> TYPE: RNA
<213> ORGANISM: Artificial Sequence
<220> FEATURE:
<223> OTHER INFORMATION: miR-155 murine

<400> SEQUENCE: 2
uuaaugcuaa uugugauagg ggu                                                23

<210> SEQ ID NO 3
<211> LENGTH: 23
<212> TYPE: RNA
<213> ORGANISM: Artificial Sequence
<220> FEATURE:
<223> OTHER INFORMATION: miR-155 human

<400> SEQUENCE: 3
uuaaugcuaa ucgugauagg ggu                                                23

<210> SEQ ID NO 4
<211> LENGTH: 21
<212> TYPE: RNA
<213> ORGANISM: Artificial Sequence
<220> FEATURE:
<223> OTHER INFORMATION: Hsa-miR-721

<400> SEQUENCE: 4
ucuugcaauu aaaaggggga a                                                  21

<210> SEQ ID NO 5
<211> LENGTH: 18
<212> TYPE: PRT
<213> ORGANISM: Artificial Sequence
<220> FEATURE:
```

```
<223> OTHER INFORMATION: MyHC-alpha peptide with N-terminal acetylation
<220> FEATURE:
<221> NAME/KEY: ACETYLATION
<222> LOCATION: 1

<400> SEQUENCE: 5
```

Arg Ser Leu Lys Leu Met Ala Thr Leu Phe Ser Thr Tyr Ala Ser Ala
1               5                   10                  15

Asp Arg

```
<210> SEQ ID NO 6
<211> LENGTH: 82
<212> TYPE: RNA
<213> ORGANISM: Artificial Sequence
<220> FEATURE:
<223> OTHER INFORMATION: mmu130b

<400> SEQUENCE: 6
ggcuguuugg acacucuuuc ccuguugcac uacuguggc cucugggaag cagugcaaug    60
augaaagggc aucugucggg cc                                           82

<210> SEQ ID NO 7
<211> LENGTH: 97
<212> TYPE: RNA
<213> ORGANISM: Artificial Sequence
<220> FEATURE:
<223> OTHER INFORMATION: Mmu301b

<400> SEQUENCE: 7
uuuccugcug gcugcgggug cucugacuag guugcacuac ugucuguga aagcagugc    60 aauguauug ucaaagcauc ugggaccagc cucgaag                            97

<210> SEQ ID NO 8
<211> LENGTH: 88
<212> TYPE: RNA
<213> ORGANISM: Artificial Sequence
<220> FEATURE:
<223> OTHER INFORMATION: mmu721

<400> SEQUENCE: 8
ggaagacagu gcaauuaaaa gggggaaaaa aguaccuggg auguucugag aauuucauuu   60
uucuuguuau ugccacuccu gcuuggaa                                     88

<210> SEQ ID NO 9
<211> LENGTH: 421
<212> TYPE: DNA
<213> ORGANISM: Artificial Sequence
<220> FEATURE:
<223> OTHER INFORMATION: Mir 721 clon100

<400> SEQUENCE: 9
gcagctccta gactgttctg cgagcatagc tccttctcct ccttatccct gacctggatc    60
aagctcagat tgtccttctg tataaaggat gttgtgggca tagtgctcat ttctctcaat   120
ccactagcct gaagacatgg agggcagaga gagattcagg tttcctggga agacagtgca   180
attaaagggg ggaaaaaagt acctgggatg ttctgagaat tcatttttc ttgttattgc    240 cactcctgct tggaagaact atgttcccaa aatagctcta gcaatctagc ataacataaa   300
tattttaatg ctgattaaaa taataatgaa aagtcatgaa tgagaaaggg actgtgtata   360
gaggccgcat aagtgcccac caagcctgag agtcacatga tggacagtgt tggtgttaag   420
c                                                                  421
```

```
<210> SEQ ID NO 10
<211> LENGTH: 26
<212> TYPE: DNA
<213> ORGANISM: Artificial Sequence
<220> FEATURE:
<223> OTHER INFORMATION: Mi721 fw

<400> SEQUENCE: 10
atatctcgag attgtccttc tgtata                                          26

<210> SEQ ID NO 11
<211> LENGTH: 26
<212> TYPE: DNA
<213> ORGANISM: Artificial Sequence
<220> FEATURE:
<223> OTHER INFORMATION: Mi721 rev

<400> SEQUENCE: 11
tcagtactta ctctttgaat tctata                                          26

<210> SEQ ID NO 12
<211> LENGTH: 104
<212> TYPE: DNA
<213> ORGANISM: Artificial Sequence
<220> FEATURE:
<223> OTHER INFORMATION: 721spacer fw

<400> SEQUENCE: 12
aattcttccc ccttttaatt gcactgcgat ttcccccttt taattgcact gaccggtttc     60 cccctttta ttgcactgtc acttcccct tttaattgca ctgg                        104

<210> SEQ ID NO 13
<211> LENGTH: 104
<212> TYPE: DNA
<213> ORGANISM: Artificial Sequence
<220> FEATURE:
<223> OTHER INFORMATION: 721spacer rev

<400> SEQUENCE: 13
gatcccagtg caattaaaag ggggaagtga cagtgcaatt aaaaggggga aaccggtcag     60
tgcaattaaa aggggggaaat cgcagtgcaa ttaaaagggg gaag                    104

<210> SEQ ID NO 14
<211> LENGTH: 51
<212> TYPE: DNA
<213> ORGANISM: Artificial Sequence
<220> FEATURE:
<223> OTHER INFORMATION: Vector with restriction sites

<400> SEQUENCE: 14
attctagagc tagcgaattc gaatttaaat cggatccgcg gccgcgaagg a              51

<210> SEQ ID NO 15
<211> LENGTH: 51
<212> TYPE: DNA
<213> ORGANISM: Artificial Sequence
<220> FEATURE:
<223> OTHER INFORMATION: Vector with restriction sites

<400> SEQUENCE: 15
tccttcgcgg ccgcggatcc gatttaaatt cgaattcgct agctctagaa t              51

<210> SEQ ID NO 16
```

```
<211> LENGTH: 19
<212> TYPE: DNA
<213> ORGANISM: Artificial Sequence
<220> FEATURE:
<223> OTHER INFORMATION: Open vector

<400> SEQUENCE: 16
gatccgcggc cgcgaagga                                                  19

<210> SEQ ID NO 17
<211> LENGTH: 15
<212> TYPE: DNA
<213> ORGANISM: Artificial Sequence
<220> FEATURE:
<223> OTHER INFORMATION: Open vector

<400> SEQUENCE: 17
attctagagc tagcg                                                      15

<210> SEQ ID NO 18
<211> LENGTH: 15
<212> TYPE: DNA
<213> ORGANISM: Artificial Sequence
<220> FEATURE:
<223> OTHER INFORMATION: Open vector

<400> SEQUENCE: 18
tccttcgcgg ccgcg                                                      15

<210> SEQ ID NO 19
<211> LENGTH: 19
<212> TYPE: DNA
<213> ORGANISM: Artificial Sequence
<220> FEATURE:
<223> OTHER INFORMATION: Open vector

<400> SEQUENCE: 19
aattcgctag ctctacaat                                                  19

<210> SEQ ID NO 20
<211> LENGTH: 104
<212> TYPE: DNA
<213> ORGANISM: Artificial Sequence
<220> FEATURE:
<223> OTHER INFORMATION: Insert

<400> SEQUENCE: 20
aattcttccc cctttaatt gcactgcgat ttccccttt taattgcact gaccggtttc       60 cccctttaa ttgcactgtc acttcccct tttaattgca ctgg                      104

<210> SEQ ID NO 21
<211> LENGTH: 104
<212> TYPE: DNA
<213> ORGANISM: Artificial Sequence
<220> FEATURE:
<223> OTHER INFORMATION: Insert

<400> SEQUENCE: 21
gatcccagtg caattaaaag ggggaagtga cagtgcaatt aaaaggggga aaccggtcag     60
tgcaattaaa aggggaaat cgcagtgcaa ttaaaagggg gaag                     104

<210> SEQ ID NO 22
<211> LENGTH: 18
<212> TYPE: RNA
<213> ORGANISM: Artificial Sequence
```

```
<220> FEATURE:
<223> OTHER INFORMATION: mmu-130b -5P

<400> SEQUENCE: 22 cucuuuccccu guugcacu                                                   18

<210> SEQ ID NO 23
<211> LENGTH: 19
<212> TYPE: RNA
<213> ORGANISM: Artificial Sequence
<220> FEATURE:
<223> OTHER INFORMATION: mmu-301b -5P

<400> SEQUENCE: 23
gcucugacua gguugcacu                                                   19

<210> SEQ ID NO 24
<211> LENGTH: 20
<212> TYPE: RNA
<213> ORGANISM: Artificial Sequence
<220> FEATURE:
<223> OTHER INFORMATION: mmu-721

<400> SEQUENCE: 24
uuuuucuugu uauugccacu                                                  20

<210> SEQ ID NO 25
<211> LENGTH: 59
<212> TYPE: DNA
<213> ORGANISM: Artificial Sequence
<220> FEATURE:
<223> OTHER INFORMATION: 3 prime UTR MEOX2 sequence

<400> SEQUENCE: 25
agagagggag atggatgttt gctttggctt gcactgaaaa ttaaatttgc taccaagag       59

<210> SEQ ID NO 26
<211> LENGTH: 22
<212> TYPE: RNA
<213> ORGANISM: Artificial Sequence
<220> FEATURE:
<223> OTHER INFORMATION: miR-130b

<400> SEQUENCE: 26
cagugcaaug augaaagggc au                                               22

<210> SEQ ID NO 27
<211> LENGTH: 23
<212> TYPE: RNA
<213> ORGANISM: Artificial Sequence
<220> FEATURE:
<223> OTHER INFORMATION: miR-301b

<400> SEQUENCE: 27
cagugcaaug guauugucaa agc                                              23

<210> SEQ ID NO 28
<211> LENGTH: 21
<212> TYPE: RNA
<213> ORGANISM: Artificial Sequence
<220> FEATURE:
<223> OTHER INFORMATION: miR-721

<400> SEQUENCE: 28
cagugcaauu aaaaggggga a                                                21
```

```
<210> SEQ ID NO 29
<211> LENGTH: 44
<212> TYPE: DNA
<213> ORGANISM: Artificial Sequence
<220> FEATURE:
<223> OTHER INFORMATION: 3 prime UTR CD69 sequence

<400> SEQUENCE: 29
tttcaaagtg ctggaaagaa aagtgcaata cgtgtagtgg caga           44

<210> SEQ ID NO 30
<211> LENGTH: 71
<212> TYPE: DNA
<213> ORGANISM: Artificial Sequence
<220> FEATURE:
<223> OTHER INFORMATION: 3 prime UTR AHR sequence

<400> SEQUENCE: 30
agaatagttc ttacctcata tgcatttttt cagtgtatct tgtaaagaaa tcaagtagta   60
aattgaagct t                                                       71

<210> SEQ ID NO 31
<211> LENGTH: 88
<212> TYPE: RNA
<213> ORGANISM: Artificial Sequence
<220> FEATURE:
<223> OTHER INFORMATION: Mus musculus_Mmu721

<400> SEQUENCE: 31
ggaagacagu gcaauuaaaa gggggaaaaa aguaccuggg auguucugag aauuucauuu   60
uucuuguuau ugccacuccu gcuuggaa                                     88

<210> SEQ ID NO 32
<211> LENGTH: 86
<212> TYPE: RNA
<213> ORGANISM: Artificial Sequence
<220> FEATURE:
<223> OTHER INFORMATION: Rhesus macaca_Rma721

<400> SEQUENCE: 32
aaauaucagu gcaauuaaaa ggaggaaaac aauaaacaga aucagcaaaa ucaaaagauc   60
aagaaaauug auaaaccucu agccaa                                       86

<210> SEQ ID NO 33
<211> LENGTH: 86
<212> TYPE: RNA
<213> ORGANISM: Artificial Sequence
<220> FEATURE:
<223> OTHER INFORMATION: Homo sapiens_Hsa721

<400> SEQUENCE: 33
cugcuuucuu gcaauuaaaa gggggaaaaa gugcuagggg cacauugcac uacauccuag   60
agccugacgu uagaaaacau guauug                                       86

<210> SEQ ID NO 34
<211> LENGTH: 21
<212> TYPE: RNA
<213> ORGANISM: Artificial Sequence
<220> FEATURE:
<223> OTHER INFORMATION: Predictive hsa 721

<400> SEQUENCE: 34
ucuugcaauu aaaggggga a                                             21
```

<210> SEQ ID NO 35
<211> LENGTH: 38
<212> TYPE: DNA
<213> ORGANISM: Artificial Sequence
<220> FEATURE:
<223> OTHER INFORMATION: 3 prime UTR CD69 sequence

<400> SEQUENCE: 35
aggaatattt gcaagacata gaatagtgtt ggaaaatg               38

<210> SEQ ID NO 36
<211> LENGTH: 40
<212> TYPE: DNA
<213> ORGANISM: Artificial Sequence
<220> FEATURE:
<223> OTHER INFORMATION: 3 prime UTR CD69 sequence

<400> SEQUENCE: 36
ttcatgcatt tgcactactg gaaggagtta gatgttggta             40

<210> SEQ ID NO 37
<211> LENGTH: 43
<212> TYPE: DNA
<213> ORGANISM: Artificial Sequence
<220> FEATURE:
<223> OTHER INFORMATION: 3 prime UTR AHR sequence

<400> SEQUENCE: 37
gtaagatatt tgcagttttt cattttaaaa agtccatacc tta         43

<210> SEQ ID NO 38
<211> LENGTH: 39
<212> TYPE: DNA
<213> ORGANISM: Artificial Sequence
<220> FEATURE:
<223> OTHER INFORMATION: 3 prime UTR AHR sequence

<400> SEQUENCE: 38
aatcggaggt tgcagagcca agatcgcccc actgcactc              39

<210> SEQ ID NO 39
<211> LENGTH: 40
<212> TYPE: DNA
<213> ORGANISM: Artificial Sequence
<220> FEATURE:
<223> OTHER INFORMATION: 3 prime UTR Meox2 sequence

<400> SEQUENCE: 39
tgcttttgct tgcactgaaa attaaattgc tatcaagaat             40

<210> SEQ ID NO 40
<211> LENGTH: 36
<212> TYPE: DNA
<213> ORGANISM: Artificial Sequence
<220> FEATURE:
<223> OTHER INFORMATION: 3 prime UTR Meox2 sequence

<400> SEQUENCE: 40
cagttacctt gcagaaagag ctttgtatga cagaca                 36

METHOD FOR DIAGNOSING CARDIOMYOPATHIES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200278_401USPC_SEQUENCE_LISTING.txt. The text file is 8.95 KB, was created on May 31, 2018, and is being submitted electronically via EFS-Web.

BACKGROUND OF THE INVENTION

Inflammation of the myocardium or myocarditis is a disease with heterogeneous etiology, oftenly caused by an infectious pathogen (bacteria, virus, fungi or protozoa) (Andreoletti et al., 2009) or by an autoimmune disorder (Frustaci et al., 2009), which can result in dilated cardiomyopathy (Felker et al., 2000). T $CD4^+$ cells are necessary and sufficient for the development of myocarditis (Smith and Allen, 1991; Smith and Allen, 1993). Specifically, $T_H17$ lymphocytes (Sonderegger et al., 2006) and IL-23 cytokine are critical for the development of the pathology, being $T_H17$ cells more immunopathogenic than $T_H1$ cells when they are exogenously transferred (Rangachari et al., 2006). Furthermore, suppression of $T_H17$ cell differentiation through the blocking of the IL-6 signaling pathway prevents the development of EAM (Experimental Autoimmune Myocarditis) (Sonderegger et al., 2008; Yamashita et al., 2011). With respect to IL-17, it has been observed that this cytokine does not participate in the initial development of myocarditis but it plays a crucial role in fibrosis and the remodeling that the heart experiences in more advanced stages of the disease (Baldeviano et al., 2010). In humans, the clinical relevance of $T_H17$ cells is close to being verified, and in fact, in patients with viral myocarditis IL-17A and RORγt expression in the heart has already been detected and it has been observed that $T_H17$ cells help B cells produce antibodies against cardiac proteins (Yuan et al., 2010). However, little research has been conducted concerning $T_H17$ cells circulating in the blood of patients with myocarditis. Only one study is known in which the proportion of $T_H17$ lymphocytes in the blood of patients with dilated cardiomyopathy was compared to that of healthy subjects, there being a higher percentage of $T_H17$ cells and a larger number of IL-17, IL-6, IL-23 and RORγt cells in the blood of sick subjects with respect to the blood of healthy individuals (Yi et al., 2009).

Regulatory T cells are another population of T $CD4^+$ cells that are crucial in the development of myocarditis. FoxP3 expression has been detected in endocardium biopsies of patients with dilated cardiomyopathy (Noutsias et al., 2011). Furthermore, the depletion of Treg cells allows the spontaneous development of myocarditis (Ono et al., 2006), whereas the exogenous transfer of Treg cells limits cardiac inflammation and attenuates viral replication in response to infection with CVB3 or *Trypanosoma cruzi* (Mariano et al., 2008; Shi et al., 2010). Treg cells are also responsible for inducing tolerance by nasal route against autoantigens, which prevents CVB3 infection from progressing to chronic myocarditis (Fousteri et al., 2011). Similarly, IL-10 cytokine limits autoimmune inflammation of the heart by means of tolerance induced by nasal route (Kaya et al., 2002). However, there is a substantial discrepancy with respect to the predictive value of the proportion of Treg lymphocytes circulating in blood in patients with acute and chronic heart pathologies (Ammirati et al., 2010; Carvalheiro et al., 2012; Sardella et al., 2007).

Recent studies estimate the prevalence of myocarditis in about. 22 of 100.000 patients annually (International Classification of Diseases, WHO), and the American Heart Association and American College of Cardiology Rank myocarditis as the third leading cause of sudden cardiac death in professional athletes. Moreover, between 1-5% of patients with acute viral infection develop myocarditis. The diagnosis of myocarditis made based on clinical, laboratory, ECG, and Echo findings is not always easy. Moreover, a safe and sensitive non-invasive diagnostic test to confirm the diagnosis of acute myocarditis, compared to other pathologies with myocardial injury like acute coronary disease, is not available nowadays. Endomyocardial biopsy (EMB) is still considered the gold standard diagnosis of myocarditis. However, EMB is not commonly performed due to safety reasons; 6% of wide range complications and 0.4 incidence of death due to perforation.

Acute myocarditis resolves in about 50% of cases in the first weeks, however 25% develop persistent heart failure that can progress to end-stage dilated cardiomyopathy and heart transplantation. Therefore, early diagnosis of the disease is vital for the specific treatment of the patient (antiviral, immunosuppressive, heart failure therapies, etc) to avoid the subsequent development of the disease. However, most acute myocarditis patients have common symptoms with Acute Myocardial Infartion patients (AMI). It is thus necessary to provide tools in clinical practice for the differential diagnosis of acute myocarditis and AMI since acute myocarditis often simulates a myocardial infarction and differential diagnosis is many times difficult as intramyocardial biopsy is not a routine diagnostic technique. This often makes these patients undergo coronary angiography and MRI with contrast to rule out ischemia, with consequent damage to the patient, delay in the election of immunosuppressive treatment of choice and high medical expenses associated with coronary angiography and MRI as the only reliable methods for distinguishing these Myocarditis from AMI. Myocarditis is therefore a diagnostic challenge that does not have a solution in clinical practice.

The present invention solves this problem by providing an assay capable of assuring an acceptable degree of specificity and sensitivity for diagnosing myocarditis, during an acute episode, by using blood samples, particularly plasma or serum samples.

BRIEF DESCRIPTION OF THE INVENTION

The present invention provides an in vitro method for diagnosing a cardiomyopathy in a human subject, wherein the method comprises using, as an indicator, the expression levels, obtained from a biological sample isolated from the human subject, preferably a blood, plasma or serum sample, of one or more of the following miRNAs: miR-721 and/or miR155, and obtaining a result of the method by comparing the expression levels of said one or more miRNAs with a reference value or with the expression levels of a control, indicator of the absence of cardiomyopathy.

More particularly, the present invention provides an in vitro method for diagnosing Myocarditis during an acute episode. Myocarditis is a Th17-mediated disease characterized by the presence of immune infiltrates that triggers cardiomyocyte necrosis and fibrosis of the heart and, therefore, progressive heart dysfunction. It shares common symptoms with acute myocardial infarction so it is important to find biomarkers for the specific differential diagnosis of myocarditis, preferably during the acute episode, from acute myocardial infarction. MiR-721, found overexpressed in exacerbated Experimental Autoimmune Myocarditis (EAM) mouse model and Th17 cells, is shown herein as an excellent target for such differential diagnosis. In this sense, we found miR-721 overexpressed in the serum, draining lymph nodes and isolated Th17 cells from EAM mice. Furthermore, we were able to detect miR-721 in the serum of EAM but not in basal conditions. Since we found Th17 and miR-721 upregulated in myocarditis patients and no Th17 response in acute myocardial infarction patients, we estimate miR-721 to be a powerful diagnostic tool to distinguish between both pathologies.

BRIEF DESCRIPTION OF THE DRAWINGS

FIG. 2 shows the sequence and secondary structure of miRNA-721. Data obtained from miR Base.

FIG. 3 shows an example of the miR-721 cloning strategy. Oligos containing the flanking sequences of immature miR-721 were designed, such that was cloned a fragment of about 100 base pairs flanking the mature miR-721 sequence.

FIG. 4 shows the design of the miR-721 sponge sequence for cloning into lentiviral vector pCDH-CMV-MCS-EF1-copGFP. The complementary sequence of miR-721 is shown in pink and spacers are shown in blue.

FIG. 8 shows the alignment of complementary sequences between the family miR-130/301/721 and the 3"UTR end of Meox-2 gene.

FIG. 9 shows the alignment of complementary sequences between the family miR-130/301/721 and the 3"UTR end of CD69 and AHR genes.

FIG. 11 shows representative images of MLECs from CD69WT and CD69KO mice infected with control LV, sponge-miR-721 LV that are unstimulated (A) or stimulated with PMA/ionomycin (B). The efficiency of infection (>90% GFP+ cells) and the acquisition of cells of the proangiogenic phenotype after stimulation are observed.

FIG. 13 shows multiple species sequence alignment of the miR-721 including the predictive Human (*Homo sapiens*) and Monkey (*Rhesus macaca*) sequences. Red box contains the 21 nucleotides from the mature sequences of miR-721 from each specie. Green nucleotides correspond to the predictive loop nucleotides involved in the formation of the secondary structure of the miRNA (A). FIG. 13B shows the alignment of complementary sequences between the human hsa-miR-721 and the 3'UTR end of CD69, AHR and Meox2 genes (B).

FIG. 25 shows that CD69KO mice present exacerbated inflammation in the myocardium during the acute phase of EAM. (a) Shows the image taken by fluorescence molecular tomography, showing neutrophil infiltration into the myocardium of WT and CD69KO mice subcutaneously immunized with CFA/MyHCα or CFA/PBS in the case of controls. (b) Shows the intensity of the ProSense 750 FAST probe (detecting activated elastase) measured by means of fluorescence molecular tomography in WT and CD69KO mice during the acute phase of EAM. It is an experiment representative of a total of 3 independent experiments (n=6 mice per group) ($*P<0.05$, One-way analysis of variance (ANOVA).

FIG. 26 shows the of experimental autoimmune myocarditis (EAM) model. The EAM mouse model is induced by means of immunization of a peptide derived from the α-myosin heavy chain (MyHCα) emulsified with CFA (Complete Freund's Adjuvant) on days 0 and 7. After 21 days, the mice are in the acute phase of the disease, at which time the animals were sacrificed and their hearts were extracted to study the expression of the miRNAs present therein.

FIG. 32 shows the miRNA expression levels in the blood plasma of patients with myocarditis and dilated cardiomyopathies. miR-155 and miR-721 relative expression in the blood plasma of healthy subjects and patients with acute myocarditis, chronic myocarditis and Takotsubo syndrome was measured by qPCR. The error bars represent the mean±SD (One-way analysis of variance (ANOVA)).

DETAILED DESCRIPTION OF THE INVENTION

Figure 1:
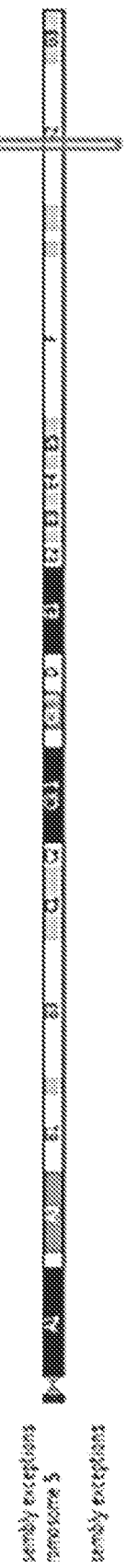
FIG. 1 shows the sequence complementarity of the family of miRNAs 130/301/721 and the chromosomal location thereof.

In the present invention, based on the determination that mice with myocarditis present miR-721 and miR-155 expression levels in blood serum much higher than those of control mice, the expression of these miRNAs in the plasma of patients with different cardiomyopathies was analyzed. The result was an extraordinary increase in miR-721 and miR-155 expression in the plasma of patients with acute myocarditis compared to healthy subjects. Patients in the chronic phase of the disease also presented expression levels of these miRNAs that were much higher than those of healthy volunteers, but not as high as during the acute phase. Furthermore, with respect to Takotsubo cardiomyopathy, the spectacular increase in miR-721 and miR-155 expression in the blood of patients with this syndrome compared to control subjects is striking. These results point out the possible role of these miRNAs in the pathophysiology of myocarditis, preferably during the acute episode, and dilated cardiomyopathy. In this sense and based on these results, the present invention provides a novel strategy for the diagnosis of myocarditis, in particular during the acute episode, based on the determination of miR-721 and/or miR-155 in blood, serum or plasma samples.

In addition, it is noted that when a patient reaches the hospital with a pain in the chest it is often difficult to distinguish between acute myocardial infarction (AMI) and myocarditis because these two pathologies share most symptoms such as arrhythmias, elevation of the ST segment, circulating troponin levels or C-reactive protein (Fung et al, 2016) etc. . . . . Therefore, clinicians routinely proceed with invasive techniques to treat AMI since this disease is more harmful. However, the autoimmune phenotype characterized by a high CD4+ T cells and Treg/Th17 levels in myocarditis patients is not observed in AMI patients. In addition, recent results from our laboratory showed that miR-721 is not expressed in the serum of mouse models for myocardial infarction right after the episode, but only around two weeks later, matching the Th17 response peak developed post-infarction to solve the injury. Since miR-721 is highly upregulated in acute and chronic myocarditis patients when they come to the hospital, it is a powerful biomarker for myocarditis. Therefore, the non-invasive strategy proposed in the present invention is a fast and efficient approach to clarify the diagnosis between these two cardiovascular events.

Furthermore, the extraordinary increase in miR-721 expression in the plasma of patients with acute myocarditis compared to healthy subjects is due to the fact that miR-721 is significantly present in the exosomes of Th17 cells. To our knowledge, this is the first time that it is described that MiR-721 is upregulated in the exosomes from Th17 in diseases characterized by an exacerbated Th17 response (see examples 5.1 or 5.2) such as myocarditis, in particular during the acute episode. Such extraordinary increase due to its increased localization in the exosomes facilitates the detection of such biomarker (miR-721) in non invasive samples such as blood, serum or plasma biological samples and thus the diagnosis of diseases such as acute myocarditis in human subjects.

Hence, a first aspect of the invention refers to an in vitro method for obtaining data useful for diagnosing a cardiomyopathy in a human subject, preferably for the detection or diagnosis of a cardiomyopathy in a human subject, wherein the method comprises using, as an indicator, the expression levels, obtained from a biological sample isolated from the human subject, of one or more of the following miRNAs: miR-721 and/or miR155, and obtaining a result of the method by comparing the expression levels of said one or more miRNAs with a reference value or with the expression levels of a control, indicator of the absence of such cardiomyopathy.

In the present invention, SEQ ID NO 1 is understood as CAGUGCAAUUAAAAGGGGGAA (murine miR-721 sequence). Variations of said sequence associated with the different miR-721 sequences in different species are included in this definition, such as the miR-721 sequence in humans which is UCUUGCAAUUAAAAGGGGGAA illustrated herein as SEQ ID NO 4. Hsa-miR-721 is located within the region: NCBI Reference Sequence: NC_000008.11 (REGION: 95353371 . . . 95353588).

In the article Wheeler G. et al., FEBS Letters 2006, where the mouse miR-721 was identified, it is stated that no homologous sequences were found in human genome. However, a 21 nucleotides region of the mouse precursor is conserved in the monkey and human genome (see FIG. 13). The 5' 18 nucleotides of the 21 nucleotides human match were identical to the last 18 nucleotides of the cloned mouse miRNA and the last 3 nucleotides of the 21 nucleotides human match were also identical to the mouse genome sequence following the cloned miRNA sequence. The predictive human miR-721 was located at the chromosome 8, GRCh38.p7. The predictive human hsa-miR-721 is detected with mouse probes for Mmu-miR-721.

In the present invention, SEQ ID NO 2 is understood as UUAAUGCUAAUUGUGAUAGGGGU (miR-155 murine) and SEQ ID NO 3 is understood as UUAAUGCUAAUCGUGAUAGGGGU (miR-155 human).

In a preferred embodiment of the first aspect of the invention, illustrative non-limiting examples of said biological samples include different types of tissue samples, as well as samples of biological fluids, such as blood, serum, plasma, cerebrospinal fluid, peritoneal fluid, and feces. Preferably, said samples are blood, serum or plasma biological samples.

In another preferred embodiment of the first aspect of the invention, the cardiomyopathy is myocarditis, Takotsubo syndrome, dilated cardiopathy, peripheral ischemia or Chagas. More preferably, the cardiomyopathy is acute myocarditis.

Another preferred embodiment of the first aspect of the invention or any of its preferred embodiments, uses, as an indicator, the expression levels of one or more miRNAs such as those defined in SEQ ID NOs: 3 or 4 above, and wherein the result is an indicator of the existence of a myocarditis, preferably an acute myocarditis, or of Takotsubo syndrome if:

(i) the miRNA levels as defined in SEQ ID NO: 3 have increased with respect to a reference value or with respect to the expression levels of a control, indicator of the absence of the disease; and/or (ii) the miRNA levels as defined in SEQ ID NO: 4 have increased with respect to a reference value or with respect to the expression levels of a control, indicator of the absence of the disease.

In another preferred embodiment of the first aspect of the invention or of any of its preferred embodiments, the biological sample is selected from the group consisting of blood, serum or plasma and such biological sample is treated with a lysis agent such as a detergent composition or chaotropic agents and/or physical lysis (e.g. Ultrasounds, vigorous shaking), capable of disrupting the membrane of the exosomes so that such exosomes, in particular exosomes from Th17 cells, liberate their content to the exterior and thus liberate miRNAs such as miR-721.

In this sense it is noted that collection and handling procedures of blood, serum or plasma needs to be greatly improved for miRNA analysis in order to reliably detect differences between healthy and disease patients. Furthermore, ribonucleases present in blood can degrade free RNA upon collection rendering extracellular miRNA at risk of degradation. These factors have consequently decreased sensitivity and specificity of miRNA biomarker assays. miRNAs secreted from blood cells into exosomes are protected from degradation and have increased potential as biomarkers. To improve the use of miRNAs as biomarkers, exosomes have to be either isolated from blood, serum or plasma by different methods and then miRNAs need to be released from the inside with a lysis agent to disrupt the membrane of the exosomes or simply disrupted without previously isolating them so that they liberate their content to the exterior and thus liberate miRNAs such as miR-721 in the sample (examples of lysis agents useful in the present invention are shown in table 1 below). In any case, the fact that this is the first time that it is described that miR-721 is upregulated in the exosomes from Th17 cells in the blood, serum or plasma samples of patients suffering from acute myocarditis, unveils the use of miR-721 in these samples as a most value tool to reliably detect differences between healthy and disease patients.

TABLE 1

| Chaotropic agent | Chemical formula | Molar mass | Density | Solubility | Application |
|---|---|---|---|---|---|
| Guanidinium chloride | $CH_6ClN_3$ | 95.53 g · mol$^{-1}$ | 1.354 g/cm$^3$ at 20° C. | very soluble in water and ethanol | Denaturing agent |
| Urea | $CH_4N_2O$ | 60.06 g · mol$^{-1}$ | 1.32 g/cm$^3$ | Solubility in water | Denaturing agent |
| Thiourea | $CH_4N_2S$ | 76.12 g/mol | 1.405 g/ml | Solubility in water | Denaturing agent |
| Phenol | $C_6H_6O$ | 94.11 g · mol$^{-1}$ | 1.07 g/cm$^3$ | Solubility in water | Denaturing agent |

| Detergent | CMC | MMW | MMr | Working concentration | Easy of removal | Application |
|---|---|---|---|---|---|---|
| Anionic | | | | | | |
| SDS(Sodium docecyl sulfate) | 8.3 | 288.4 | 18,000 | ≥10 mg per mg prot. | NO | Denaturing proteins |
| DOC (Deoxycholic acid) | 1-4 | 416.6 | 4,200 | 0.1-10 mg | | Solubilization of membrane proteins |
| Zwitterionic | | | | | | |
| CHAPS (3(3Cholamido propyl dimethylammonio)1 propane sulfonate Noninonic | 4 | 614.9 | 6,150 | 6.5-13 mM | YES | Solubilization of membrane proteins |
| Nonidet p-40 (Ethylphenolpoly (ethyleneglycolether)n) | 0.25 | 606.6 n = 11 | 90,000 | 1-10 mM | NO | Protein solubilization |
| n-Octylglucoside | 14.5 | 292.4 | | 46 mM | YES | Mild non denaturing detergent for membrane solubilization |
| Sucrose monolaurate | 0.2 | 524.6 | | 0.2%-5%(w/v) | NO | Gentle solubilization/ stabilization membrane proteins. |
| Triton X100 (Octylphenolpoly (ethyleneglycolether)n) | 0.2 | 647.10 n = 10 | 90,000 | 13.5 | NO | Solubilitation/ denaturing proteins. |
| Tween 20 (Poly(oxyethylene)n sorbitan monolaurate) | 0.06 | 1228 n = 20 | | ≥10 mg/mg membrane lipid | NO | Non denaturing detergent. |

In the context of the present invention, the term "detergent composition" is understood as a composition comprising amphipathic molecules (containing both polar hydrophilic heads and non-polar hydrophobic tails) that enables disruption and formation of hydrophobic-hydrophilic interactions among molecules. In biological research, detergents such as oxyethylene, tert-octylphenol or ethyleneglycoether polymers are used to solubilize cell-derived membranes such as plasmatic membranes, organelles membranes or extracellular exosomes in order to allow the release of their content. To not interfere with soluble proteins n-Octylglucoside or other mild non-denaturing detergent for the solubilization of proteins can be used.

In another preferred embodiment of the first aspect of the invention or of any of its preferred embodiments, the biological sample is selected from the group consisting of blood, serum or plasma and such biological sample is treated so that the exosomal fraction of the Th17 cells is obtained and the determination of the expression levels of miR-721 is performed in such exosomal fraction by using a lysis agent, such as a detergent composition or chaotropic agents and/or physical lysis (e.g. Ultrasounds, vigorous shaking), capable of disrupting the membrane of the exosomes so that such exosomes, in particular exosomes from Th17 cells, so that such exosomes liberate their content to the exterior and thus liberate miRNAs such as miR-721.

Exosomes are extracellular cell-derived vesicles with a diameter ranging from 30 to 300 nm present in biological fluids and cultured media of cell cultures. They contain proteins, metabolites and nucleic acids such as mRNA and non-coding RNAs coated in a lipid bilayer membrane. The exosomal fraction corresponds to all the exosomes of a particular biological sample or cell culture medium.

In the context of the present invention, the exosomal fraction from Th17 cells can be obtained from any known technique to the skilled person. For example, cell suspensions from lymph nodes 6 days after EAM induction were cultured ($2 \times 10^7$ cells/ml) during 48 h in exosome-free TexMACS media (Miltenyl Biotech) with MyHC peptide (10 ug/ml) and IL-23 (10 ng/ml). Afterwards, sorting for IL-17eGFP using the BD FACs Aria II cell sorter/iCyt Synergy 4L cell sorter. Sorted cells were cultured again in TexMACS media with MyHC peptide and IL-23 for IL-17+ cells (Th17) expansion. Supernatants from post-sorted Th17 were collected after 48 h. Briefly, rest of cells were pelleted (2000 rpm for 10 min). For exosomes isolation culture supernatants were precipitated by adding 0.4 volumes of 50% Polyethylene glycol 6000 (Sigma Aldrich) in 375 mM NaCl to the samples, storing 30 min at 4° C. and centrifugation 1500 g at 4° C. In another preferred embodiment of the first aspect of the invention or of any of its preferred embodiments, the result can be obtained by means of:
  (i) a gene profiling method, such as a microarray; and/or
  (ii) a method comprising PCR, such as real time PCR; and/or
  (iii) Northern blot.

Preferably, the result is obtained by means of real time quantitative PCR.

In another preferred embodiment of the first aspect of the invention or any of its preferred embodiments, the method is carried out in vitro using a sample from the human subject, and wherein at the time of taking the sample from the human subject, the human subject is not being treated for cardiomyopathy.

In another preferred embodiment of the first aspect of the invention or any of its preferred embodiments, miRNA expression is normalized.

A second aspect of the invention relates to a method for classifying a human subject into one of two groups, wherein group 1 comprises the subjects that can be identified by means of the method according to the first aspect of the invention, and wherein group 2 represents the remaining subjects.

A third aspect of the invention relates to a pharmaceutical composition comprising a therapeutic agent suitable for treating a human subject from group 1 that can be identified by means of the method of claim 11.

A fourth aspect of the invention refers to a method for the differential diagnosis of acute myocardial infarction from acute myocarditis in a human subject suspected of suffering from any of these pathologies, wherein the method comprises using, as an indicator, the expression levels, obtained from a biological sample isolated from the human subject, of miR-721, and obtaining a result of the method by comparing the expression levels of said miRNA with a reference value or with the expression levels of a control, wherein an increased expression of miR-721 is indicative of acute myocarditis and the absence of expression is indicative of acute myocardial infarction.

In a preferred embodiment of the fourth aspect of the invention, illustrative non-limiting examples of said samples include different types of tissue samples, as well as samples of biological fluids, such as blood, serum, plasma, cerebrospinal fluid, peritoneal fluid, and feces.

Preferably, said samples are blood, serum or plasma biological samples.

In another preferred embodiment of the fourth aspect of the invention or of any of its preferred embodiments, the biological sample is selected from the group consisting of blood, serum or plasma and such biological sample is treated with a lysis agent such as a detergent composition or chaotropic agents and/or physical lysis (e.g. Ultrasounds, vigorous shaking), capable of disrupting the membrane of the exosomes so that such exosomes, in particular exosomes from Th17 cells, liberate their content to the exterior and thus liberate miRNAs such as miR-721.

In another preferred embodiment of the fourth aspect of the invention or of any of its preferred embodiments, the biological sample is selected from the group consisting of blood, serum or plasma and such biological sample is treated so that the exosomal fraction of the Th17 cells is obtained and the determination of the expression levels of miR-721 is performed in such exosomal fraction by using a lysis agent, such as a detergent composition or chaotropic agents and/or physical lysis (e.g. Ultrasounds, vigorous shaking), capable of disrupting the membrane of the exosomes, so that such exosomes liberate their content to the exterior and thus liberate miRNAs such as miR-721.

In another preferred embodiment of the fourth aspect of the invention or of any of its preferred embodiments, the result can be obtained by means of:
  (i) a gene profiling method, such as a microarray; and/or
  (ii) a method comprising PCR, such as real time PCR; and/or
  (iii) Northern blot.

Preferably, the result is obtained by means of real time quantitative PCR.

In another preferred embodiment of the fourth aspect of the invention or any of its preferred embodiments, miRNA expression is normalized.

A fifth aspect of the invention refers to a method of treatment of a human subject suspected of suffering from acute myocardial infarction or from acute myocarditis, wherein said method comprises performing the differential diagnosis according to the fourth aspect of the invention or according to any of its preferred embodiments, wherein if there is an increased expression of miR-721 in the biological sample, the patient is treated for acute myocarditis and wherein if there is an absence of expression of miR-721 in the biological sample, the patient is treated for acute myocardial infarction.

In the context of the present invention, suitable treatments for acute myocarditis are limited, mainly being heart transplantation and mechanical assistance devices. Particularly, three major approaches have been considered for the treatment of acute myocarditis:
  Pathogen inhibition (only for viral-induced myocarditis); IFNs are the most commonly used antiviral agent. However, the clinical application of antiviral agents is limited by the non-specific targeting, unclear mechanisms and side effects.
  Immune modulation; the acute phase of Myocarditis is characterized by myocyte necrosis and apoptosis and exaggerated autoimmune responses. Thus the application of immunosuppressive drugs is the treatment of choice: prednisone, non-steroidal anti-inflammatory drugs or intravenous Immunoglobulins (IVIG) have been tested, although the results obtained remains controversial due to the variability etiology of the disease.

heart failure therapy: including angiotensin-converting enzyme inhibitors, angiotensin II receptor blockers, β-blockers, aldosterone antagonists and calcium-channel blockers. Mechanical circulatory supports for heart function also aids in the recovery of myocarditis. Although such supports cannot cure myocarditis itself, the devices allow avoidance of fatality and increase the survival longevity of patients, especially in those with cardiogenic shock.

In the context of the present invention, suitable treatments for the initial therapy of acute myocardial infarction should be directed toward restoration of perfusion as soon as possible to salvage as much of the jeopardized myocardium as possible. This may be accomplished through medical or mechanical means, such as percutaneous coronary intervention (PCI), or coronary artery bypass graft (CABG) surgery.

Although the initial treatment of the different types of acute coronary syndrome (ACS) may appear to be similar, it is very important to distinguish between whether the patient is having an ST-elevation MI (STEMI) or a non-STEMI (NSTEMI), because definitive therapies differ between these two types of MI. Particular considerations and differences involve the urgency of therapy and the degree of evidence regarding different pharmacologic options.

Specific prehospital care includes the following:
Intravenous access, supplemental oxygen, pulse oximetry.
Immediate administration of aspirin en route.
Nitroglycerin for active chest pain, given sublingually or by spray.
Telemetry and prehospital electrocardiography (ECG), if available.
Management of ST-elevation myocardial infarction (MI) (STEMI) relies on two essential and key components: rapid recognition and timely reperfusion. Therefore, systems must be placed and implemented to prevent delay in management of patients who develop STEMI. Minimizing delays has been associated with improved overall outcomes as well as reduced mortality and long-term morbidity. Primary percutaneous intervention (PCI) is defined as an emergent percutaneous coronary intervention in the setting of STEMI, without previous fibrinolytic treatment. It is the preferred reperfusion strategy in patients with STEMI. Fibrinolysis is an important reperfusion strategy, particularly in settings where primary PCI cannot be offered to STEMI patients within the recommended timelines. The benefit of fibrinolytic therapy in patients with STEMI is well established, with the largest benefit seen when administered early (within 12 hours after symptomatic onset) and in patients with the highest cardiovascular risk.

Anticoagulant agents are an important adjunctive therapy for reperfusion therapy regardless of the strategy chosen (ie, whether it is primary PCI or fibrinolysis therapy). Different anticoagulation agents are available; the utility of each agent depends on the clinical context, taking into account the method of reperfusion.

All patients with STEMI should receive an empiric loading dose of aspirin (150.5 to 325 mg) as early as possible and prior to reperfusion, regardless of the reperfusion method. A lifelong maintenance dose of (75 to 81 mg) daily should be prescribed to all patients after STEMI.

A sixth aspect of the invention, relates to a kit or device comprising at least one or more oligonucleotides capable of hybridizing with any one of the miRNAs defined in the first or fourth aspects of the invention, preferably for hybridizing with miR-721 and/or miR-155, more preferably for hybridizing with SEQ ID NO 4, means for detecting said hybridization, and a lysis agent as defined above. Preferably, said kit or device additionally comprises a polyT oligonucleotide primer and the oligonucleotide(s) are optionally immobilized in stains on a surface, preferably on the surface of a microarray.

As used herein, "means for detecting said hybridization" is understood as labeled complementary DNA, RNA, modified nucleic acid strand (i.e. probe) to localize a miRNA sequence in a biological samples such as a blood, serum or plasma sample or in a portion or section of tissue, in the entire tissue or cells.

A seventh aspect of the invention relates to the in vitro use of the kit as defined in the sixth aspect of the invention or of a kit or device comprising at least one or more oligonucleotides capable of hybridizing with any one of the miRNAs defined in any of the first or fourth aspects of the invention, for detecting or diagnosing or for obtaining data useful for diagnosing a cardiomyopathy in a human subject. Preferably, said kit or device additionally comprises a polyT oligonucleotide primer and the oligonucleotide(s) are optionally immobilized in stains on a surface, preferably on the surface of a microarray. More preferably, the use of said kits or devices is for detecting or diagnosing or for obtaining data useful for diagnosing a myocarditis, preferably an acute myocarditis, acute myocardial infarction or for diagnosing Takotsubo syndrome in a human subject.

An eight aspect of the invention refers to a nucleotide sequence consisting of SEQ ID NO 4.

An ninth aspect of the invention refers to a fully complementary (100% complementary) DNA, RNA or modified nucleic acid strand (i.e. probe) capable of hybridizing with miRNA sequence SEQ ID NO 4, in particular with no mismatches.

A preferred embodiment of the eighth or ninth aspect of the invention refers to a genetic construct, such as a DNA sequence, capable of transcribing miRNA sequence SEQ ID NO 4.

The following examples help to illustrate but do not limit the present invention.

EXAMPLES

Example 1. Cloning miRNA-721 and Characterizing its Target Genes miRNA-721 was first described in a paper on mouse embryon brain tissue, in which the expression thereof during central nervous system embryogenesis was studied (Wheeler et al., FEBS Letters 2006). In this paper, miRNA was identified as miRY and was subsequently entered in the miR Base as mir-721. This miRNA is located in chromosome 5 within the non-coding region of CUX1 gene. miR-721 belongs to the family of miRNAs miR-130/301/721 (FIG. 1).

To study this microRNA in depth and its role in regulating inflammation and therefore in cardiovascular diseases, miRNA was cloned into expression vectors to conduct loss and gain of function assays, as well as for the functional validation of the possible target genes of this miRNA. Since the assays must essentially be conducted in primary cells, retroviral and lentiviral expression vectors have been tested, because they are the most efficient tools for gene expression in mammalian cells given their high ability of being integrated into the host cell genome.

1.2. Cloning miR-721 and Sponge Sequences

Figure 5:
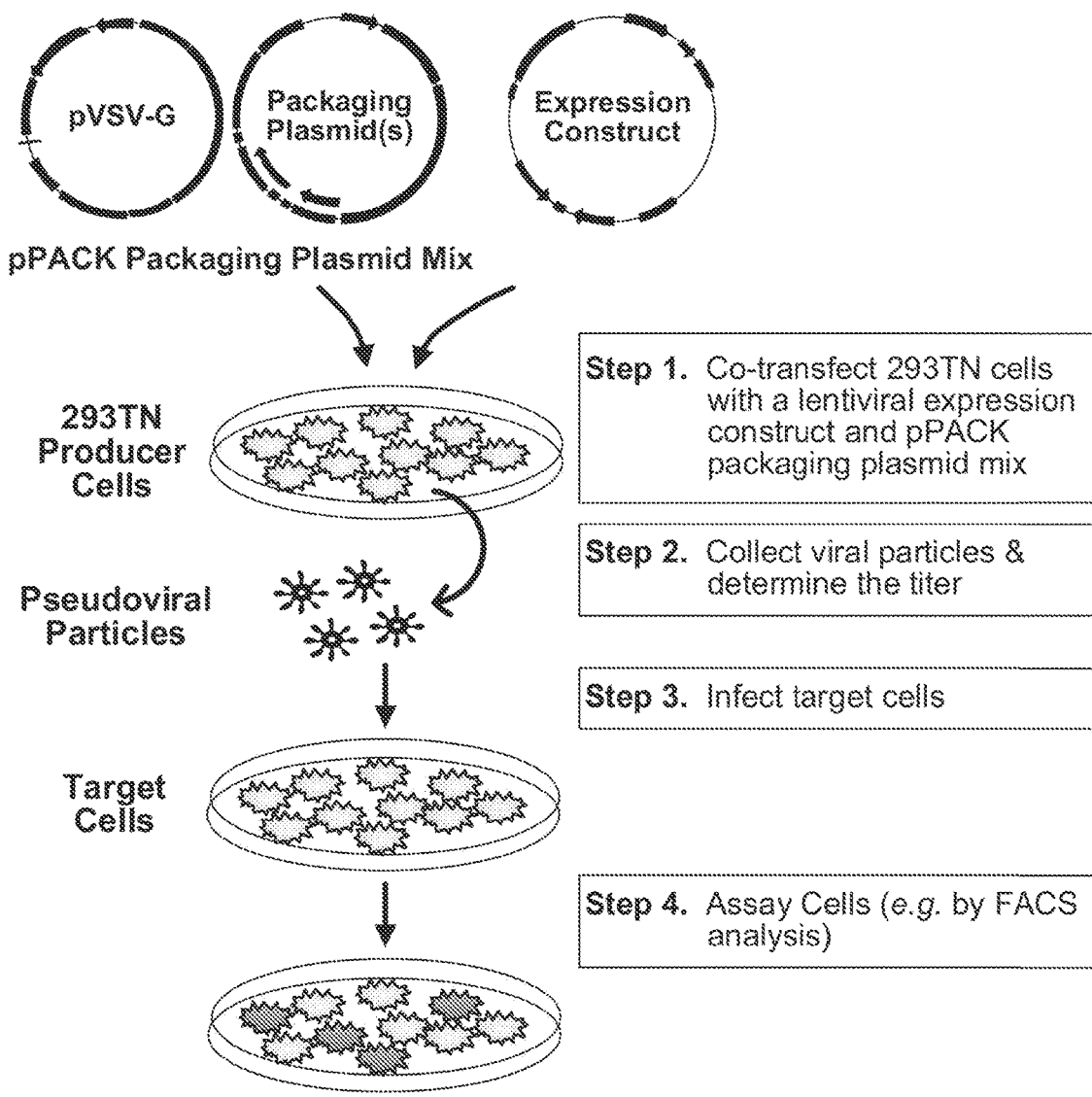
FIG. 5 shows the cloning scheme of miR-721 the miR-721 sponge and the expression thereof in lentiviral vectors. The design and cloning of miR-721 into plasmid, mature miRNA-721 expression and design and cloning of sponge sequences are shown on the left pSIN-BX/pHRSIN (immature miR-721) and pCDH-CMV-MCS-EF1-copGFP (sponge sequence for miR-721). The scheme of Lentivirus production processes and functional assays are shown on the right.

For the cloning were designed several flanking sequences of immature miR-721 sequence, of around 50, 75 and 100 base pairs (in both 5' and 3' directions), in order to assure correctly processing immature miRNA to mature miRNA, because a duly folded secondary structure is required in order to have mature and functional miRNA (FIGS. 2 and 3). Finally, a murine lentiviral vector (pSIN-BX/pHRSIN vector) is used in order to infect primary cells with pre-miRNA-721 with a high output (FIG. 5).

Furthermore, the sponge system is used to silence miR-721, consisting in the overexpression of the complementary sequence of miRNA mature in a murine lentiviral vector (pCDH-CMV-MCS-EF1-copGFP vector), which acts like a buffer blocking the functional molecules of the miRNA of interest. This construction contains 4 complementary sequences separated by spacers having between 4 and 5 base pairs (FIGS. 4 and 5). These silencing sequences, which are specific for miRNA and have allowed studying the effect of the loss of function of miRNA in functional in vitro assays, will also be very useful for studying the in vivo function thereof.

Lentiviral particles are produced by transfection (calcium phosphate method) of HEK293 cell line with the plasmid in which the sequence of interest of the present invention is expressed together with the lentiviral polymerase and envelope plasmids. The lentivirus are collected from the culture supernatant and concentrated by means of ultracentrifugation. The virus stock is kept at −80° C. until use (FIG. 5). The infective capacity of each batch is evaluated by means of infection with different concentrations of the lentiviral preparation in Jurkat cells. Infection levels are determined by quantifying GFP+ cells by flow cytometry.

1.3. miR-721 Expression in Mouse Primary Cells

Figure 6:
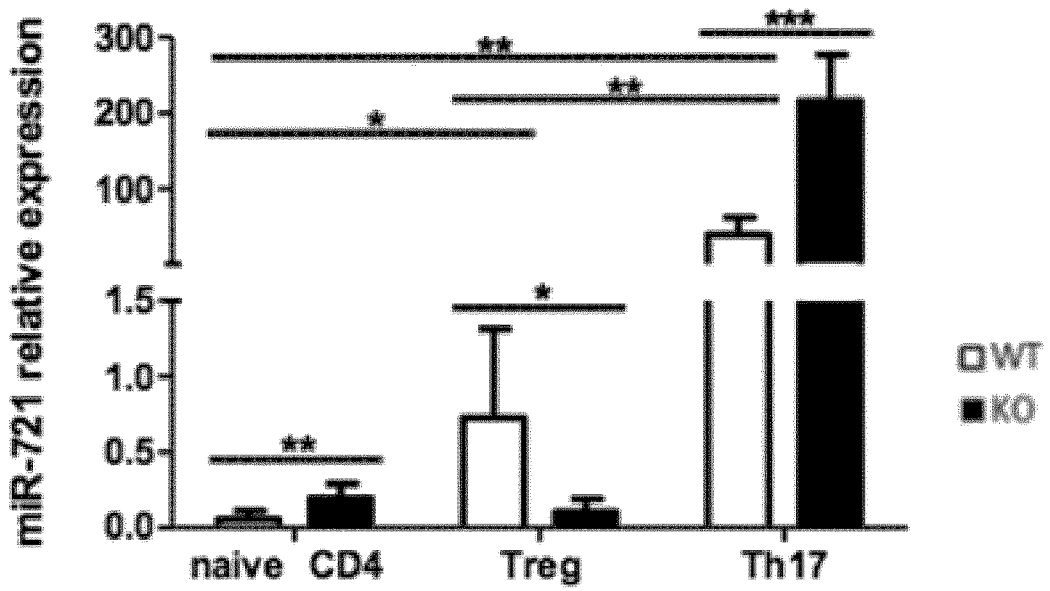
FIG. 6 shows miR-721 relative expression in naive T $CD4^+$ cells, Treg cells and $T_H17$ cells isolated from CD69WT and CD69KO mice. The error bars represent the mean±SD. (*$P<0.05$, $P<0.01$, *$P<0.001$, Student's t-test).

These assays were carried out in mouse primary cells. miRNA-721 is expressed in T lymphocytes, fundamentally in Th17 cells, and CD69 expression limits miR-721 levels in these cells (FIG. 6).

Figure 7:
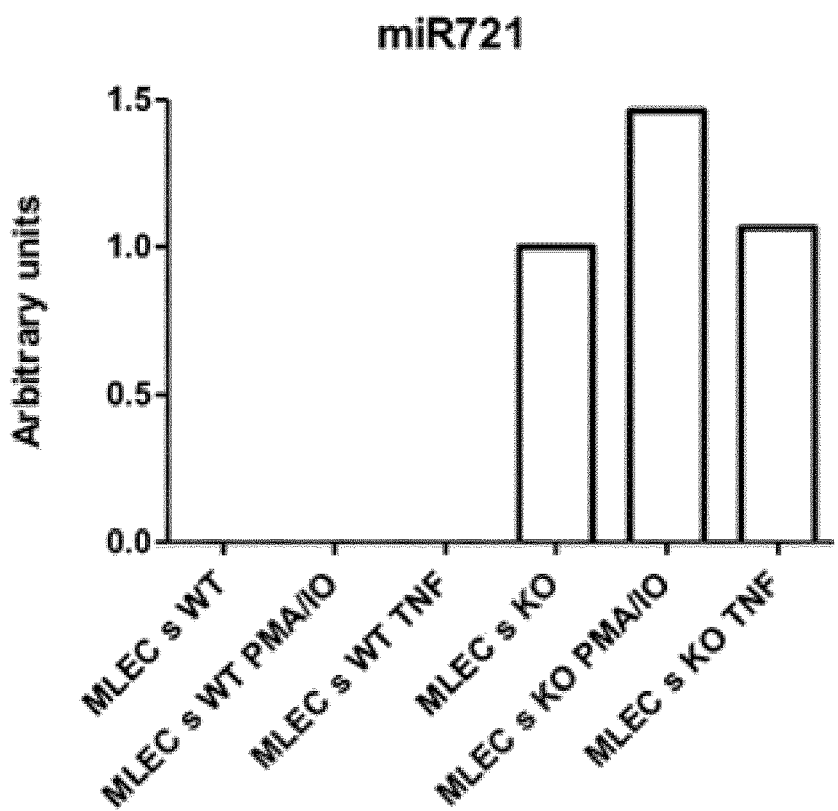
FIG. 7 shows miR-721 expression in primary mouse lung endothelial cells (MLEC) CD69WT and CD69KO. The MLECs were isolated from the lungs of 7 WT mice and 7 CD69KO mice.

However, since Th17 cells are hard to obtain and keep in culture, mouse lung endothelial cells (MLEC) are used to conduct these assays. Like in CD69 WT mice naive CD4 cells, in these cells it is found that miR-721 expression is not detected in MLECs from CD69WT animals. Furthermore, MLEC stimulation with PMA/Iono or TNFα does not salve miR-721 expression in CD69WT mice (FIG. 7). However, MLECs isolated from CD69KO mice express detectable miR-721 levels in homeostasis and expression thereof is inducible after activation with PMA/Iono (FIG. 7).

1.4. Validation of Target Genes of miR-721

A single target gene validated as a target for miR-721, Meox-2 gene, has been described. The family of miRNAs miR-130/301/721 is a positive regulator of induced pluripotent stem cell (iPSC) generation by means of Meox-2 gene repression (Pfaff et al., EMBO reports 2011). The 3"UTR end of Meox-2 gene has a complementary sequence with respect to the family miR-130/301/721, whereby these miRNAs regulate expression thereof (FIG. 8).

In addition to Meox-2, complementary sequences in the 3"UTR end of CD69, CUX1 and Aryl Hydrocarbon Receptor (AHR) genes (FIG. 9) have been found, said genes being of interest in this study based on the following reasons: CD69 is the immunoregulatory molecule studied in the laboratory that plays a key role in the control of proinflammatory Th17 responses causing myocarditis and the action of which inhibits miR-721 expression; CUX-1, in the genomic sequence of which the miR-721 transcript is encoded, is directly related to the vessel generation, or angiogenesis, capacity of endothelial cells, essential processes in tissue recovery after inflammation or ischemia; and AHR is a nuclear receptor that plays a key role in Th17 cell and regulatory T cell (Treg) differentiation and function, which are vital for functional studies in the myocarditis model.

Figure 10:
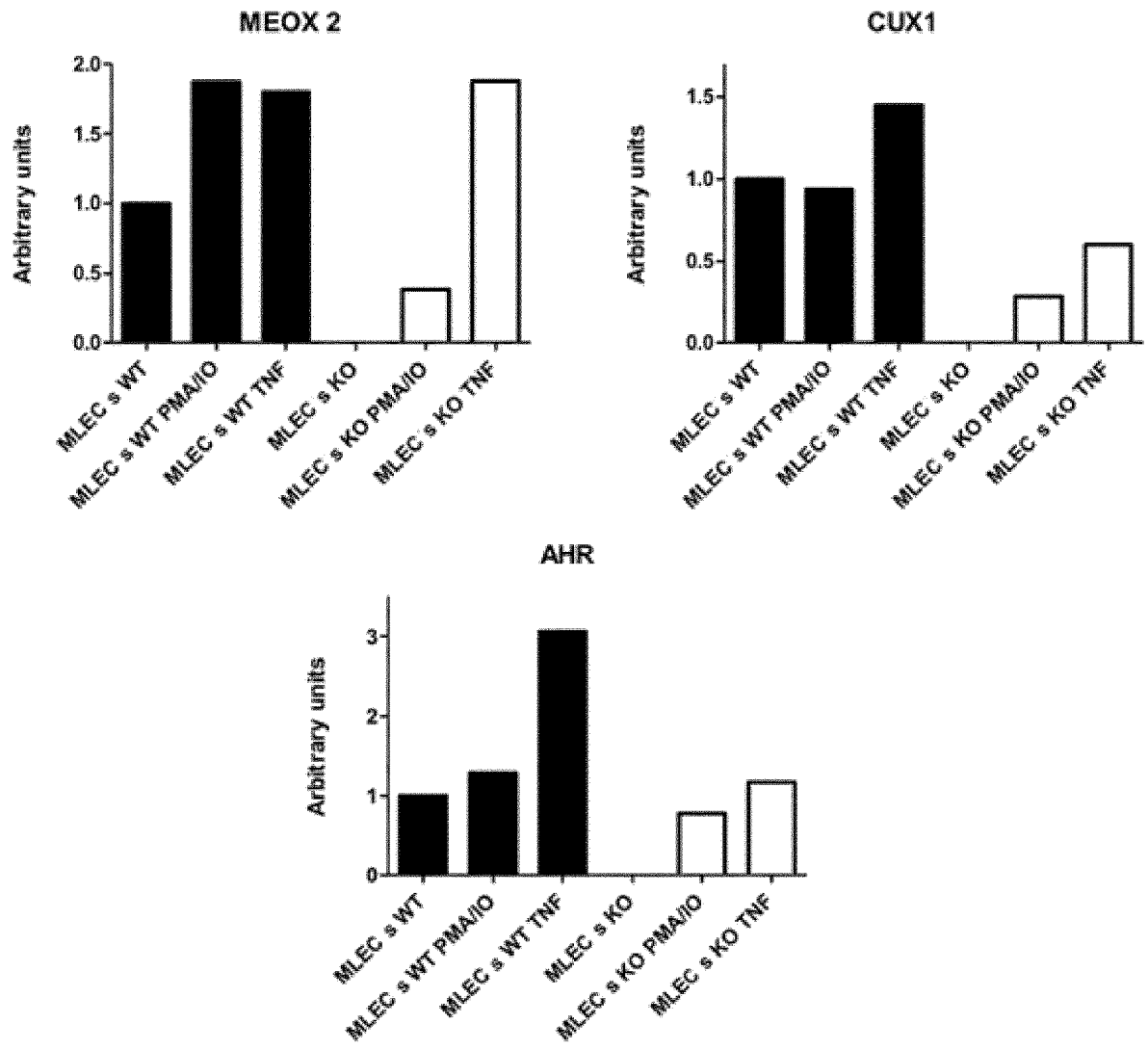
FIG. 10 shows the mRNA Meox-2 expression levels, CUX1 and AHR in MLECs from CD69WT and CD69KO mice.

To validate expression of these genes, qPCR was performed in MLECs from CD69WT and KO mice. With this technique it was found that in the presence of miR-721 in CD69KO MLECs, Meox-2, CUX1 and AHR gene transcription is completely inhibited and they are only expressed after activation with strong unspecific stimuli (PMA/Iono) angiogenesis specific stimuli (TNFα), whereas CD69WT MLECs, which does not express miR-721, express detectable levels of these 3 genes in baseline conditions and much higher levels after activation with the stimuli (FIG. 10).

1.5. In Vitro Functional Assays

To perform these assays, MLEC infection conditions had to be fine-tuned, for which purpose it is fundamental to know the titration of the virus and to infect with a multiplicity of infection (MOI) that is sufficient for infecting all the cells of the plate, but which in turn does not endanger cell viability. Several concentrations of lentiviral particles were tested and an MOI=5 (FIG. 11) was shown to be optimal.

Figure 12:
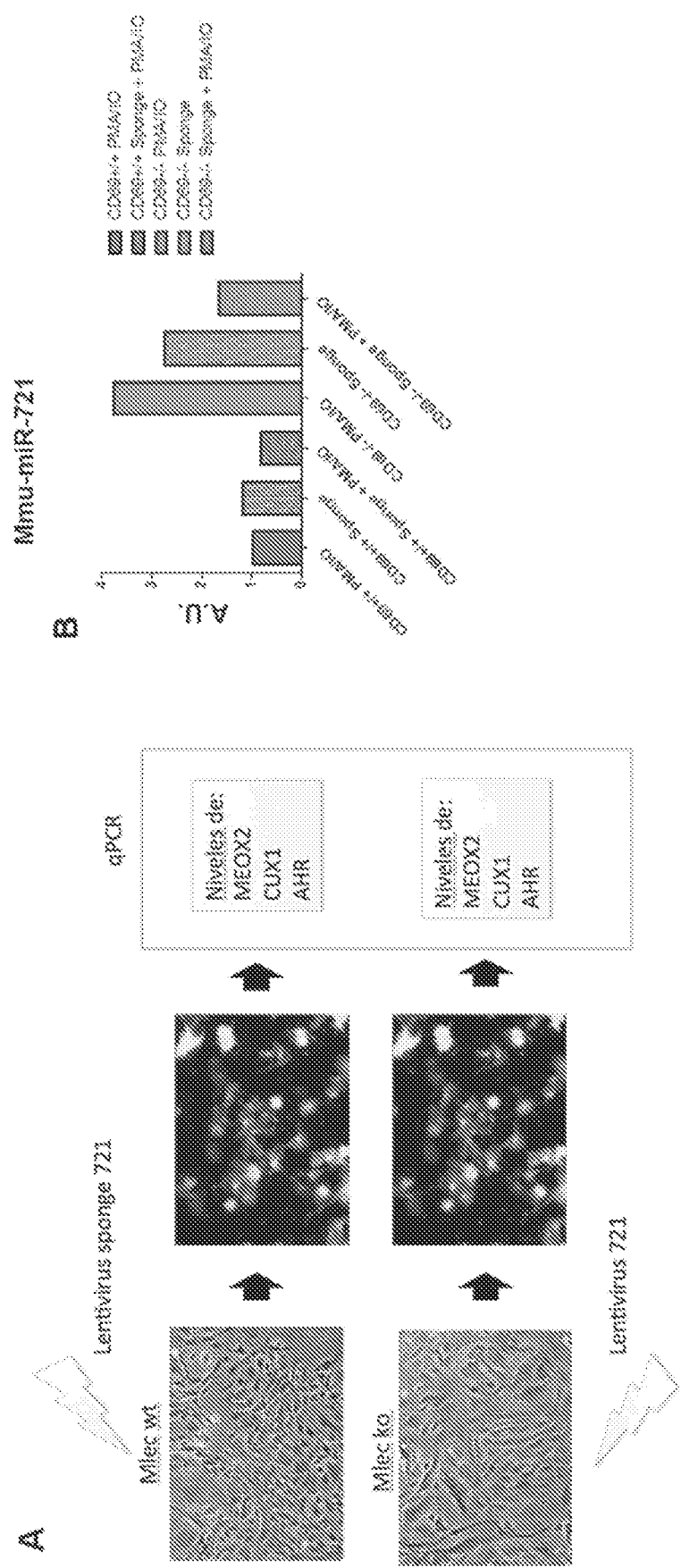
FIG. 12 shows the scheme of in vitro functional assays with lentivirus (A). (B) Expression levels of Mmu-miR-721 in Mlec treated with PMA/Iono in the presence or not of Sponge-miR-721.

Once these conditions were fine-tuned, in vitro assays were performed to validate Meox-2, AHR and CUX1 genes as miR-721 targets, by both overexpressing miR-721 and silencing it with Sponge sequences (FIG. 12).

Figure 13:
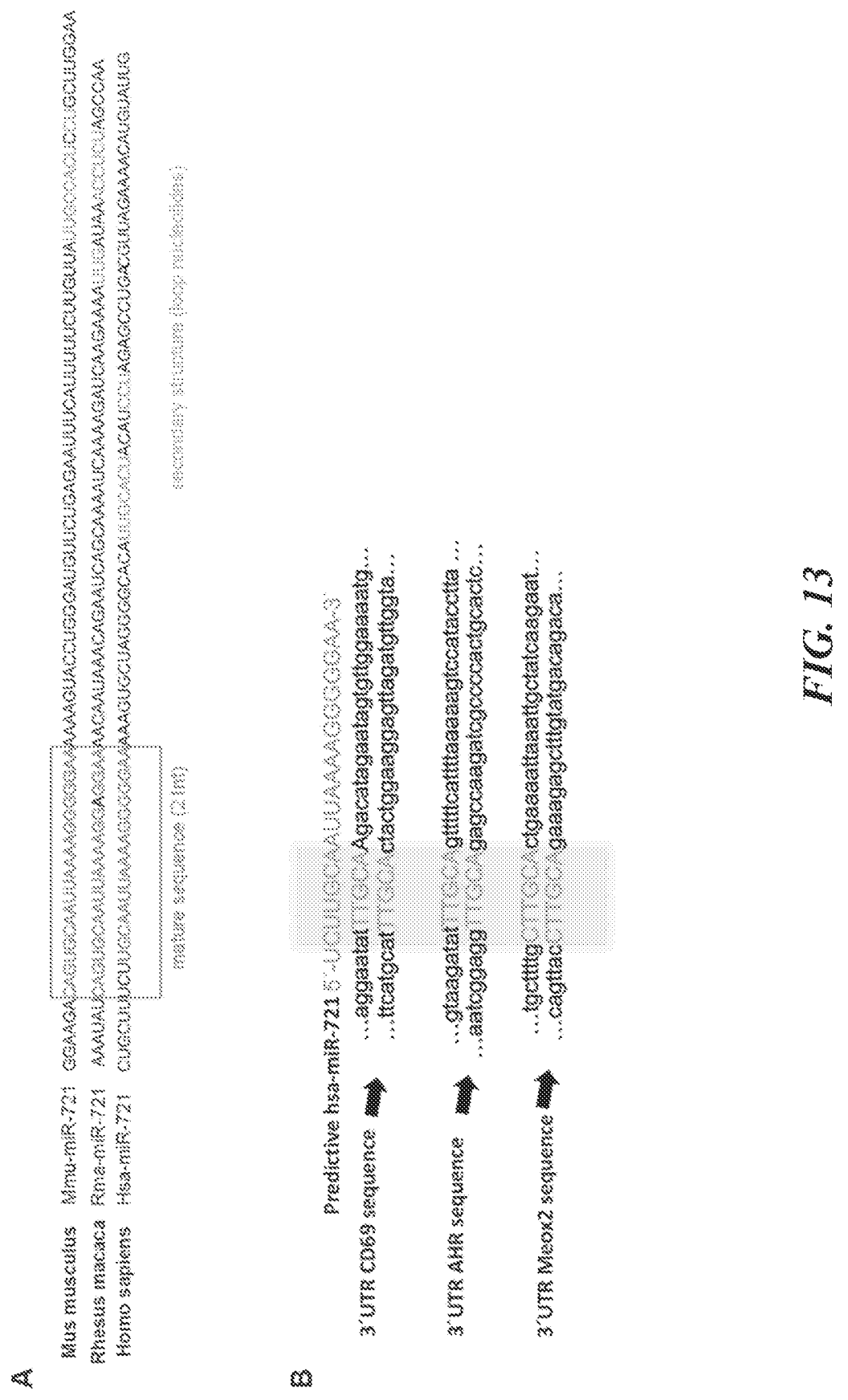

As miR-721 is a novel micro-RNA and has never been defined in human genome, we performed a multiple species sequence alignment of the murine miR-721 and defined the predictive sites for monkey and human miR-721 sequences (FIG. 13A). Moreover, we show UTR 3"binding sites for the putative target genes of hsa-miR-721: CD69, AHR and Meox2 (FIG. 13 B)

Figure 14:
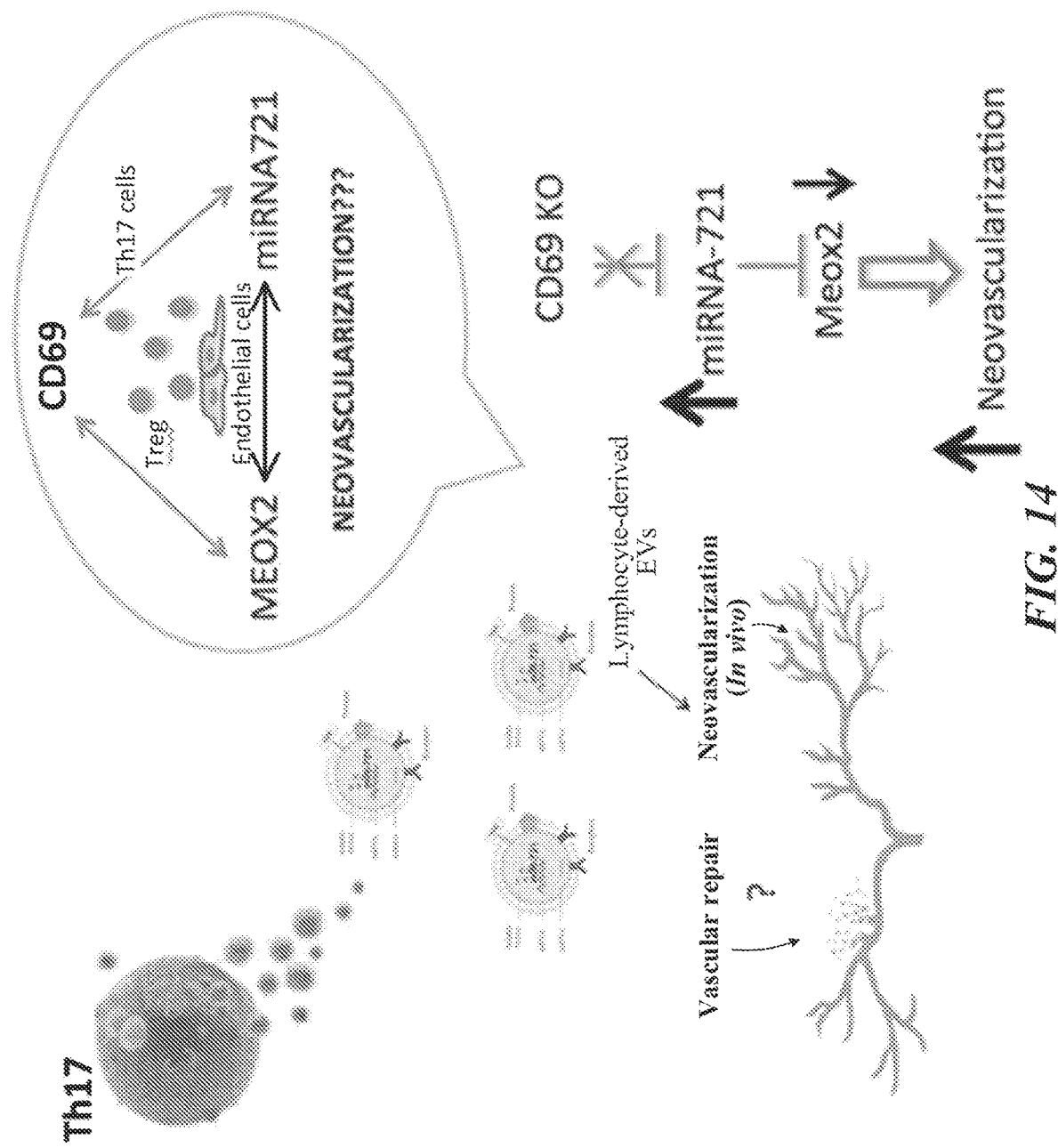
FIG. 14 shows the representative scheme of the role of miRNA-721 in angiogenesis processes.

According to these results, CD69 will act as a miR-721 repressor. In turn, miR-721 will be expressed both in Th17 and in endothelial cells and represses Meox-2, AHR and CUX1 genes expression, and therefore new vessel formation processes (FIG. 14).

Example 2

Figure 15:
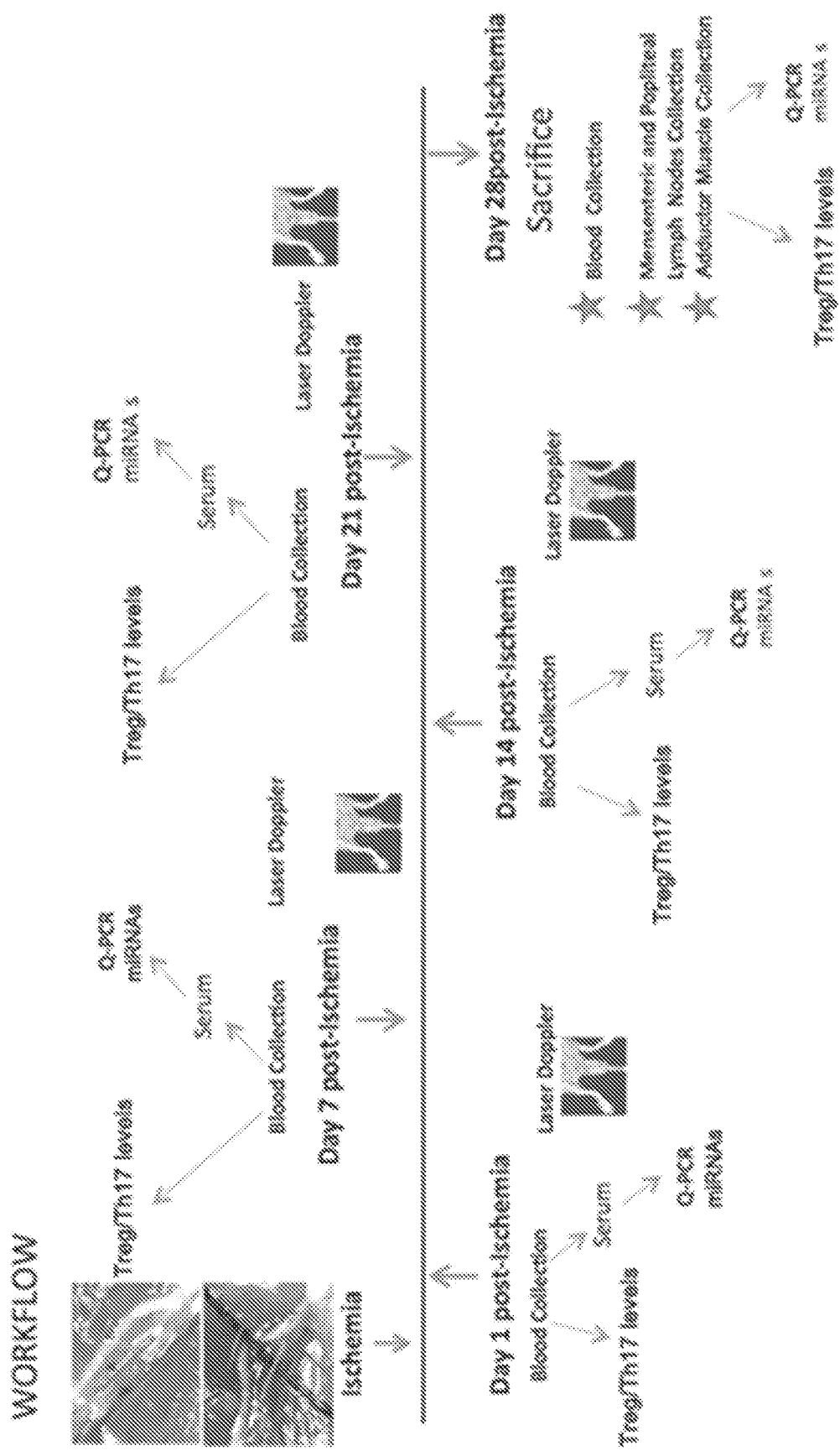
FIG. 15 shows the representative scheme of a standard experiment of femoral artery ischemia and monitoring of the revascularization process of the adductor muscle. The mice are analyzed on days 1, 7, 14, 21 and 28 after surgery by laser Doppler and blood samples from which circulating lymphocytes are obtained are taken to analyze Th17/Treg responses by FACS, and serum samples are taken to analyze the miRNA content. In most experiments, unless indicated otherwise, are sacrificed the mice on day 28 and blood samples (peripheral lymphocytes and serum), lymphoid node samples and muscle samples are taken. A: artery, V: vein, N: nerve.

2.1. In Vivo Experiments for Validating the Role of miR-721 in the Th17 Cell Effector Function Since the study of miR-721 function in the experimental autoimmune myocarditis (EAM) model requires very extensive experiments and working highly inaccessible tissue, the myocardium, a mouse lower limb muscle mouse ischemia model that is widely used in research to study the peripheral arterial disease (PAD) has been developed in the laboratory. To that end, the animals are subjected to a surgery explained next: a 5 mm incision is made in the inguinal area of the left leg allowing exposure of the femoral nerve, vein and artery. The connective tissue is carefully separated, and the vein, artery and nerve are dissected by means of separating the arterial adventitia layer close to the area distal to the femoral artery bifurcation. Once the three components are separated, the femoral artery is ligated by carefully passing thereunder a suture thread and making two surgical knots close to one another. The femoral artery is cut between the two knots that are made. The incision that is made will be sewn up after washing with physiological saline at a moderate temperature of 37° C. Femoral artery occlusion will allow the blood to flow towards the collateral artery, allowing new blood vessel formation (neovascularization) with the subsequent re-irrigation of the leg. The adductor muscle reperfusion monitoring process is carried out by means of analysis by laser Doppler (FIG. 15).

Inflammation and autoimmune anomalies play a crucial role in heart and vascular failure progression. Among other molecules, microRNAs have been proposed as one of the most innovative tools for the development of therapies against inflammatory and cardiovascular diseases. A number of papers relate T helper 17 (Th17) cells and the regulatory T (Treg) cells with cardiovascular diseases such as acute coronary syndrome or congestive heart failure. Furthermore, studies conducted in mice after femoral artery ischemia show that Th17 and Tregs modulate post-ischemic neovascularization in an antagonistic manner, revealing a crucial role of those cells in cardiovascular diseases such as peripheral arterial disease (PAD). However, the role of miRNAs derived from these cells is completely unexplored in this field, leaving a window open to the development of new diagnostic and therapeutic tools. This topic is being approached in the laboratory by means of the analysis of the CD69 leukocyte antigen as a Th17/Treg balance regulator because this molecule can be used as a connection link between cardiac inflammation mediated by Th17 cells and heart failure. Results have shown that there are at least 80 miRNAs that are differentially expressed in CD69-deficient Th17 cells compared to WT. Of all these miRNAs, this study focuses on miR-721 because its possible target genes are extremely relevant both in the biology of Th17/Treg cells and in cardiovascular diseases, including among them SOCS-1, AHR, STAT-3, RORγt or Meox-2. With the exception of Meox-2, these miRNA/target gene pairs have never been validated or described in Th17/Treg cells or in cardiovascular diseases. Furthermore, high expression of these miRNAs has been found in lymphoid cells, heart cells and serum from mice with autoimmune myocarditis or after femoral artery ischemia, as well as in patients with cardiomyopathies.

Therefore, femoral ischemia or PAD experiments are based on the hypothesis that CD69KO mice will have exacerbated Th17 responses and high miR-721 expression. In this model, it is described that Th17 cells positively regulate processes of arteriogenesis (Hata et al., Cardiovascular Research 2011), and that Treg cells do so in a negative manner, i.e., inhibiting the process of angiogenesis (Zouggari et al., Circulation 2009).

Taking the foregoing into account, if the hypothesis of the present invention is true, the revascularization process after ischemia should be enhanced in CD69KO animals versus WT animals, because miR-721 will act on Meox-2 and CUX1 genes, angiogenesis inhibitors.

Figure 16:
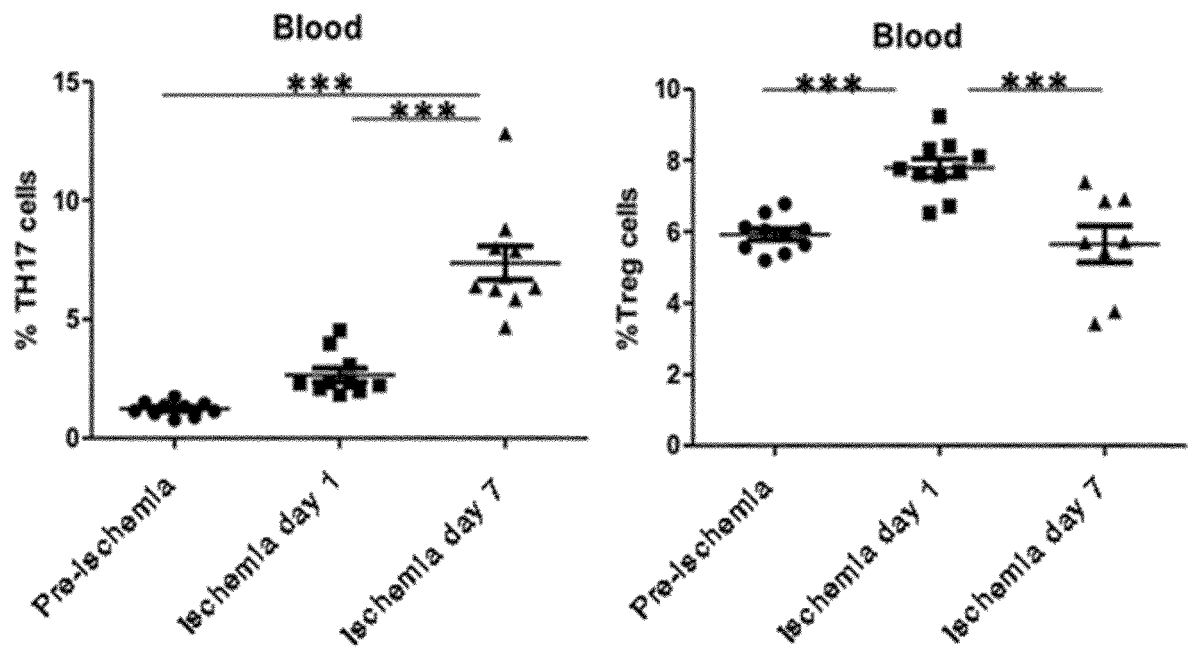
FIG. 16 shows the analysis of Th17 and Treg responses during the first week after femoral artery ischemia. The percentage of Th17 and Treg cells was analyzed after intracellular labeling with IL-17 and Foxp3, respectively, by flow cytometry. N=10. The data represents the mean+/− standard deviation. ANOVA (Bonferroni post-test).

2.2. Study of miR-721's Role and its Target Gene Meox-2 in Neovascularization after Femoral Artery Ischemia A study of Th17 and Treg cell kinetics in blood after inducing femoral artery ischemia was conducted. Once compared with the control mice, a progressive and significant increase in Th17 cells in blood during the 7 days following surgery can be seen. However, even though a peak in Treg is observed after 24 hours, Treg levels drop to almost baseline levels during day 7 of the experiment (FIG. 16). This data indicates that there is a strong pro-inflammatory response of Th17 cells that is maintained for one week after the ischemia process.

Figure 17:
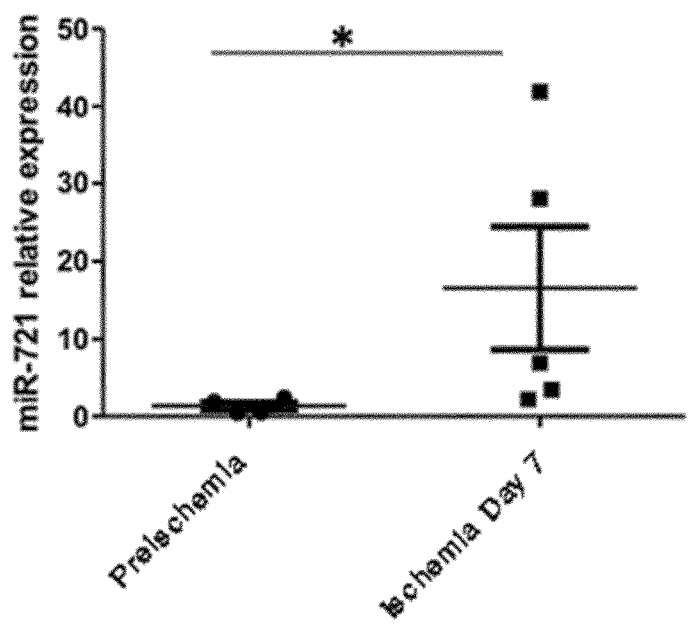
FIG. 17 shows miR-721 expression levels in the serum of mice with femoral artery ischemia. Serum levels of miR-721 were measured by qPCR. N=5. The data represents the mean+/−standard deviation. T-test (Mann-Whitney).

The increase in Th17 response 7 days after ischemia coincides with an increase of up to 40 times in miR-721 expression in the serum of these animals (FIG. 17), indicating that both Th17 responses and miRNA expression are increased. The detection of miR-721 in serum suggest that it could be secreted by Th17 cells, which are present at a high percentage 7 days after ischemia.

Figure 18:
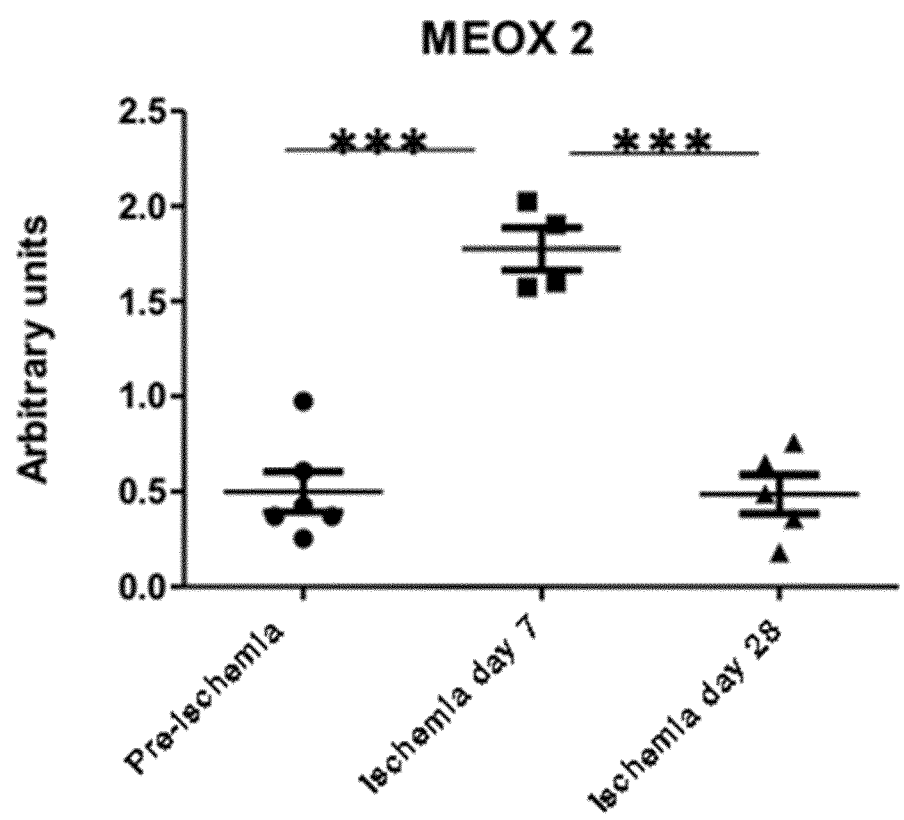
FIG. 18 shows Meox-2 expression levels measured by qPCR in the adductor muscle at various times after femoral ischemia.

2.3. Expression of the miR-721 Target Gene, Meox-2, is Inhibited after Inducing Ischemia In endothelial cells from the brain of patients with Alzheimer's disease, it has been demonstrated that Meox-2 silencing stimulates angiogenesis (Wu et al., Nature Medicine 2005), demonstrating that this gene exerts an inhibitory function on angiogenesis in endothelial cells. In the Meox-2 experiments for the present invention, it is induced in adductor muscle tissue 7 days after femoral artery ischemia, which indicates that this gene is activated in this tissue after ischemia (FIG. 18).

Figure 19:
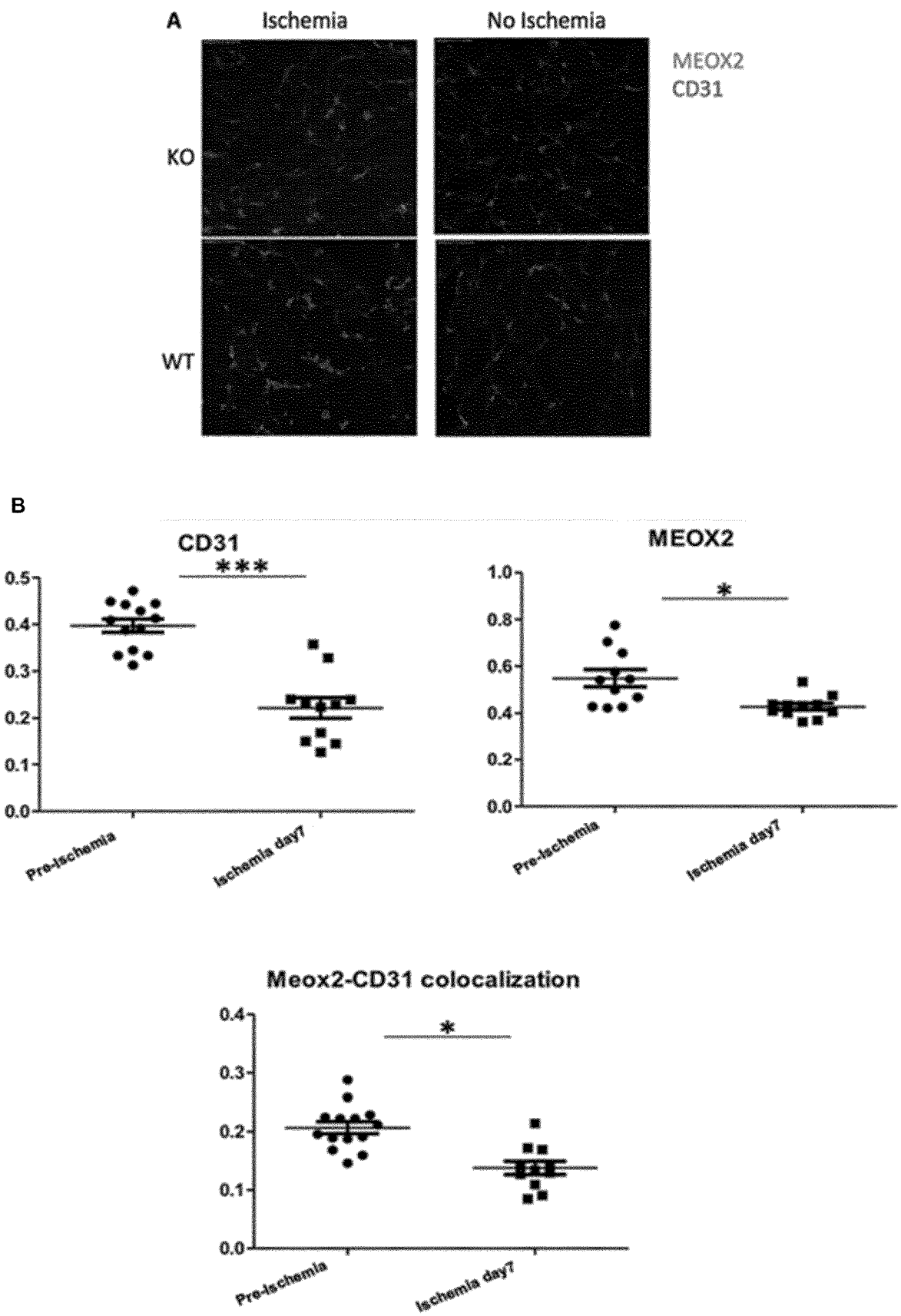
FIG. 19 shows immunofluorescence analysis of Meox-2 expression in mice muscle endothelial cells after 7 days of femoral artery ischemia. A) Representative images of immunofluorescence in muscle of Meox-2 and CD31. B) Quantification of CD31, Meox-2 expression and the co-localization of both in the ischemic muscle endothelial cells.

To verify Meox-2 inhibition in the endothelial compartment in these animals, immunofluorescence analysis of Meox-2 expression in CD31+ endothelial cells in the adductor muscle after 7 days of femoral ischemia is conducted (FIG. 19).

In this analysis it is observed that Meox-2 expression is inhibited in CD31+ endothelial cells after ischemia (FIG. 19), indicating that in angiogenesis processes this gene is repressed in endothelial cells and not in muscle cells.

Figure 20:
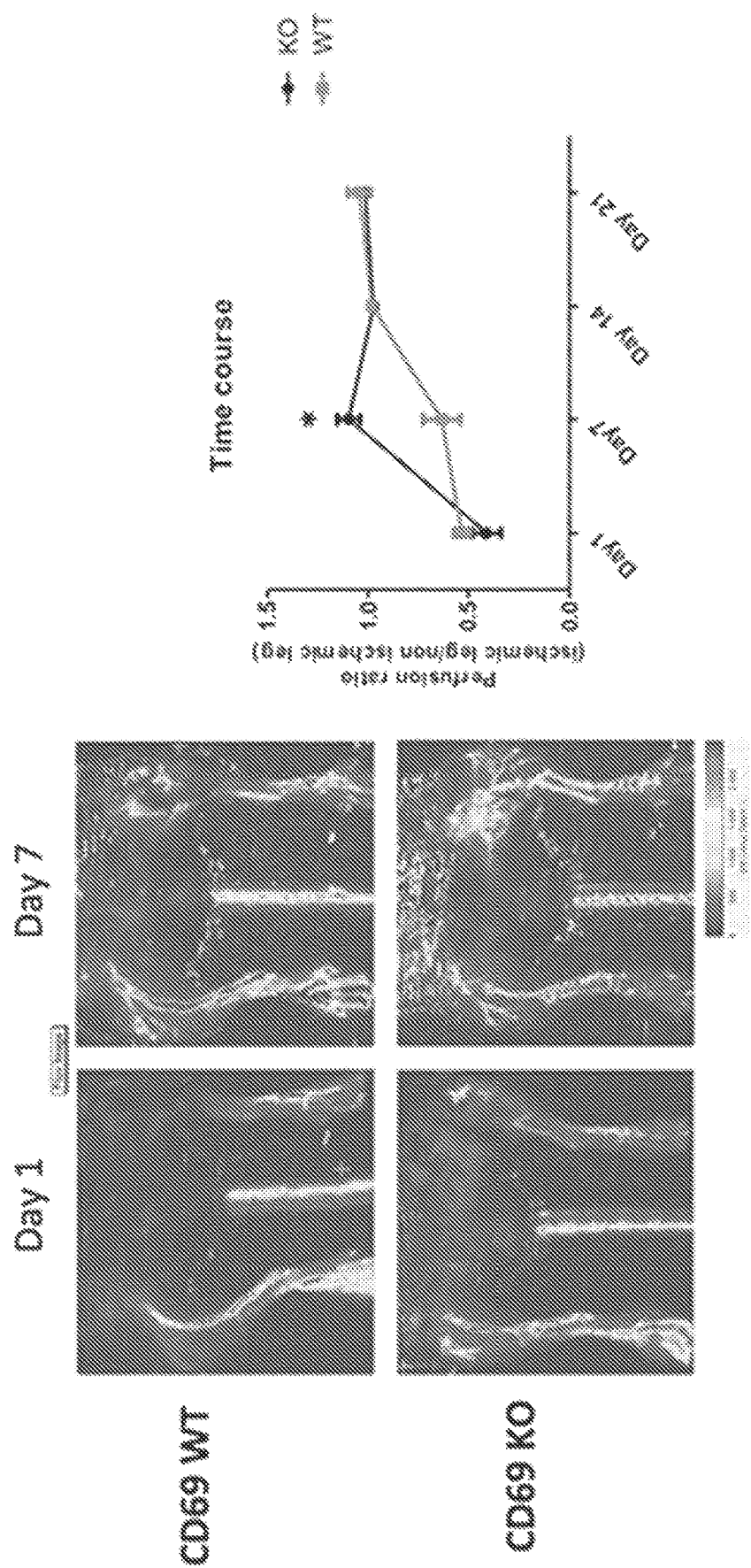
FIG. 20 shows, on the left, laser Doppler images taken 1 and 7 days after femoral artery ischemia in CD69 WT and CD69 KO mice of the BALB/c strain. On the right, the figure shows the revascularization process kinetics expressing the arbitrary values obtained from laser Doppler as the reperfusion ratio between the ischemic and non-ischemic leg in the same mouse.

In a preliminary study, revascularization after femoral artery ischemia in the right leg of CD69 WT and CD69KO mice of the BALB/c strain was studied, leaving the left leg as a control. Adductor muscle reperfusion monitoring was carried out by means of laser Doppler for one month after ischemia. According to the initial hypothesis, where CD69KO mice are more efficient in Th17 responses, it was found that the recovery kinetics (reperfusion ratio) of CD69KO animals is much faster compared to CD69WT animals (FIG. 20).

Figure 21:
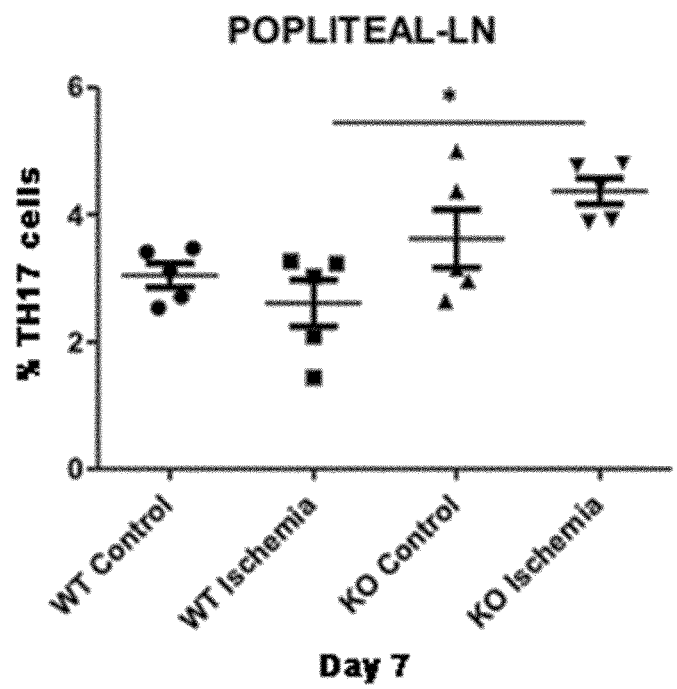
FIG. 21 shows the analysis of Th17 responses in the popliteal lymph nodes during the first week after femoral artery ischemia. The percentage of Th17 cells was analyzed after intracellular labeling with IL-17 by flow cytometry.

CD69KO mice have virtually recovered from ischemia 7 days after surgery, which coincides in these animals with a very significant increase in draining lymph nodes (popliteal) of Th17 cells (FIG. 21). This confirms that an increase in Th17 responses of CD69KO mice favors the revascularization process.

Figure 22:
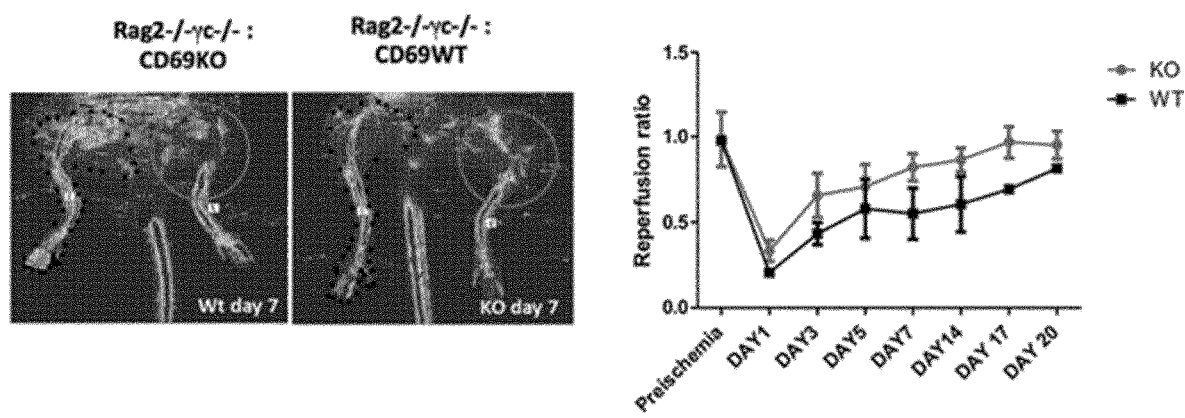
FIG. 22 shows, on the left, laser Doppler images taken 7 days after femoral artery ischemia in chimeras by irradiating BL/6 CD69 WT mice and reconstituted with bone marrow of Rag2−/−γc−/− and BL/6 CD69WT or CD69KO, at a 3:1 ratio, respectively. On the right, the figure shows the revascularization process kinetics expressing the arbitrary values obtained from laser Doppler as the ratio of reperfusion between the ischemic and non-ischemic leg in the same mouse.
Figure 23:
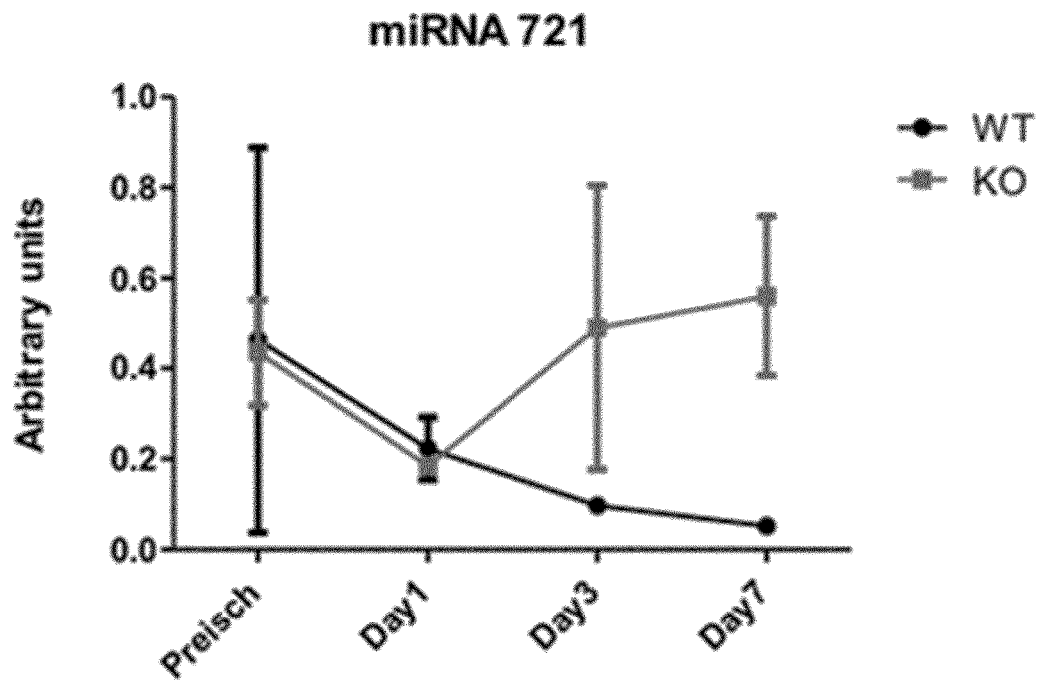
FIG. 23 shows miR-721 expression levels in the serum of BM BL/6 CD69WT and KO chimeras with femoral artery ischemia. miR-721 serum levels were measured by qPCR on days 1, 3 and 7 after ischemia.

2.4. miR-721 Generated by Th17 Cells Exerts its Effector Function on Target Genes in Endothelial Cells in Revascularization Processes after Ischemia Above it was described that MLEC endothelial cells of CD69 WT animals do not express miR-721 in homeostasis conditions or after activation with different stimuli, so the role of this miRNA in the lymphocyte compartment of the mouse must be studied. To that end, chimeras have been formed by irradiating BL/6 CD69 WT mice reconstituted with a mixture of bone marrow (BM) from Rag2−/−γc−/− animals that were lacking in precursors for T, B and NK cells, and from BL/6 CD69WT or CD69KO animals, at a 3:1 ratio, respectively. In these mixed chimeras, the entire myeloid compartment belongs to Rag2−/−γc−/− animals and is therefore WT, whereas the lymphoid compartment is generated from BL/6 BM, being CD69KO or WT in each case. Furthermore, these chimeras do not express miR-721 in the endothelium because all of the non-lymphoid tissue of the reconstituted animals is WT phenotype. It can therefore be expected that the miRNA-721 that is detected will be produced by the Th17 cells, and not by the endothelial cells. After inducing ischemia, it is observed that the chimeras reconstituted with BM BL/6 CD69KO have a more efficient revascularization process than the BM BL/6 CD69WT chimeras (FIG. 22), as occurred in the experiment with BALB/c CD69WT and KO animals, therefore confirming prior data.

miR-721 levels as well as levels of the target genes Meox-2 and CUX1 have also been studied in these mice. Like in BALB/c mice, miR-721 is induced 7 days after ischemia in the BM BL/6 CD69KO chimeras but not in the BM BL/6 CD69WT chimeras (FIG. 23).

Figure 24:
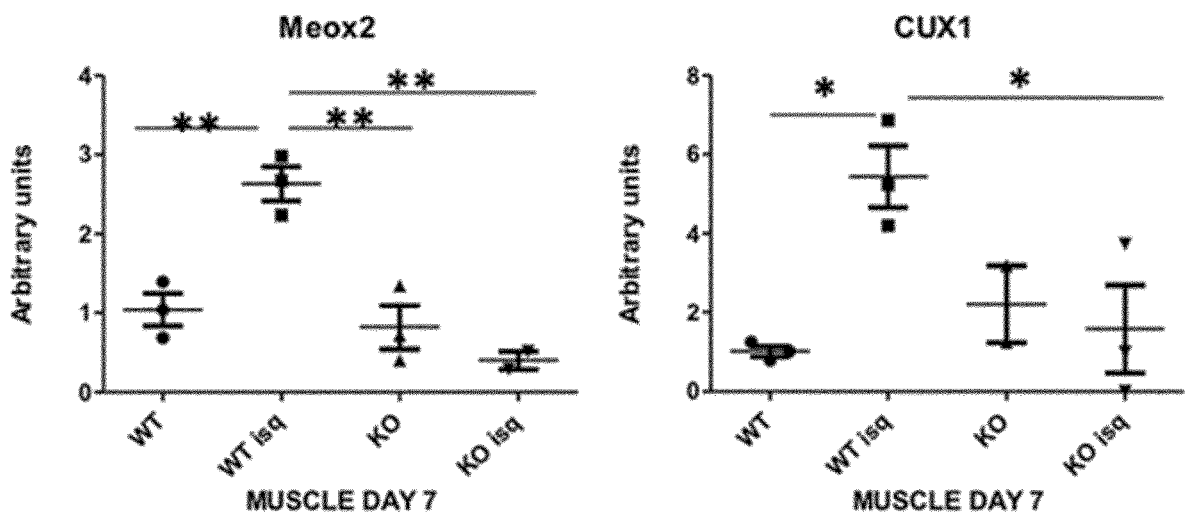
FIG. 24 shows Meox-2 and Cux1 expression levels measured by qPCR in the adductor muscle 7 days after femoral ischemia.

While Meox-2 and CUX1 gene expression is completely inhibited in the muscle tissue from BM BL/6 CD69KO chimeras, BM BL/6 CD69WT chimeras express high levels of these genes after 7 days of ischemia. This data indicates that high miR-721 expression in the serum of CD69KO chimeras is correlated to complete inhibition of its Meox-2 and CUX1 gene targets in muscle tissue (FIG. 24). Furthermore, Meox and CUX1 expression in the CD69WT chimeras is very high in ischemic muscle, whereas miR-721 is virtually not detected in the serum of these animals (FIG. 23). Taking into account that the endothelial cells of the chimeras do not synthesize miRNA-721, it can be expected that the changes observed in the target genes are induced by miR-721 expression by Th17 cells.

Example 3. Study of MIR721 and MIR155 Expression in the Animal Model of Experimental Autoimmune Myocarditis According to the results obtained, CD69-deficient naive T CD4+, T regulator and TH17 lymphocytes have changed the expression pattern of various microRNAs. The CD69 molecule limits the severity of cardiac dysfunction in the model of experimental autoimmune myocarditis (EAM) by means of controlling TH17 responses. To that end, this model is used to investigate the role of the previously mentioned miRNAs in this disease. The murine model of EAM is induced by means of immunization with a peptide derived from the α-myosin heavy chain (MyHCα) specific for heart tissue emulsified with CFA (Complete Freund's Adjuvant), which causes effector TH17 cell activation and differentiation. 21 days after immunization, the mice are in the acute phase of the disease, presenting inflammation in the myocardium and anti-cardiac myosin antibodies in serum. The chronic phase appears after 56 days, characterized by fibrosis and degeneration of the myocardium and, accordingly, the development of cardiomyopathies.

To validate the model of EAM with a non-invasive method, the immune response generated in the acute phase of EAM was characterized 21 days after immunization with the MyHCα peptide. To that end, an intravenous fluorescent probe detecting activated elastase and therefore neutrophils and inflammation foci was injected, and the mice were examined by means of fluorescence molecular tomography (FMT). With this technique, it was confirmed that CD69KO mice presented greater inflammation in the heart than WT mice (FIG. 25).

3.1. miRNA Expression Levels in the Heart

To investigate miRNA expressions during the acute phase of the model of EAM, after examining inflammation of the myocardium by means of fluorescence molecular tomography on day 21, the mice were sacrificed and the heart was extracted (FIG. 26).

Figure 27:
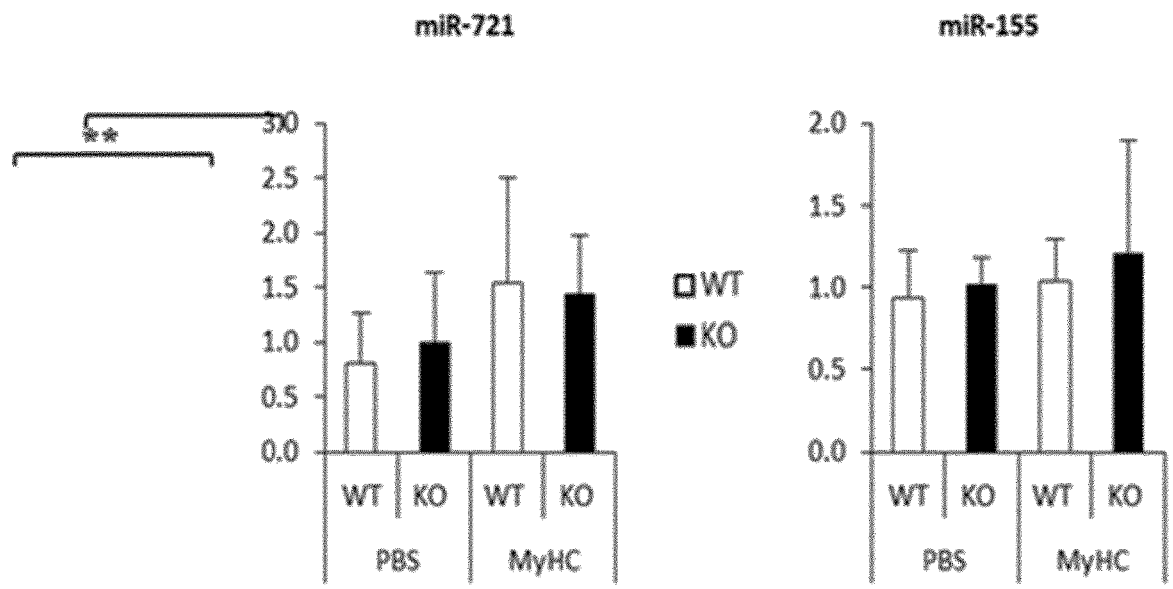
FIG. 27 shows the miRNA expression levels in the heart during the acute phase of EAM. miR-721 and miR-155 relative expression in the heart of WT and CD69KO mice during the acute phase of EAM were measured by qPCR. The error bars represent the mean±SD of 3 independent experiments (n=6). ($*P<0.05$, $**P<0.01$, One-way analysis of variance (ANOVA).

Analysis of miRNA expression levels present in the heart of the mice during the acute phase of EAM showed a significant increase in miR-721 expression in the heart of sick WT and CD69KO mice with respect to the control mice. In contrast, no significant differences in miR-155 expression levels in the hearts of the animals were found (FIG. 27).

3.2. miRNA Expression Levels in Serum

Figure 28:
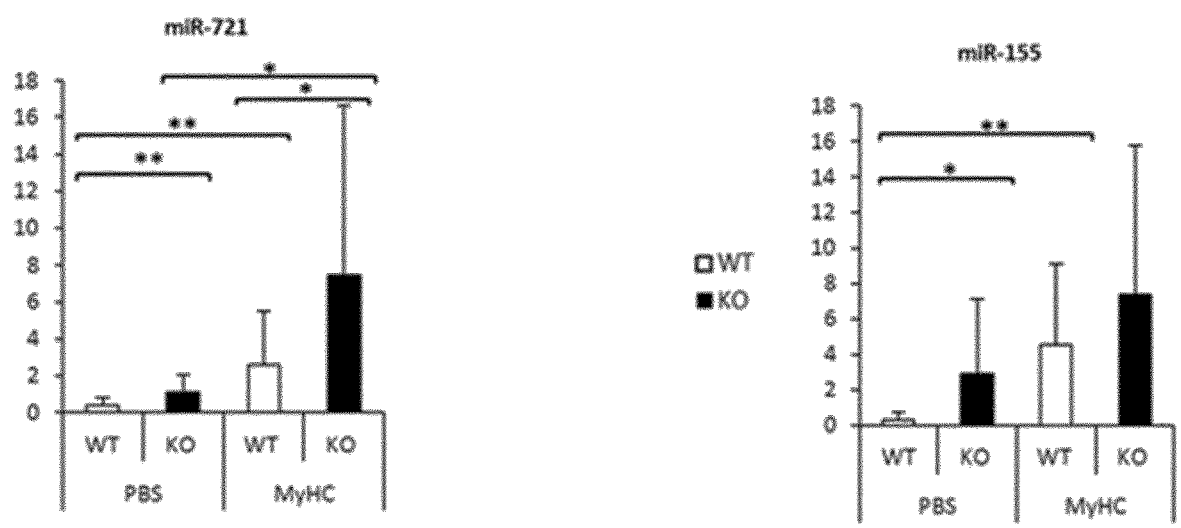
FIG. 28 shows miRNA expression levels in serum during the acute phase of EAM. miR-721 and miR-155 relative expression in blood serum of WT and CD69KO mice during the acute phase of EAM was measured by qPCR. The error bars represent the mean±SD (n=6). ($*P<0.05$, $**P<0.01$, One-way analysis of variance (ANOVA).

For the purpose of finding a microRNA detectable in blood that can be used as a diagnostic biomarker, as marker of the severity of myocarditis and/or as a therapeutic target of the disease, the miRNA expression pattern in the serum of mice with experimental autoimmune myocarditis was studied. To that end, blood was extracted from the mice during the acute phase of EAM and miRNA levels present in the serum were analyzed by means of quantitative PCR. The result obtained was a significant increase in miR-721 and miR-155 in the serum of sick mice with respect to the control animals. Furthermore, it was found that CD69KO mice with myocarditis showed greater miR-721 expression in serum than WT mice treated with the peptide MyHC animals and greater than the controls, suggesting that this miRNA could in fact be related to an increase in $T_H17$ and therefore related to the severity of the disease (FIG. 28).

Example 4. Analysis of $T_H17$ Lymphocytes, T Regulator Cells and miRNA Expression in Plasma from Patients with Cardiomyopathies Myocarditis is characterized by inflammatory cell infiltration into the myocardium. After the acute process, the loss of cardiomyocytes and the development of fibrosis and necrosis in the myocardium take place, ventricle remodeling, permanent dysfunction of the ventricular wall, dilated cardiomyopathy, heart failure and arrhythmias being able to arise. For the purpose of studying the role of T CD4+ lymphocytes in the development of the disease in humans and the potential thereof as therapeutic targets, these populations in the blood of patients with myocarditis and dilated cardiomyopathies were analyzed in comparison with healthy donors. Furthermore, the microRNA expression levels detected in the animal model of experimental autoimmune myocarditis in the blood plasma of patients and control subjects were measured to find a detectable miRNA in blood that could be used as a diagnostic biomarker and/or as a therapeutic target of the disease.

4.1. Analysis of Total T CD4+ Lymphocytes in the Blood of Patients

Figure 29:
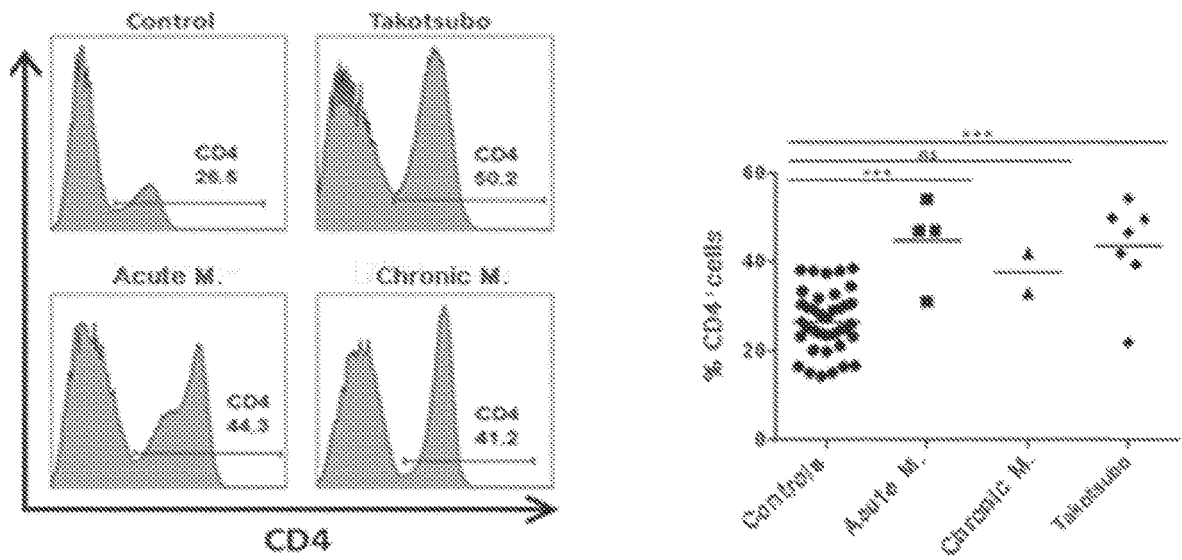
FIG. 29 shows the analysis of total T $CD4^+$ lymphocytes in the blood of patients with cardiomyopathies. The percentages of total T $CD4^+$ lymphocytes present in the blood of healthy subjects and patients with acute myocarditis, chronic myocarditis or Takotsubo cardiomyopathy were analyzed by flow cytometry. (ns=no significant differences, $*P<0.05$, $P<0.01$, $*P<0.001$, One-way analysis of variance (ANOVA)).

To quantify the percentage of total T CD4+ lymphocytes circulating in the blood of patients and controls, lymphocytes were isolated from EDTA-anticoagulated peripheral blood by means of a density gradient, and their membrane markers were analyzed by flow cytometry. The analysis showed a statistically significant increase in the proportion of total T CD4+ cells in the blood of patients with acute myocarditis or Takotsubo with respect to that of healthy subjects (FIG. 29).

4.2. Analysis of $T_H17$ Lymphocytes in the Blood of Patients

Figure 30:
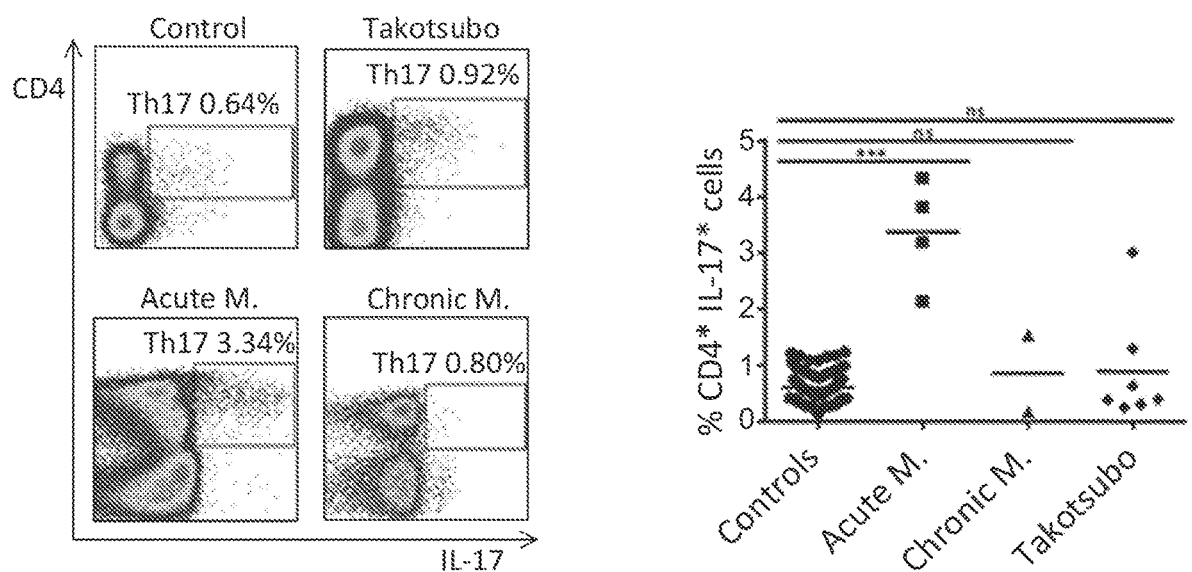
FIG. 30 shows the analysis of $T_H17$ lymphocytes in the blood of patients with myocarditis and dilated cardiomyopathies. The percentages of $T_H17$ lymphocytes relating to total T $CD4^+$ cells present in the blood of healthy subjects and patients with acute myocarditis, chronic myocarditis or Takotsubo cardiomyopathy were analyzed by flow cytometry. (ns=no significant differences, $*P<0.05$, $P<0.01$, $*P<0.001$, One-way analysis of variance (ANOVA)).

To analyze the percentages of $T_H17$ cells, the lymphocytes were isolated from peripheral blood by means of a density gradient, activated with anti-OKT3, restimulated with PMA, ionomycin and brefeldin and labeled with anti-CD4 and anti-IL-17. Analysis by flow cytometry showed that in total T CD4+ cells, the percentages of $T_H17$ lymphocytes in the blood of patients with chronic myocarditis or Takotsubo cardiomyopathy are similar to those of healthy controls, whereas patients with acute myocarditis have a proportion of $T_H17$ lymphocytes in blood that is significantly higher than that of healthy volunteers (FIG. 30), indicating that $T_H17$ responses could be specific to the acute phase of this disease.

4.3. Analysis of Naive and Memory Treg Lymphocytes in Blood

Figure 31:
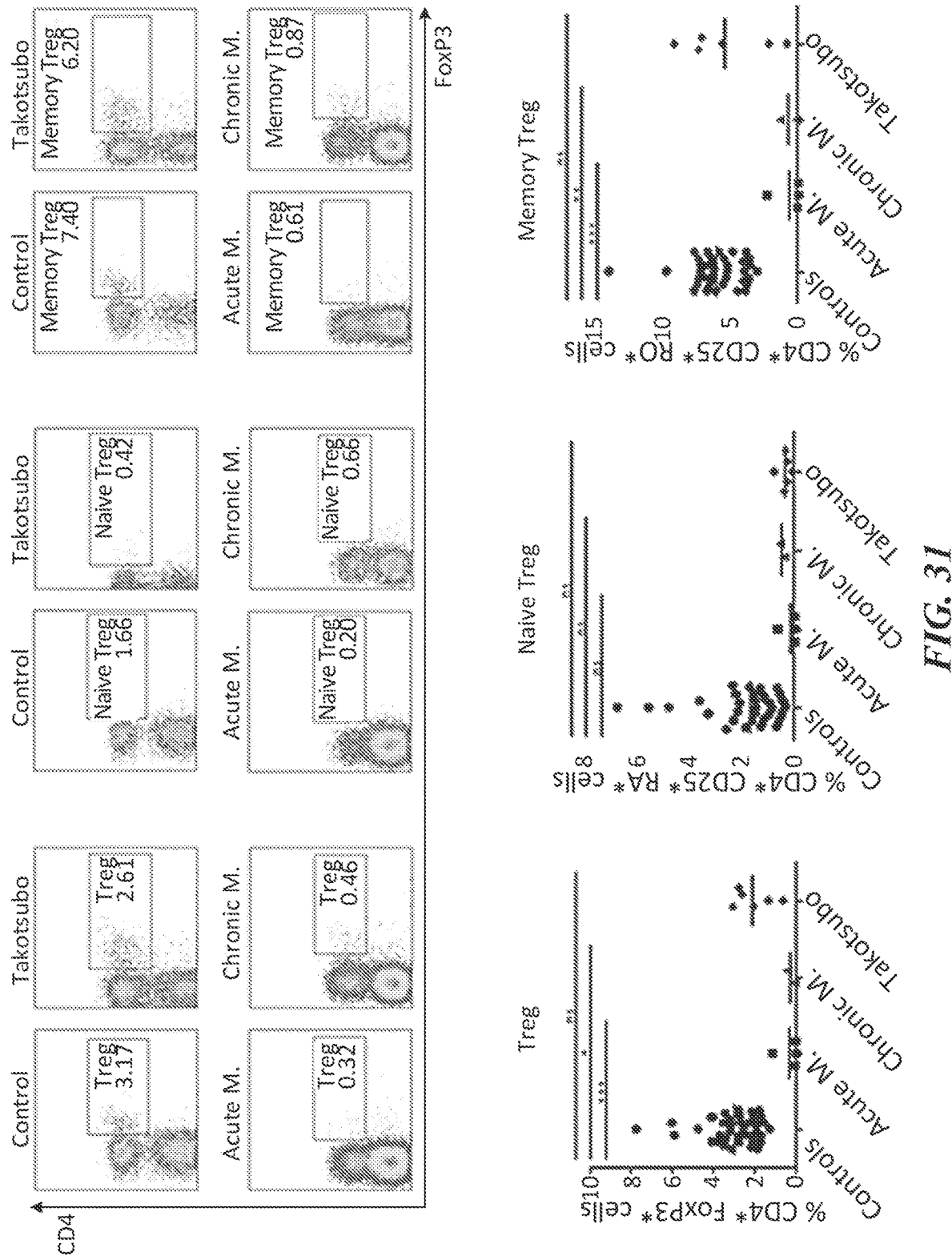
FIG. 31 shows the analysis of Treg lymphocytes in the blood of patients with myocarditis and dilated cardiomyopathies. The percentages of total Treg, naive Treg and memory Treg lymphocytes present in the blood of healthy subjects and patients with acute myocarditis, chronic myocarditis or Takotsubo cardiomyopathy were analyzed by flow cytometry. (ns=no significant differences, $*P<0.05$, $P<0.01$, $*P<0.001$, One-way analysis of variance (ANOVA)).

Analysis of the percentages of regulatory T cells present in the blood of patients with myocarditis and dilated cardiomyopathies comprised the study of total Treg cells, naive Treg cells and memory Treg cells. To that end, the lymphocytes extracted from the blood were activated with OKT3, and the CD4$^+$ CD25$^+$ FOXP3$^+$ (total Treg cells), CD4$^+$ CD25$^+$ FOXP3$^+$ CD45RA$^+$ CD45R0$^-$ (naive Tregs) and CD4$^+$ CD25$^+$ FOXP3$^+$ CD45RA$^-$ CD45RO$^+$ (memory Tregs) populations were analyzed. The result obtained was that patients with Takotsubo do not present statistically significant differences in relation to the percentages of regulatory T cells in peripheral blood with respect to healthy volunteers. However, patients with both acute and chronic myocarditis present percentages of total Treg cells that are significantly lower than those of control subjects, probably due to a significant reduction of the memory Treg cell population in these patients, because the naive Treg cell population is not affected in these patients. (FIG. 31).

4.4. miRNA Expression Levels in Blood Plasma

Finally, for the purpose of validating this study in patients with cardiopathies, the miRNA expression levels detected in the murine model of EAM, in the blood plasma of healthy subjects and patients with acute myocarditis, chronic myocarditis and Takotsubo syndrome were analyzed by extracting total RNA and quantifying the expression thereof by means of qPCR. The trend that was observed was an increase in miR-155 expression levels, and especially in miR-721 expression levels, in patients with cardiomyopathies with respect to healthy subjects, this being higher in patients with acute myocarditis than in those patients in the chronic phase of the disease, and particularly in patients with Takotsubo (FIG. 32).

The tables at the end of the present specification illustrate the amounts of sample of used in the present experiments to detect miRNA in the serum of mice with ischemia, myocarditis or in patients with myocarditis, and the comparison of the fold induction between these samples.

Example 5. Differential Diagnosis Between AMI and Myocarditis Patients 5.1. miRNA Expression in Mice after Myocarditis and AMI Induced by Coronary Descending Artery Ligation (LAD).

Figure 33A:
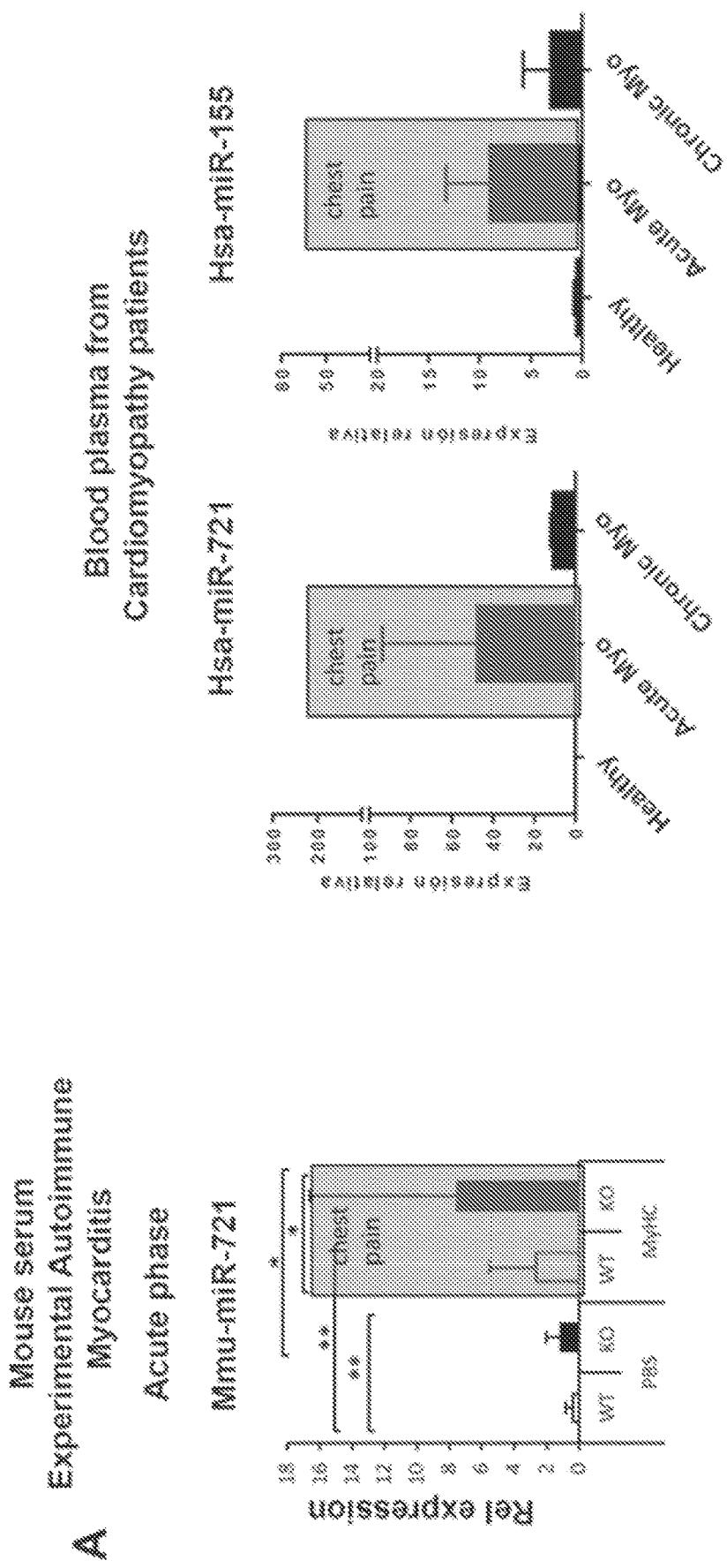
FIG. 33 (A) shows mouse miR-721 expression levels in the serum of mice in the acute phase of EAM (left) and human miR-721 and miR-155 expression levels in the blood plasma of patients with cardiomyopathies (right). (B) Scheme of the mouse model of descending coronary artery ligation to simulate an acute myocardial infarction used in this study, the levels of Th17 and murine miR-721 in the blood and plasma respectively are shown. Orange bar represent the manisfestation of the clinic symptoms (chest pain, fatigue, altered ECG . . . ).

Based on our previous results in the EAM model and a small cohort of 14 patients with different cardiomyopathies (acute and chronic myocarditis and Takotsubo) and healthy subjects, we found that miR-721 and miR-155 microRNAs derived from Th17 cells and Treg cells respectively, are present in the development of Myocarditis. We have identified and cloned the human miR-721 that we detected with the murine probe for miR-721, moreover we have identified Th17 cells as main producers of miR-721 in mice. As Th17 and Tregs are pivotal in Myocarditis development we found high levels of these miRNAs, when the symptoms appear in patients with Myocarditis compared to Healthy volunteers (FIG. 33A).

We have analyzed the Th17 cells in mice after coronary descending artery ligation or LAD simulating an Acute Myocardial infarction. We have found that Th17 cells appear in the blood of the mice after two weeks of the ischemic event (when the symptoms appear) and this is consistent with elevated miR-721 levels 15 days after the infarct (FIG. 33B). However, the manifestation of the symptoms (in the first hours after LAD) and the expression of miR-721 occurs in different time points (FIG. 33B).

All these data suggest that Myocarditis mice could be diagnose by presence of miR-721 in plasma or serum, whereas AMI mice do not.

Some Acute Myocarditis can mimic AMI symptoms in the first hours and therefore we proposed miR-721 detection in blood as a bona-fide diagnostic tool for Myocarditis patients.

5.2. miRNA Profiling in the Exosomal Fraction of Th17 Cells.

Because of the fact that miR-721 is found in serum of myocarditis mice and patients we estimated it could be coated into exosomes.

So far, the content of selected miRNAs was analyzed by qPCR in exosomes isolated from plasma after PEG (polyethylene glycol) precipitation. We first analyzed the content of miR-721 within exosomes secreted from EAM lymph node cells in mice with moderate myocarditis (WT) and severe myocarditis (CD69−/−) as described in Cruz-Adalia et al, Circulation 2010. First, we collected dLN from wild type and CD69−/− mice 6 days after EAM induction and we cultured them for 48 h in an exosome-free medium (FIG. 34A).

Figure 34:
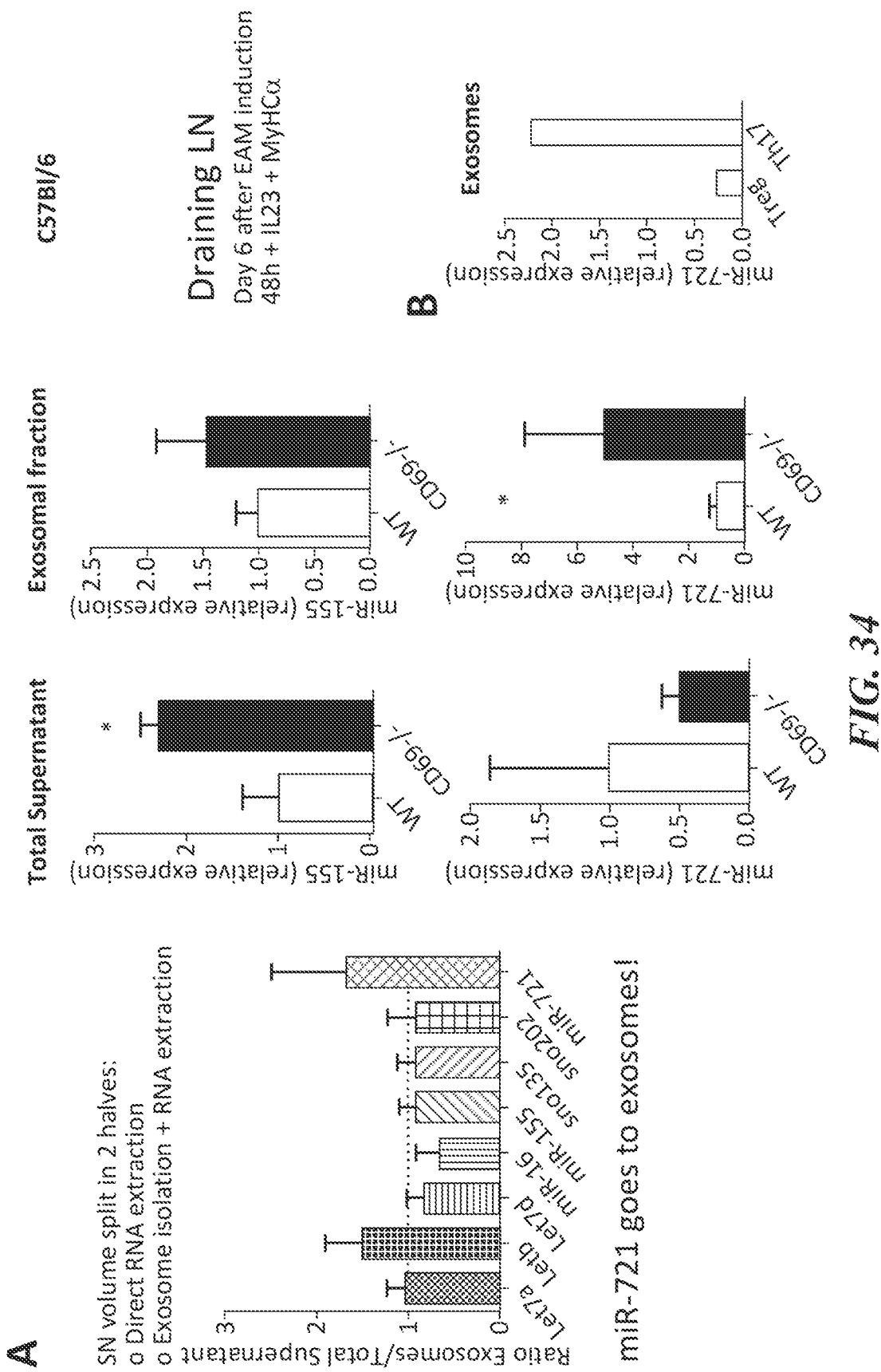
FIG. 34. MiR-721 is present in exosomes from EAM-induced immune cells. A RT-qPCR analysis of miR-721 expression in exosomes from draining lymph nodes (dLN) collected from in vivo EAM-induced wild type and CD69−/− mice. N=6 animal per group (mean with SEM). B Analysis of miR-721 expression in exosomes from sorted Treg and Th17 cells cultured 48 h. ND stands for Non-detected. Mean±SEM.

In this setting we proved that miR-721 is expressed in the exosomal fraction of EAM draining lymph nodes (FIG. 34A). Since it is upregulated in serum and dLN of mice that present an augmented Th17 response (CD69−/− mice), we hypothesized that miR-721 could be secreted by Th17 cells into exosomes. EAM-induced dLN were sorted to obtain >90% pure in vivo differentiated Th17 and Treg cell culture. After exosome collection from 48 h cultures, miR-721 analysis advocates for an upregulation in Th17-derived exosomes compared with Treg-derived exosomes. miR-721 is expressed in the exosomal fraction of Th17 cells in mice with moderate myocarditis (WT) and severe myocarditis (CD69−/−) (FIG. 34B).

5.3. Selection Criteria of Patients to the Study

We have recruited patients aged from 20 to 80 years.

Patients with Myocarditis:

we will recruit patients of acute myocarditis with at least one of the following parameters: chest pain, elevation of the ST segment, elevated Troponin T or I, low ejection fraction. Although we have also included in the viral cardiomyopathy, Chagas and Takotsubo study and dilated heart diseases (chronic myocarditis).

Patients with AMI:

The patients will be divided into three groups: 1) non-ST elevation acute coronary syndrome (NSTACS) group, confirmed by the lack of ST segment elevation and a significant rise of creatine kinase MB and troponin I levels, unstable angina confirmed by chest pain at rest with definite ischemic proof including ST segment changes and/or T-wave inversion, and angiographic evidence of coronary artery stenosis (>70%)), 2) chronic stable angina (CSA) group; inclusion criteria, effort angina (without a previous history of unstable angina or myocardial infarction) and angiographic evidence of coronary artery stenosis (>70%), and 3) chest pain syndrome (CPS) group, inclusion criterion, chest pain with no accompanying electrocardiographic changes, coronary artery stenosis, or coronary spasm. None of the patients will be currently treated with anti-inflammatory drugs such as non-steroidal anti-inflammatory drugs, steroids, etc.

5.4. Data Base of Clinical Parameters from the Patients.

Figure 35:
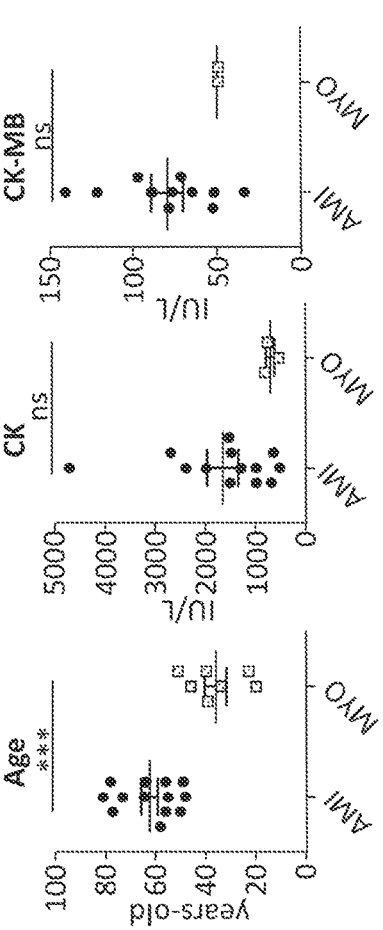
FIG. 35 shows the clinical parameters of some of the patients with AMI and Myocarditis included in the study. ECG; electrocardiogram, MRI; magnetic resonance imaging, ABX; antibiotics, CK; creatinine kinase.

The anonymous samples received from the different hospital were listed in a data base were the clinical data (Heart function: ECG & Echocardiography, Heart damage: TPI, CK-MB . . . , Magnetic Resonance Imaging with gadolinium enhancement, Dyslipidemia and others) of the patients was specified. An example of the clinical parameters and a summary of the data is represented in FIG. 35.

5.5. The Following Blood Samples Parameters have been Analyzed:
—Analysis of Th17 and Tregs in Patients.

Analysis has been performed from at least 2 ml of blood. 1 ml for plasma analysis and 1 ml for peripheral blood leukocutes (PBLs) analysis after Ficoll treatment.

PBLs from healthy donors or patients with Myocarditis or AMI were collected and analyzed by flow cytometry to analyze the proportions in circulating Treg and Th17, Th1 and Th22 cells. Peripheral blood CD4+CD25+FOXP3+CD45RO-CD45RA+naïve Treg (nTreg) cells and CD4+CD25+FOXP3+CD45RO+CD45RA− memory Treg (mTreg) cells in CVD patients has been compared to healthy volunteers.

Figure 36A:
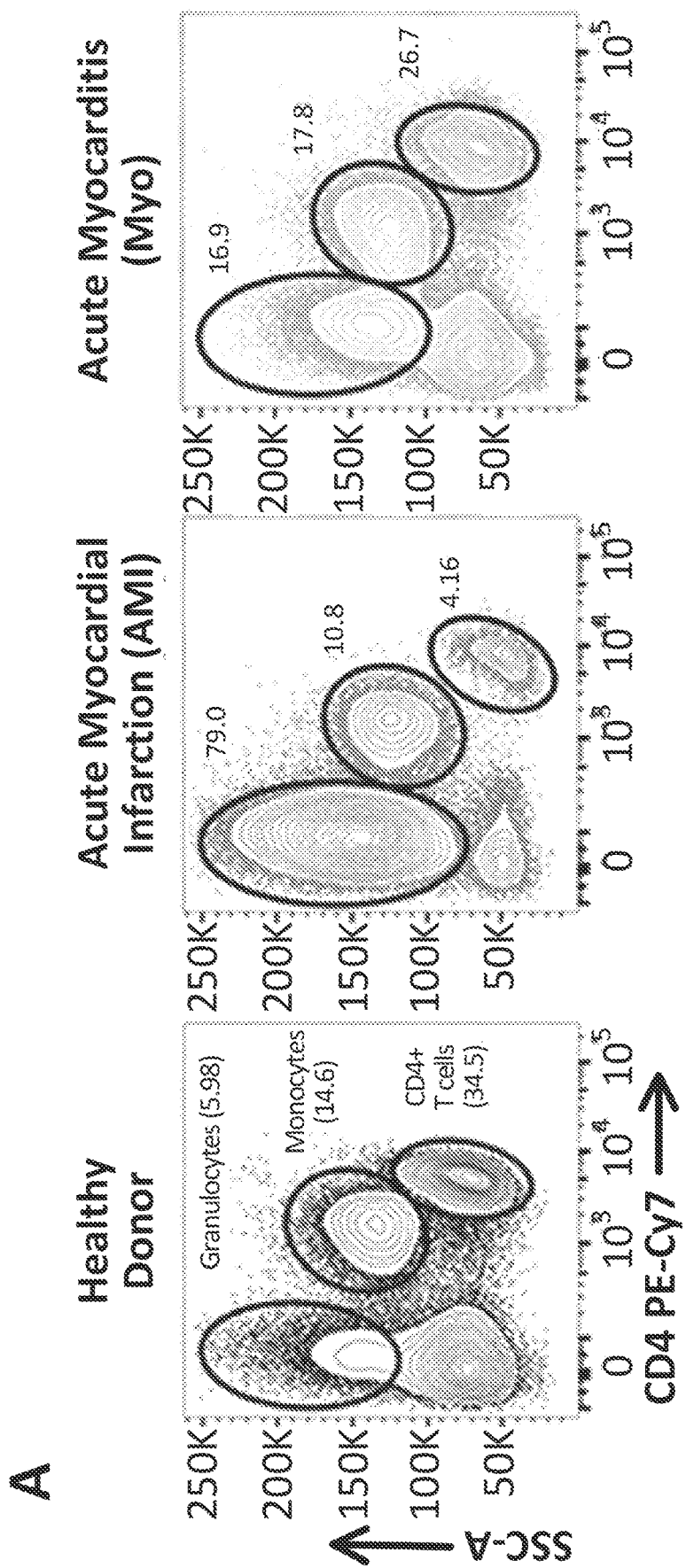
FIG. 36 shows the analysis by flow cytometry of the hematopietic lineages in Acute Myocarditis (Myo) and Acute myocardial infarction (AMI) patients compared to healthy volunteers. Percentages of Granulocytes, monocytes, CD4+ T cells are shown (A). Post-analysis gating CD4+ cells shows the percentages of Th1, Th17, Th22 and naïve and memory Regulatory T cells in the above samples (B).
Figure 36B:
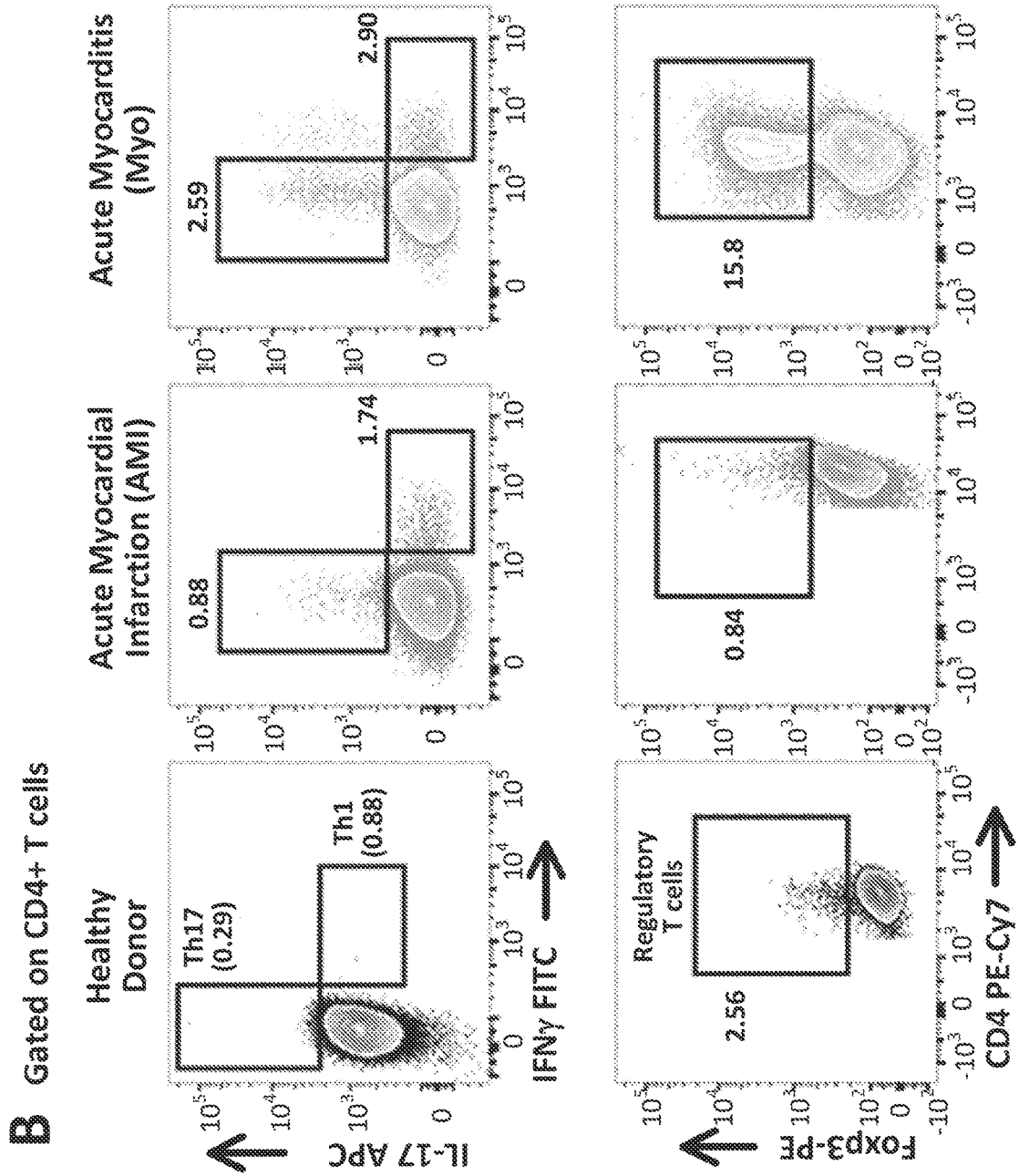
Figure 36B:
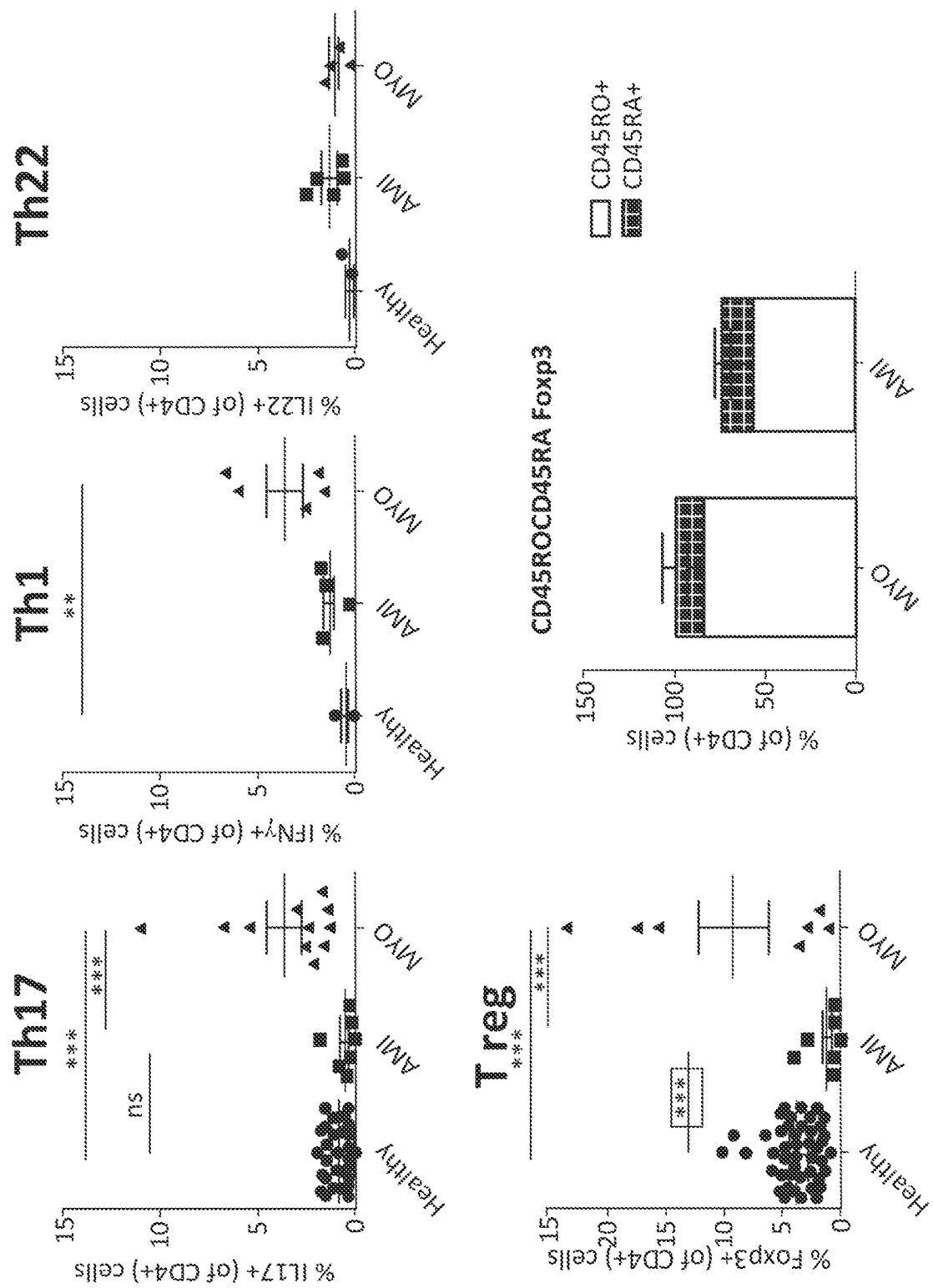

The response of the innate immune system seems to work the same way in both cardiomyopathies. Myocarditis and AMI patients have lower levels of monocytes and higher levels of granulocytes compared to healthy volunteers (FIG. 36A). The most interesting data that difference Myocarditis from AMI patients and healthy volunteers is that both memory and naïve Tregs and Th17 cells were significantly upregulated in the blood of myocarditis patients compared to AMI patients, whereas total CD4 T cells proportions do not change in the blood of myocarditis patients compared to AMI or healthy volunteers. All these data suggest that the changes in Treg and Th17 cells are distinctive from Myocarditis patients (FIG. 36B). Although there is a trend of higher Th1 in myocarditis patients data is not statistically significative from those of AMI patients.

Figure 37:
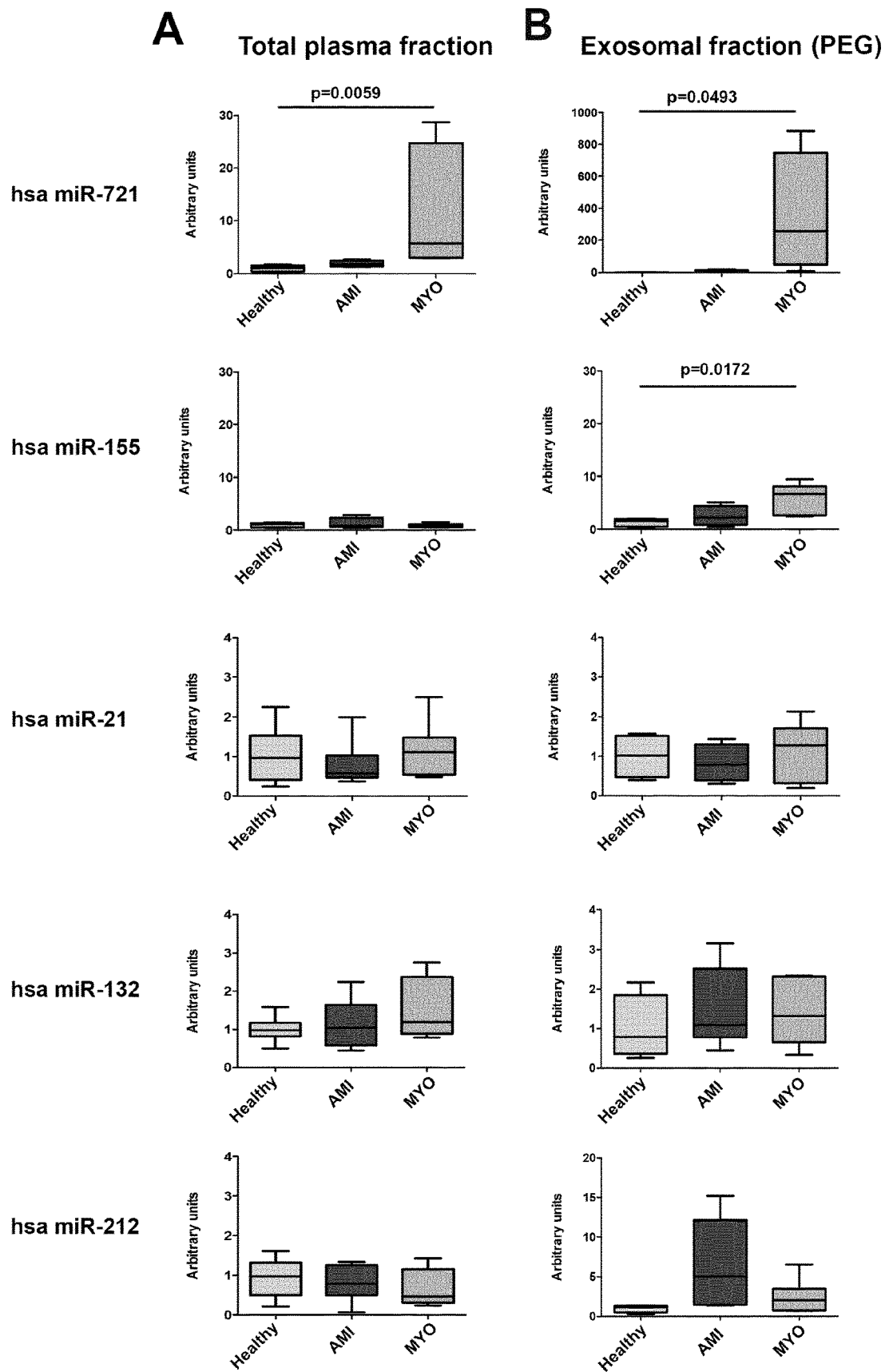
FIG. 37 shows the miRNA expression levels in the blood plasma of patients with Acute Myocarditis (Myo) and Acute myocardial infarction (AMI) patients compared to healthy volunteers (A). miRNA expression levels in the exosomal fraction of the blood plasma obtained after isolation by precipitation with polyethilenglycol (PEG) (B).

—miRNA Profiling in Plasma Samples of Patients.

miRNA expression levels were analyzed in plasma from patients by qPCR with exiqon probes for the indicated miRNAs. The microRNA content was evaluated by realtime quantitative-PCR. The data were first normalized versus an artificial microRNA (UniSp5, Ambion) equally added to each sample before the RNA isolation to minimize the effect of differences in the RNA purification yield among samples, following the standard method of $2^{-\Delta Ct}$. Hsa-miR-423-3p was proposed as the most stable miRNA among our samples by two freely-accessible online softwares: NormFinder and GeNorm. UniSp5-normalized samples were then normalized versus hsa-miR-423-3p. Taking the healthy volunteers as the control group, the fold increase in the normalized miRNA levels in the AMI and myocarditis patients was then calculated to evaluate the differences among groups (FIG. 37).

Plasma samples from Myocarditis patients have significantly increased levels of miR-721 compared to healthy volunteers whereas plasma samples from AMI patients do not, indicating that miR-721 is a good biomarker for Myocarditis patients (FIG. 37A). We also analyzed the levels of other microRNAs that has been previously described as abundant in AMI, such as miR-21 (Zhang Y. Eur Rev Pharmacol Sci. 2016), or microRNAs involved in Aryl Hydrocarbon-dependent Th17 differentiation as miR-132/212 (Nakahama T. PNAS 2013) (FIG. 37A). Surprisingly, none of these micro-RNAs were differentially expressed in any of the three groups of samples enhancing the hypothesis that miR-721 is expressed exclusively in the plasma of Myocarditis patients.

—miRNA Profiling in the Exosomal Fraction of Plasma Samples from Patients.

We analyzed miR-721 expression into exosomas from plasma samples from healthy volunteers and AMI and Myocarditis patients. With the number of samples analyzed until today, our data suggest that there is increased expression of miR-721 in the exosomal fraction of patients with myocarditis compared to the other groups (FIG. 37B). Moreover, we analyzed the levels of AMI-expressing miRNA miR-21 and Th17-related miRNAs miR212/132 in the exosomal fraction of the samples. However, none of the differences in the miRNA expression were statistically significant among the groups (FIG. 37B).

5.6. Diagnostic Approach for the First Cardiovascular Liquid Biopsy to Detect Myocarditis.

Figure 38:
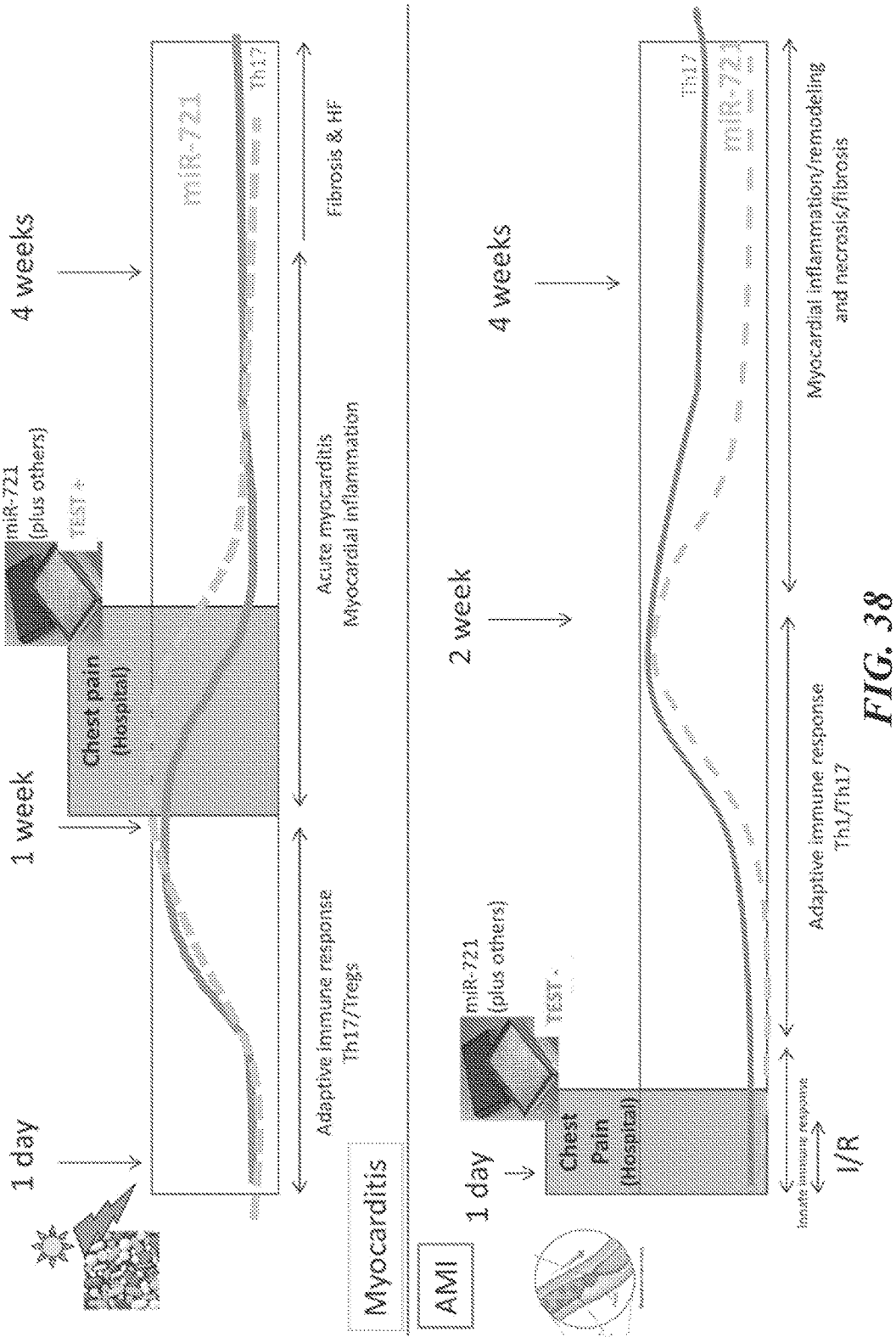
FIG. 38 shows a scheme of the diagnostic approach proposed as a Cardiovascular Liquid Biopsy. During Myocarditis progression the symptoms appear when the Th17 population is circulating n blood, so we can detect the presence of hsa-miR-721/155 in the blood plasma and secreted exosomes. Moreover, after an AMI when the symptoms appear the Th17 population is absent in blood and therefore we are not able to detect hsa-miR-721/155 in the blood plasma or secreted exosomes. These differences in the two cardiomyopathies make possible to use the presence of hsa-miR-721/155 in blood plasma or exosomes as a differential diagnostic marker for Myocarditis patients just taking a sample of blood or with a "Cardiovascular Liquid Biopsy" without the need to perform an endomiocardial Biopsy.

With the data obtained from mice and patients with AMI and Myocarditis we proposed miR-721 as a bona-fide biomarker for Myocarditis diagnosis exclusive to other ischemic cardiomyopathies as Acute Myocardial Infarction. Along myocarditis progression myocardial damage released heart antigens and a specific memory Th17 and Regulatory T cells arises within the first weeks of disease progression. At the moment of the acute symptoms of Myocarditis the Th17 response has taken place and the levels of this population are enhanced in blood. On the contrary, the acute symptoms of the AMI patients takes place in the first hours after the coronary artery ischemia, at that moment no Th17 is developed against heart antigens. The different nature of these two cardiomyopathies will allow us to differentially diagnose them by analyzing the levels of miR-721 in the plasma samples. We have identified miR-721 as exclusively expressed in Th17 cells that is released to the plasma into exosomes from Myocarditis patients, compared to AMI patients and healthy volunteers. The diagnostic approach is outlined in FIG. 38.

Example 6

6.1. Materials and Methods
Animals and Cell Lines

WT and CD69−/− double reporter (FoxP3-RFP, IL-17-eGFP) mice in C57BL/6 background were used for ex-vivo polarization assays and Th17/Treg/Th22 progression analysis during EAM. BALB/c mice were used as a background for the mixed bone marrow chimeras. All animals maintained at Animal facility of CNIC. All animal procedures were approved by the ethics committee of the Comunidad Autónoma de Madrid and were conducted in accordance with institutional guidelines that comply with the National Institutes of Health's Guide for the Care and Use of Laboratory Animals.

Induction of EAM

Mice were immunized subcutaneously on days 0 and 7 with 100 pg/0.2 mL MyHC-α peptide (MyHC-α614-629) Ac-RSLKLMATLFSTYASADR-OH (SEQ ID NO: 5) emulsified 1:1 in complete Freund adjuvant (1 mg/mL; H37Ra; Difco Laboratories, Detroit, Mich.). Animals were sacrificed on day 6 to extract draining lymph nodes for ex-vivo culture or on either days 20-21 or 50-52 to analyze the acute and chronic phase of the disease respectively.

Intracellular Staining and FACS Analysis

Single cell suspension prepared from mouse axillar and inguinal lymph nodes in FACS buffer (PBS, 0.5% BSA, 1 μM EDTA, 0.1% NaN3). Peripheral Blood Multinucleated Cells isolated from mouse or human blood samples using Ficoll-Isopaque (density=1.121 g/ml) gradient centrifugation. Cell suspensions were stained with fluorochrome-conjugated either human or mouse specific antibodies against CD4, CD3, CD25, CD45RO, CD45RA, IL-17a, IL-22, IFNγ and FoxP3 obtained from eBiosciences. For intracellular staining, cells were stimulated with 50 ng/ml phorbolmyristate acetate (PMA) and 750 ng/ml ionomycin (P+I) plus brefeldin A (1 μg/ml) in complete culture medium for 3 hrs. Cells were analyzed by BD FACSCanto/FACS- Fortessa Flow Cytometers. Ex-vivo culture and Treg/Th17 cell isolation. Cell suspensions from lymph nodes were cultured (2×107 cells/nil) during 48 h in exosome-free TexMACS media (Miltenyi Biotech) with MyHC peptide (10 ug/ml) and IL-23 (10 ng/ml). Afterwards, sorting for FoxP3RFP and IL-17eGFP using the BD FACs Aria II cell sorter/iCyt Synergy 4L cell sorter. Sorted cells were cultured again in TexMACS media 48 h with MyHC peptide and either IL-2 for Foxp3+ cells (Treg) or IL-23 for IL-17+ cells (Th17).

MicroRNA Extraction and Real-Time Quantitative-PCR

MiRNAs were extracted using miRNeasy mini kit (Qiagen) and was screened for purity and concentration in a Nanodrop-1000 Spectrophotometer (Thermo Scientific). Analysis of miRNA-721, sno-135, sno-202, let-7a, let-7b and let-7d was done using TaqMan MicroRNA Reverse Transcription Kit and individual TaqMan MicroRNA probes for retrotranscription. TaqMan Universal PCR Master Mix was used for Real-time quantitative PCR (Applied Biosystem). Analysis of miRNA expression was done using SDS software (Applied Biosystems) and relative expression checked by $2\text{-}\Delta \Delta CT$ method. Sno-135 and sno-202 were used as endogenous control for serum, cell and tissue samples; and let-7a, let-7b and let-7d for isolated exosomal fractions. Real-time quantitative Polymerase Chain Reaction (RT-qPCR) was performed on ABI Prism 7900HT 384 (Applied Biosystems).

Exosome Purification

Supernatants from pre-sorted lymph nodes cells or post-sorted Tregs/Th17 were collected after 48 h. Briefly, rest of cells were pelleted (2000 rpm for 10 min). For miRNA isolation, exosomes were precipitated by adding 0.4 volumes of 50% Polyethylene glycol 6000 (Sigma Aldrich) in 375 mM NaCl to the samples, storing 30 min at 4° C. and centrifugation 1500 g at 4° C.

Echocardiography and Magnetic Resonance Imaging

Mice were anaesthetized by inhalation of isoflurane/oxygen (1.25%/98.75%). For echocardiography, mice were examined by a 30 MHz transthoracic echocardiography probe and images were obtained with Vevo 770 (VisualSonics, Toronto, Canada) before EAM induction and during acute and chronic phases. From these images, left ventricle (LV) function was estimated by ejection fraction obtained from the M mode. For Magnetic Resonance Imaging with T1 and T2 mapping, late gadolinium enhancement was used via intravenous injection. Up to 13 slices of each heart were imaged and myocardial water content was evaluated by averaging 3-5 ROI (brightness) values all along each myocardial slice and normalizing with the brightness of the gadolinium in the lumen of both left and right ventricles.

Histology

Hearts were fixed in 10% phosphate-buffered formalin and embedded in paraffin. Sections were cut and stained with Haematoxilin-eosin to determine the level of inflammation and with Masson's trichrome to detect collagen deposition. Histological analysis was performed on a Nikon Eclipse 90i microscope. H&E stained sections were scored for inflammation as follows: 0, no inflammatory infiltrates; 1, small foci of inflammatory cells; 2, larger foci of >100 inflammatory cells; 3, 10-30% of a cross section occupied by inflammatory cells; 4, >30% of a cross section occupied (Cruz-Adalia et al, 2010).

Statistical Analysis

All the variables are expressed as Mean±Standar Deviation of the Mean (SEM). Statistical analysis was performed assessing first for the normality of the distributions using Kolmogórov-Smirnov test. If normal, unpaired Student t-test for two groups and one-way ANOVA analysis for multiple comparisons. If not normal distributions, U-Mann-Whitney test for two groups analysis and Kruskal-Wallis test for multiple comparisons. All the analyses were performed with GraphPad Prism 6.0 software.

TABLE 2

| MOUSE | | | Fold Induction | |
| --- | --- | --- | --- | --- |
| Ischemia serums | | ng/reaction | WT (3) | KO (3) |
| 50 ul serum | | | | |
| Preischemia | 450 ng | 30 | baseline levels | baseline levels |
| DAY1 | 225 ng | 30 | baseline levels | baseline levels |
| DAY3 | 225 ng | 30 | baseline levels | 3.4 |
| 100 ul serum | | | | |
| DAY 7 | 1500 ng | 30 | baseline levels | 10 |
| | | | Fold Induction | |
| Mlecs | 0.5e6 cells | | WT (7) | KO (7) |
| Control | 1500 ng | | not detected | baseline levels |
| TNFalpha | 1500 ng | | not detected | 1.2 |
| PMA/IO | 1500 ng | | not detected | 1.5 |

TABLE 2-continued

| MOUSE Myocarditis serums | EAM 100 ul serum | ng/reaction | Fold Induction WT (11) | Fold Induction KO (12) |
|---|---|---|---|---|
| Control | 1000 ng | 40 | baseline levels | 0.7 |
| Myocarditis | 1000 ng | 40 | 8.7 | 20 |

| HUMAN Myocarditis patient serums | | | Fold Induction | | | |
|---|---|---|---|---|---|---|
| | 200 ul serum | ng/reaction | Control (9) | Acute M. | Chronic M. | Chagas | Takotsubo |
| Control | 350 ng | 25 | 0.27 | | | | |
| Myocarditis | 350 ng | 25 | | 37 | 3.7 | 44 | 17 |

The invention claimed is:

1. A kit comprising:
   a first probe comprising (i) a first oligonucleotide and (ii) a first fluorescent label, wherein the first oligonucleotide hybridizes to the full length of SEQ ID NO: 4 with no mismatches; and
   a second probe comprising (i) a second oligonucleotide and (ii) a second fluorescent label, wherein the second oligonucleotide hybridizes to the full length of SEQ ID NO: 3 with no mismatches.

2. The kit according to claim 1, further comprising written instructions to contact the first and second probes with a plasma, serum or blood sample obtained from a human subject.

3. The kit according to claim 1, further comprising written instructions to disrupt a membrane of exosomes in a biological sample obtained from a human subject, thereby releasing SEQ ID NO: 4 from the exosomes.

4. A composition comprising:
   a first probe comprising (i) a first oligonucleotide which hybridizes to the full length of SEQ ID NO: 4, with no mismatches, and (ii) a first fluorescent label; and,
   a second probe comprising (i) a second oligonucleotide which hybridizes to the full length of SEQ ID NO: 3, with no mismatches, and (ii) a second fluorescent label.

5. The kit of claim 1, further comprising a polyT oligonucleotide primer.

6. The kit of claim 1, wherein the first probe is immobilized on a surface.

7. The kit of claim 6, wherein the second probe is immobilized on the surface.

8. The kit of claim 1, further comprising a lysis agent capable of disrupting a membrane of exosomes.

9. The composition of claim 4, further comprising a lysis agent capable of disrupting a membrane of exosomes.

10. The kit of claim 1, wherein the first probe consists of (i) the first oligonucleotide and (ii) the first fluorescent label, and wherein the second probe consists of (i) the second oligonucleotide and (ii) the first fluorescent label.

11. The composition of claim 4, wherein the first probe consists of (i) the first oligonucleotide and (ii) the first fluorescent label; and wherein the second probe consists of (i) the second oligonucleotide and (ii) the second fluorescent label.

* * * * *